US007915483B2

(12) United States Patent
Reinl et al.

(10) Patent No.: US 7,915,483 B2
(45) Date of Patent: Mar. 29, 2011

(54) C-TERMINALLY TRUNCATED INTERFERON

(75) Inventors: Stephen J. Reinl, Sacramento, CA (US);
Gregory P. Pogue, Vacaville, CA (US)

(73) Assignee: Biolex Therapeutics, Inc., Pittsboro, NC (US)

( * ) Notice: Subject to any disclaimer, the term of this patent is extended or adjusted under 35 U.S.C. 154(b) by 175 days.

(21) Appl. No.: 11/874,607

(22) Filed: Oct. 18, 2007

(65) Prior Publication Data
US 2009/0025106 A1 Jan. 22, 2009

Related U.S. Application Data

(63) Continuation of application No. 11/172,549, filed on Jun. 29, 2005, now abandoned.

(60) Provisional application No. 60/592,479, filed on Jul. 29, 2004.

(51) Int. Cl.
C12N 15/82 (2006.01)
A01H 5/00 (2006.01)
C07H 21/04 (2006.01)

(52) U.S. Cl. ........ 800/288; 800/278; 800/280; 800/294; 800/295; 800/298; 536/23.52; 435/419; 435/320.1

(58) Field of Classification Search .................. None
See application file for complete search history.

(56) References Cited

U.S. PATENT DOCUMENTS

| | | | |
|---|---|---|---|
| 4,956,282 A | 9/1990 | Goodman et al. | |
| 5,550,038 A | 8/1996 | Goodman et al. | |
| 5,629,175 A | 5/1997 | Goodman et al. | |
| 6,040,498 A | 3/2000 | Stomp et al. | |
| 6,096,547 A | 8/2000 | Goodman et al. | |
| 6,610,830 B1 | 8/2003 | Goeddel et al. | |
| 6,774,283 B1 | 8/2004 | Goodman et al. | |
| 6,815,184 B2 | 11/2004 | Stomp et al. | |
| 7,161,064 B2 | 1/2007 | Stomp et al. | |
| 2002/0088027 A1 | 7/2002 | Stomp et al. | |
| 2003/0115640 A1 | 6/2003 | Stomp et al. | |
| 2003/0135887 A1 | 7/2003 | Brandle et al. | |
| 2003/0167531 A1 | 9/2003 | Russell et al. | |
| 2004/0073968 A1 | 4/2004 | Stomp et al. | |
| 2004/0219131 A1 | 11/2004 | Patten et al. | |
| 2005/0060776 A1 | 3/2005 | Stomp et al. | |
| 2005/0221344 A1 | 10/2005 | Welcher et al. | |
| 2006/0195946 A1 | 8/2006 | Dickey et al. | |
| 2007/0044177 A1 | 2/2007 | Stomp et al. | |
| 2007/0128162 A1 | 6/2007 | Dickey et al. | |
| 2009/0282584 A1 | 11/2009 | Stomp et al. | |

FOREIGN PATENT DOCUMENTS

| | | |
|---|---|---|
| AT | 393690 B | 11/1991 |
| EP | 0032134 B2 | 7/1981 |
| EP | 0141484 A2 | 5/1985 |
| EP | 0 194 006 A1 | 9/1986 |
| EP | 0 256 424 A1 | 2/1988 |
| WO | WO 01/36001 A2 | 5/2001 |
| WO | WO 02 10414 A2 | 2/2002 |
| WO | WO 02 43650 A2 | 6/2002 |
| WO | WO 03/002152 A2 | 1/2003 |
| WO | WO 2004/046365 A2 | 6/2004 |
| WO | WO 2005/035767 | 4/2005 |

OTHER PUBLICATIONS

Sugyiama et al. Expression of human interferon-a2 in Sf9 cells. (1993) Eur. J. Biochem; vol. 217; pp. 921-927.*
Zhu et al. Expression of human a-interferon cDNA in transgenic rice plants. (1994) Plant Cell, Tissue and Organ Culture; vol. 36; pp. 197-204.*
Schillberg et al. Review—Molecular farming of recombinant antibodies in plants. (2003) CMLA, Cell. Mol. Life Sci.; vol. 60; pp. 433-445.*
Ahn et al. A novel extensin gene encoding a hydroxyproline-rich glycoprotein requires sucrose for its wound-inducible expression in transgenic plants. (1996) The Plant Cell; vol. 8; pp. 1477-1490.*
Ackerman, S.K., et al., Biologic Activity in a Fragment of Recombinant Human Interferon α, *Proc. Natl. Acad. Sci., USA*, 1984, pp. 1045-1047, vol. 81.
Chang, N. T., et al., "Synthesis of a Human Leukocyte Interferon with a Modified Carboxy Terminus in *Escherichia coli*," *Archives of Biochemistry and Biophysics*, 1983, pp. 585.
Chang, et al., "Evolution of a cytokine using DNA family shuffling", *Nature Biotech*. (1999) 17:793-797.
Cheetham, B.F., et al., "Structure-Function Studies of Human Interferons-α: Enhanced Activity on Human and Murine Cells," *Antiviral Research*, 1991, pp. 27-40, vol. 15.
Cohen, "The manipulation of genes", *Scientific American* (1975) pp. 25-33.
Franke, A.E., et al., "Carboxyterminal Region of Hybrid Leukocyte Interferons Affects Antiviral Specificity," DNA, 1982, vol. 1(3).
Gasdaska, J.R., et al., Advantages of Therapeutic Protein Production in the Aquatic Plant *Lemna*, www.bioprocessingjournal.com, Mar./Apr. 2003.
Green, et al., "Isolation and cell-free translation of immunoglobulin messenger RNA", *Arch. of Biochem. and Biophy.* (1976) 172:74-89.
Guarente, et al., "Improved methods for maximizing expression of a cloned gene: a bacterium that synthesizes rabbit beta-globin", *Cell* (1980) 20:543-553.
Guarente, et al., "A technique for expressing eukaryotic genes in bacteria", *Science* (1980) 209(4463):1428-1430.
Houghton, "Human interferon gene sequences", *Nature* (1980) 285(5766):536.
Itakura, et al., "Expression in *E. coli* of a chemically synthesized gene for the hormone somatostatin", *Science* (1977) 198(4321):1056-1063.
Levy, et al., "Amino acid sequence of a human leukocyte interferon", *Proc. Natl. Acad. Sci. USA* (1981) 78(10):6186-6190.

(Continued)

*Primary Examiner* — Cathy Kingdon Worley
(74) *Attorney, Agent, or Firm* — Alston & Bird LLP

(57) ABSTRACT

The invention described herein provides a C-terminally truncated interferon having a deletion of 7, 8, or 9 amino acids and having enhanced biological activity, and the polynucleotides encoding such an interferon. Also provided are methods for producing and using such truncated interferon. In some embodiments, the truncated interferon is produced in a plant.

11 Claims, 3 Drawing Sheets

OTHER PUBLICATIONS

Mantei, et al., "The nucleotide sequence of a cloned human leukocyte interferon cDNA", *Gene* (1980) 10:1-10.

Mantei, et al., "The nucleotide sequence of a cloned human leukocyte interferon cDNA", *Chemical Abstracts* (1980) 93:489, Abstract No. 130319s.

Miller, "Use of recombinant DNA technology for the production of polypeptides", *Adv. Exp. Med. Biol.* (1979) 118:153-174.

Nagata, et al., "The structure of one of the eight or more distinct chromosomal genes for human intereferon-alpha", *Nature* (1980) 287(5781):401-408.

Nagata, et al., "Synthesis in *E. coli* of a polypeptide with human leukocyte interferon activity", *Chemical Abstracts* (1980) 93:479, Abstract No. 41286m.

Nagata, et al., "Synthesis in *E. coli* of a polypeptide with human leukocyte interferon activity", *Nature* (1980) 284:316-320.

Ozes, et al., "A comparison of Interferon-Con1 with natural recombinant interferons-alpha: antiviral, antiproliferative, and natural killer-inducing activities", *J. Interferon Res.* (1992) 12:55-59.

Pestka and Langer, "Interferons and their actions", *Ann. Rev. Biochem.* (1987) 56:727-77.

Platis and Foster, "High yield expression, refolding, and characterization of recombinant interferon α2/α8 hybrids in *Escherichia coli*", *Protein Expression and Purfication* (2003) 31:222-230.

Prouty, et al., "Degradation of abnormal proteins in *Escherichia coli*", *J. Bio. Chem.* (1975) 250(3):1112-1122.

Roberts, et al., "Synthesis of Simian Virus 40 t Antigen in *Escherichia coli*", *Proc. Natl. Acad. Sci. USA* (1979) 76(11):5596-5600.

Roberts, et al., "A General Method for Maximizing the Expression of a Cloned Gene", *Proc. Natl. Acad. Sci. USA* (1979) 76(2):760-764.

Rubinstein, et al., "Human leukocyte interferon: isolation and characterization of several molecular forms", *Arch. of Biochem. and Biophysics* (1981) 210:307-318.

Rubinstein, et al., "Human leukocyte interferon purified to homogeneity", *Science* (1978) 202(4374):1289-1290.

Rubinstein, et al., "Human leukocyte interferon: production, purification to homogeneity, and initial characterization", *Proc. Natl. Acad. Sci. USA* (1979) 76(2):640-644.

Schouten, et al., "Improving scFv antibody expression levels in the plant cytosol", *FEBS Letters* (1997) 415:235-241.

Staehelin, et al., "Production of Hybridomas Secreting Monoclonal Antibodies to the Human Leukocyte Interferons", *Proc. Natl. Acad. Sci. USA* (1981) 78(3):1848-1852.

Stebbing, et al., "Biological comparison of natural and recombinant DNA-derived polypeptides", *State of the Art: Insulin and Growth Hormone* (1980) pp. 12-21.

Streuli, et al., "At least three human type alpha interferons: structure of alpha 2", *Science* (1980) 209(4463):1343-1347.

Taniguchi, et al., "Expression of the Human Fibroblast Interferon Gene in *Escherichia coli*", *Proc. Natl. Acad. Sci. USA* (1980) 77(9):5230-5233.

Taniguchi, et al., "Human leukocyte and fibroblast interferons are structurally related", *Nature* (1980) 285:547-549.

Torma and Paucker, "Purification and characterization of human leukocyte interferon components", *J. Biol. Chem.* (1976) 251(16):4810-4816.

Weissmann, "The cloning of interferon and other mistakes", *Interferon* (1981) 3:101-134.

Zoon, et al., "Amino terminal sequence of the major component of human lymphoblastoid interferon", *Science* (1980) 207(4430):527-528.

Zoon, et al., "Purification and partial characterization of human lymphoblastoid interferon", *Proc. Natl. Acad. Sci. USA* (1979) 76(11):5601-5605.

Zoon, et al., "Human lymphoblastoid interferon: purification, amino acid composition, and amino-terminal sequence", *Ann. NY Acad. Sci.* (1980) 350:390-398.

Arnheiter, H., et al., "Orientation of a Human Leukocyte Interferon Molecule on its Cell Surface Receptor: Carboxyl Terminus Remains Accessible to a Monoclonal Antibody Made Against a Synthetic Interferon Fragment," *Proc. Natl. Acad. Sci., USA*, 1983, pp. 2539-2543, vol. 80.

Döbeli, H. et al., "Role of the carboxyl-terminal sequence on the biological activity of human immune interferon (IFN-Gamma)," *Journal of Biotechnology*, 1988, vol. 7(3), pp. 199-216.

Horisberger, M. et al., "Interferon-Alpha Hybrids," *Pharmacology & Therapeutics*, 1995, vol. 66(3), pp. 507-534.

Nacheva, G. et al., "Human interferon gamma: significance of the C-terminal flexible domain for its biological activity," *Archives of Biochemistry and Biophysics*, 2003, vol. 413(1), pp. 91-981.

\* cited by examiner

C-TERMINALLY TRUNCATED INTERFERON

CROSS REFERENCE TO RELATED APPLICATIONS

This application is a continuation of U.S. application Ser. No. 11/172,549, filed Jul. 29, 2005, which claims the benefit of U.S. Provisional Application No. 60/592,479, filed on Jul. 29, 2004, the contents of both of which are herein incorporated by reference in their entirety.

FIELD OF USE

The present invention relates to the fields of molecular biology and medicine and provides a C-terminally truncated interferon alpha with enhanced biological properties.

BACKGROUND OF THE INVENTION

The publications and other materials referred to herein to describe the background of the invention and to provide additional detail with regard to the practice of this invention are incorporated herein by reference.

Interferons are proteins that are secreted from cells in response to a variety of stimuli. Interferons are classified as Type I and Type II, depending on the cell receptor to which they bind. Type I consists of seven classes, including interferon alpha, which is produced by human leukocytes, and interferon beta, which is produced by fibroblasts. Type II consists only of interferon gamma. Type I interferons exhibit a wide breadth of biological activity, including antiviral, antiproliferative, neoplastic and immunomodulatory activities. Therefore, they are useful in the treatment of a variety of diseases, including many viral diseases, such as viral hepatitis, and several cancers, such as hairy cell leukemia, Kaposi's sarcoma, chronic myelogenous leukemia and metastatic malignant melanoma.

Human interferon was first isolated in 1957 by Isaacs and Lindenmann. Isaacs A. and Lindenmann J., "Virus interference. I. The interferon," *Proc. R. Soc. Lond. Ser. B. Biol. Sci.* (1957) 147: 258-267. Many years later, interferon cDNAs from a virus-induced myeloblast cell line were analyzed, revealing the presence of many distinct species of interferon. Although analysis of this cDNA revealed differences in amino acid sequences, all reports suggested that active human leukocyte interferons (interferon alpha) had 165 or 166 amino acids. Levy, however, reported that a significant fraction of active interferon isolated from human leukocytes lacked the ten carboxy-terminal amino acids suggested from the DNA sequence of such interferons. See Levy, W. P., et al., "Amino acid sequence of a human leukocyte interferon," *Proceedings of the National Academy of Sciences* (1981) 78(10): 6186-6190. In addition, Levy reported that this C-terminal truncation did not affect the specific activity of these proteins, thus indicating that the 10 COOH-terminal amino acids were not essential for interferon activity. See id. at 1689.

Nevertheless, bacterially produced recombinant interferon alpha (2a and 2b), which was approved for therapeutic use in 1986, has 165 amino acids. Researchers have attempted to enhance the biological activity of interferon alpha through modifications to the internal amino acids of the interferon rather than via carboxy terminal truncations. See, for example, Ozes, O. N., et al., "A comparison of interferon-con1 with natural recombinant interferons-α: antiviral, antiproliferative, and natural killer-inducing activities," *Journal of Interferon Research* (1992) 12:55-59.

The present invention relates to the surprising discovery that recombinant interferon alpha that is truncated at the carboxy terminus exhibits enhanced biological properties compared to full length interferon. Applicants made this discovery while conducting experiments aimed at optimizing expression of full length interferon alpha protein in plants. Such plant-produced protein demonstrates anti-viral and antiproliferative activity comparable to bacterially produced interferon alpha but contains C-terminal truncations that predominantly occur during processing of the plant material. A purification process was devised that reduced the carboxy terminal truncations to approximately 4% of the total interferon product but resulted in substantial loss of the desired product during processing. To obtain better yields and a more homogeneous product, Applicants prepared recombinant interferon alpha polypeptides lacking 1-9 of the C-terminal amino acids of full length interferon and found that these polypeptides displayed enhanced biological activity and enhanced processing qualities.

SUMMARY OF THE INVENTION

The present invention provides a polypeptide comprising a C-terminally truncated interferon, as that term is defined herein, with enhanced biological activity. In one embodiment this enhanced biological activity is antiproliferative activity. This invention also provides methods for producing and using such polypeptide.

In one embodiment the C-terminally truncated interferon polypeptides of this invention are derived from interferon alpha 2a. In yet another, they are derived from interferon alpha 2b.

The polypeptide of this invention has 156-164 amino acids. In one embodiment, this polypeptide has 156-158 amino acids. In another embodiment the polypeptide has an amino acid sequence of residues #1-156 of SEQ ID NO:2, residues #1-157 of SEQ ID NO:2, or residues #1-158 of SEQ ID NO:2.

Also provided is a composition comprising the polypeptide of this invention associated with a molecule capable of stabilizing the composition. In one embodiment the molecule is polyethylene glycol (PEG) or derivatives thereof.

The polypeptide of this invention may also be fused to a heterologous amino acid sequence. In one aspect of the invention, the heterologous amino acid sequence is a signal peptide. In another aspect, the signal peptide is extensin. In yet another aspect, the extensin is from *Nicotiana benthamiana*.

The polypeptide may be produced in various expression systems. In one embodiment, the polypeptide is produced in plants. In another embodiment it is produced by yeast. In still another embodiment it is microbially produced.

Also encompassed by this invention is a plant-produced C-terminally truncated interferon polypeptide with 156-158 amino acids that exhibits enhanced processing qualities. These enhanced processing qualities include enhanced stability in plant extracts, enhanced yield, and/or enhanced homogeneity at the C-terminus.

This invention also encompasses an artificial polynucleotide encoding a polypeptide comprising a C-terminally truncated interferon having enhanced biological activity. In one aspect, the encoded polypeptide has 156-158 amino acids.

In one embodiment, the artificial polynucleotide has one of the following sequences: nucleotides #1-468 of SEQ ID NO:1, nucleotides #1-471 of SEQ ID NO:1, or nucleotides #1-474 of SEQ ID NO:1.

In one embodiment, the artificial polynucleotide of this invention also comprises a nucleotide sequence that encodes the amino acid sequence of an extensin signal peptide. The extensin signal peptide nucleotide sequence is linked to the 5' end of the nucleotide sequence of the C-terminally truncated interferon.

This invention also provides an expression vector comprising the polynucleotide. In one embodiment the expression vector is a plasmid. In another embodiment, it is a viral vector.

In one aspect, a host cell contains the expression vector of this invention. The host cell may be a plant cell, a CHO cell, a bacterial cell or a yeast cell.

In another aspect, a plant contains such expression vector. The plant may be *Nicotiana benthamiana*. In one embodiment, the expression construct is delivered by a viral vector. In another embodiment, the expression construct is stably incorporated into the plant genome. This invention also provides a plant containing a C-terminally truncated interferon having enhanced antiproliferative activity.

Also provided is a process for producing a polypeptide comprising a C-terminally truncated interferon having enhanced biological activity comprising culturing a host cell of this invention and recovering the polypeptide from such host cell.

Also contemplated is a process for producing a polypeptide comprising a C-terminally truncated interferon having enhanced biological activity by transforming a plant with an expression construct of this invention. In one embodiment, this process includes infecting the plant with a viral vector of this invention. In another embodiment, an expression construct of this invention is stably incorporated into the genome of the plant. The process may further involve recovering the polypeptide from the plant.

This invention also encompasses a pharmaceutical composition comprising a C-terminally truncated interferon with enhanced biological activity. Also provided is a method for treating an interferon-affected disorder comprising administering to a patient a therapeutically effective amount of such pharmaceutical composition. In one embodiment, the pharmaceutical composition contains a pharmaceutically acceptable carrier. In another embodiment, the therapeutically effective amount comprises between 5-20 ug. The pharmaceutical composition may be administered subcutaneously, orally, via inhalation, intramuscularly, rectally, parenterally, enterically, transdermally, peritoneally, intratumorally, or intravenously These and other features and advantages of this invention are described in, or are apparent from, the following detailed description of various exemplary embodiments of the compositions and methods according to this invention.

BRIEF DESCRIPTION OF THE DRAWINGS

Various exemplary embodiments of this invention will be described in detail, with reference to the following figures.

DETAILED DESCRIPTION OF THE PREFERRED EMBODIMENT

Definitions

Recombinant interferons are valuable therapeutics, as they possess antiviral, antiproliferative and immunomodulatory activities. The present invention provides interferon alpha proteins with carboxy terminal truncations that have enhanced biological properties.

Figure 1:
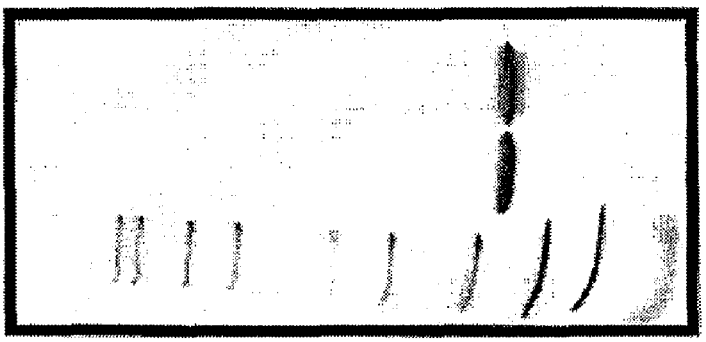
FIG. 1 is a Coomassie stained SDS-PAGE gel of full length interferon alpha 2a and 2b isolated from *Nicotiana benthamiana* and purified.

The term "full length interferon," as used herein, means interferon alpha having 165-166 amino acids, such as recombinant interferon alpha 2a and alpha 2b World Health Organization (WHO) references, recombinant interferon alpha National Institute of Health reference Gxa01-901-535, interferon alpha 2a and 2b of 165 amino acids described in the "Examples" section below and shown in FIG. 1, and interferon alpha of 165-166 amino acids isolated from human leukocytes.

A "C-terminally truncated interferon," as used herein, refers to an isolated interferon alpha protein, such as alpha 2a or alpha 2b, that differs from full length interferon in that it is truncated by 1-9 amino acids at its carboxy terminus, having 156-164 amino acids. The term "isolated" refers to a C-terminally truncated interferon protein that is recombinant or that is purified or partially purified from its production system.

"Enhanced biological activity," as used herein, means biological activity that is greater than that of full length interferon. Specifically, an interferon, such as a C-terminally truncated interferon, with enhanced biological activity has at least one biological activity, such as antiviral or antiproliferative activity, that is greater than that of full length interferon, based on standard tests used to evaluate such biological activities.

"Enhanced processing qualities," as used herein, refer to processing qualities that are improved compared to those of full length interferon. Specifically, an interferon, including a C-terminally truncated interferon, with enhanced processing qualities, has at least one processing quality, such as stability in crude extracts, yield, purity or ease of purification that is improved compared to that of full length interferon produced by the same means (e.g., in plants or bacterially).

An "interferon-affected disease" refers to a disorder or disease against which interferon is therapeutically effective, such as hepatitis C or hairy cell leukemia.

The term "transform," or any grammatical variant thereof, refers to introducing a heterologous polynucleotide into a host organism either by transient transfection, such as infection with a viral vector, or by stable incorporation into the plant genome.

C-Terminally Truncated Interferons and Enhanced Biological Activity

C-terminally truncated inteferons have enhanced biological activity. The biological activity of interferons, including antiviral activity, antiproliferative activity, regulation of functional cellular activities and immunomodulation, may be measured by several standard tests that are well known in the art. See Meager, A., "Biological assays for interferons," *Journal of Immunological Methods* (2002) 261: 21-36. For example, standard tests for antiviral activity include the cytopathic effect inhibition assay described in several references, including Rubinstein, S., Familletti, P. C. and Pestka, S. 1981. J Virol. 37, 755-758 and Familletti, P. C., Rubinstein, S., and Pestka, S. (1981) Methods in Enzymology, (S. Petska ed.) Academic Press, New York, 78: 387-394. Analyses of antiviral activity are described in detail in Examples 4 and 6, below.

In one embodiment, C-terminally truncated interferons exhibit enhanced antiproliferative activity as compared to full length interferon. Standard tests for antiproliferative activity include the Daudi cell line growth inhibition assay, described in detail in Examples 4 and 6, below, and inhibition assays using Eskol cells as described in Evinger, M., et al., "Recombinant human leukocyte interferon produced in bacteria has antiproliferative activity," *J. Biol. Chem.* (1981) 256: 2113-2114.

C-terminally truncated interferon proteins with enhanced biological activity are derived from full length interferon. In one embodiment, the full length interferon is interferon alpha 2a. In another, the full length interferon is interferon alpha 2b. The amino acid sequence of mature full length interferon alpha 2b is provided as SEQ ID NO:2. Interferon alpha 2a and interferon alpha 2b differ only by one amino acid. Specifically, alpha 2a has a lysine at position 23 and alpha 2b has an arginine at position 23. In addition, both lysine and arginine have basic side chains, making the difference between alpha 2a and alpha 2b very slight. Therefore, interferon alpha 2a and 2b have very similar biological activities. For example, they react similarly when modified at their carboxy termini, as shown in Example 4, in which the amino acid sequence KDEL (SEQ ID NO:64) is added to the carboxy termini of both full length interferon alpha 2a and full length interferon alpha 2b and both maintain the same antiproliferative activity and antiviral activity as unmodified full length interferon.

C-terminally truncated interferons with enhanced biological activity comprise between 156 and 164 amino acids. In a preferred embodiment, the C-terminally truncated interferon has 156 amino acids; in another it has 157 amino acids; in yet another it has 158 amino acids. In a particularly preferred embodiment, the C-terminally truncated interferon has the following amino acid sequence: residues #1-156 of SEQ ID NO:2, residues #1-157 of SEQ ID NO:2, or amino acids #1-158 of SEQ ID NO:2. As referred to herein, residue 1 refers to the first amino acid residue at the N-terminus of the mature interferon protein.

C-terminally truncated interferons described herein may also be fused to a secretory sequence of amino acids. In one embodiment, this secretory sequence is a signal peptide, which is a series of amino acids attached to the polypeptide that binds the polypeptide to the endoplasmic reticulum and is essential for protein secretion. Signal peptides have a specific cleavage site at the N-terminus of the mature protein or polypeptide. The signal peptide may be the native signal peptide of interferon or a heterologous signal peptide. The selected signal peptide preferably is one that is recognized and processed (i.e., cleaved by a signal peptidase) by the host cell or organism. Selection of an appropriate signal peptide is easily accomplished by one of ordinary skill in the art.

In a preferred embodiment, the signal peptide is the extensin signal peptide. In another preferred embodiment, the signal peptide is the extensin signal peptide from *Nicotiana benthamiana*, which has the amino acid sequence MGKMASLFATFLVVLVSLSLASESSA (residues #–26–-1 of SEQ ID NO:31 or of SEQ ID NO:33).

In another embodiment, the C-terminally truncated interferon described herein is fused to an endoplasmic reticulum retention signal. The amino acid sequence KDEL (SEQ ID NO:64) is one example of a useful carboxy terminus endoplasmic reticulum (ER) retention signal.

C-terminally truncated interferons with enhanced biological activity may be associated with a molecule capable of stabilizing the truncated interferon, e.g., by improving solubility, absorption, serum half life and the like. In one embodiment this stabilizing molecule is polyethylene glycol (PEG). One example of pegylation of interferon is provided in Grace, M. J., et al., "Site of pegylation and polyethylene glycol molecule size attenuate interferon-alpha antiviral and antiproliferative activities through the JAK/STAT signaling pathway," *J. Biol. Chem.* (2005) 280(8): 6327-36. In another embodiment, PEG derivatives may be used, such as those provided by Nobex (Research Triangle Park, N.C.), including the PEG-based polymers described in U.S. Pat. Nos. 6,815,530 and 6,835,802.

Another form of covalent modification for increased stability includes coupling of C-terminally truncated interferon with enhanced biological activity with one or more molecules of a polymer comprised of a lipophilic and a hydrophilic moiety as described in U.S. Pat. Nos. 5,681, 811 and 5,359, 030.

C-terminally truncated interferons may also be modified by chemical or enzymatic coupling of glycosides to the protein. Methods for such modification are described in the art. See, for example, Aplin, J. D. and Wriston, J. C., "Preparation, properties, and applications of carbohydrate conjugates of proteins and lipids," *CRC Crit Rev Biochem*. (1981) 10(4): 259-306.

Enhanced Processing Qualities

Plant-produced recombinant full length interferon proteins have antiviral and antiproliferative activity comparable to bacterially produced full length interferon but contain C-terminal truncations that occur primarily during processing of the plant material, as described in detail in Examples 1-3 below. Purification techniques allow a reduction of carboxy terminal truncations to approximately 4% of the purified full length interferon but result in substantial loss of the desired product during the processing and reduced yields. C-terminally truncated interferons with 156-158 amino acids do not have the above-referenced processing problems and, therefore, exhibit enhanced processing qualities.

Figure 2:
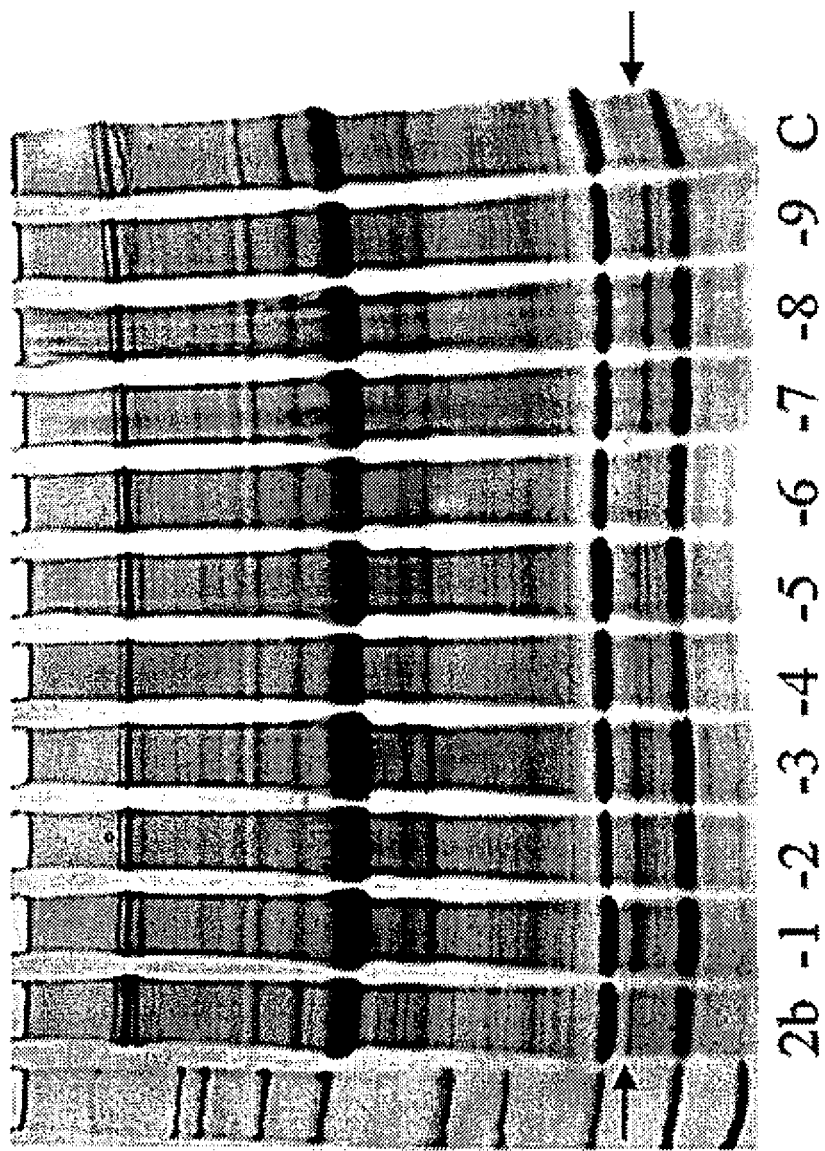
FIG. 2 is a Coomassie stained SDS-PAGE gel of plant homogenates containing various C-terminally truncated interferons produced in *N. benthamiana*. The arrow indicates the location of full-length interferon. The lane marked 2b corresponds to a crude plant extract containing full-length interferon. The lanes marked as $^-1$-$^-9$ correspond to plant homogenates containing truncated interferon products of viral vectors IFN-Δ1-IFN-Δ9, respectively.

In one embodiment, these enhanced processing qualities are reduced susceptibility to heterogeneity at the carboxy terminus. Referring to FIG. 2, C-terminally truncated interferons with 156-158 amino acids show decreased heterogeneity at the carboxy terminus, even in crude plant extracts. FIG. 2 provides a Coomassie-stained gel on which plant homogenates of *N. benthamiana* containing full length interferon and various C-terminally truncated interferon have been run. The arrow indicates the location of the band corresponding to full length interferon. As indicated on the gel, the lanes containing C-terminally truncated interferons with 156-158 amino acids (i.e., the lanes labeled −7, −8 and −9) accumulate well and show substantial homogeneity at the carboxy terminus compared to the other C-terminally truncated interferons.

Figure 3:
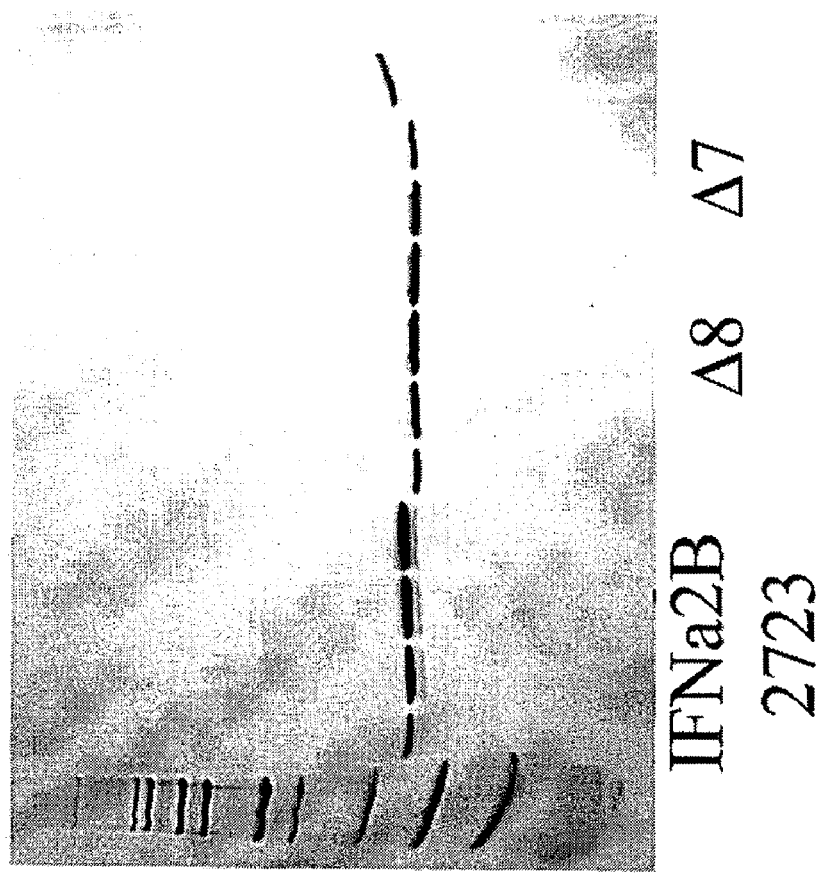
FIG. 3 is a Coomassie stained SDS-PAGE gel of various purified samples of full-length interferon and C-terminally truncated interferon isolated from *N. benthamiana* and purified. The lanes above IFNa2B2723 correspond to interferon products of viral vector LSBC 2723. The lanes above Δ8 and Δ7 correspond to the truncated interferon product of viral vectors IFN-Δ8 and IFN-Δ7, respectively.

In addition, C-terminally truncated interferons with 156-158 amino acids show reduced susceptibility to heterogeneity at the carboxy terminus after further purification, as evidenced by the single band of interferon appearing on the SDS-PAGE gel in FIG. 3 for C-terminally truncated interferons with 156-157 amino acids. FIG. 3 is an SDS-PAGE analysis of C-terminally truncated interferon proteins that have been further purified as described in the "Examples" section below. Similar results, although not shown in FIG. 3, were obtained with the C-terminally truncated interferon having 158 amino acids.

As described in detail in Examples 3 and 5, below, because of its greater stability in plants and plant tissue, purification of C-terminally truncated interferons with 156-158 amino acids is simpler than purification of full length interferon. In other words, C-terminally truncated interferon may be obtained at higher purity than full length interferon with fewer purification steps. This is in part because truncated interferons are more stable at protease sensitive pH levels of 4 to 7.

C-terminally truncated interferon having 156-158 amino acids are also improved as to processing in that yield of purified C-terminally truncated interferon is greater than that of full length interferon produced by the same means. As shown in Table 4, in the "Examples" section below, when C-terminally truncated interferon having 156-158 amino acids and full length interferon are produced in plants, the yield of C-terminally truncated interferon is significantly greater than that of full length interferon.

Processes for Production of C-terminally Truncated Interferon with Enhanced Biological Properties This invention also encompasses the artificial polynucleotides that encode C-terminally truncated interferons having enhanced biological activity. These polynucleotides encode a C-terminally truncated interferon with enhanced biological activity having 156-164 amino acids, and preferably 156-158 amino acids. In one embodiment, the encoded C-terminally truncated interferon is derived from interferon alpha 2a, while in another it is derived from interferon alpha 2b. In a preferred embodiment the polynucleotide has one of the following nucleotide sequences: nucleotides #1-468 of SEQ ID NO: 1, nucleotides #1-471 of SEQ ID NO: 1, or nucleotides #1-474 of SEQ ID NO: 1.

Polynucleotides of this invention may be incorporated into expression vectors that facilitate delivery of the polynucleotide to a desired host cell or organism. Such expression vectors contain expression control elements including a promoter. The polypeptide-coding polynucleotide sequences are operatively linked to the promoter to allow the promoter sequence to direct RNA polymerase binding and synthesis of the desired polypeptide. Useful in expressing the polypeptide-coding polynucleotide are promoters which are inducible, viral, synthetic, constitutive, temporally regulated, spatially regulated, and spatiotemporally regulated. The choice of which expression vector and ultimately to which promoter a polypeptide-coding polynucleotide is operatively linked depends directly, as is well known in the art, on the functional properties desired, e.g. the location and timing of protein expression, and the host cell to be transformed, these being limitations inherent in the art of constructing recombinant DNA molecules. However, an expression vector useful in practicing the present invention is at least capable of directing the replication, and preferably also the expression of the polypeptide-coding polynucleotide portion of the expression vector.

Such expression vectors may also encode a signal peptide that directs the newly synthesized protein to the secretory pathway of the cell in which the expression vector is expressed. The sequence encoding the signal peptide is fused in frame with the DNA encoding the polypeptide to be expressed. Signal peptides should be compatible with the expression system corresponding to the expression vector. For example, expression vectors used in plants may include the signal peptide sequence for extensin or α-amylase.

C-terminally truncated interferon with enhanced biological activity may be produced in various expression systems. Typical expression systems useful for expression of genes in various hosts are well known in the art and include bacteria cells transformed with recombinant plasmids; insect cell systems infected with recombinant virus expression vectors (e.g., baculovirus); yeast cells transformed with an expression vector; plant cell systems transformed with recombinant virus expression vectors (e.g., cauliflower mosaic virus (CaMV) or tobacco mosaic virus (TMV)) or with recombinant plasmid expression vectors (e.g., Ti plasmid); or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter or the vaccinia virus 7.5K promoter).

In addition, a host cell strain may be chosen which modulates the expression of the inserted sequences, or modifies and processes the gene product in the specific fashion desired. Such modifications (e.g., glycosylation) of protein products may be important for the function of the protein. Different host cells have characteristic and specific mechanisms for the post-translational processing and modification of proteins and gene products. Those of skill in the art can choose appropriate cell lines or host systems to ensure the correct modification and processing of the foreign protein expressed.

In a preferred embodiment, plant expression systems are transformed with an appropriate expression vector encoding a C-terminally truncated interferon with enhanced biological activity. In one embodiment, this involves the construction of a transgenic plant by integrating DNA sequences encoding the C-terminally truncated interferon of the present invention into the plant genome. Methods for such stable transformation are well known in the art.

In a particularly preferred embodiment, viral expression vectors are used to transform plants through transient infection. Both viral and non-viral vectors capable of such transient expression are available (Kumagai, M. H. et al. (1993) *Proc. Nat. Acad. Sci. USA* 90:427-430; Shivprasad, S. et al. (1999) *Virology* 255:312-323; Turpen, T. H. et al. (1995) *BioTechnology* 13:53-57; Pietrzak, M. et al. (1986) *Nucleic Acid Res.* 14:5857-5868; Hooykaas, P. J. J. and Schilperoort, R. A. (1992) *Plant Mol. Biol.* 19:15-38). Viral vectors are particularly preferred as they are easier to introduce into host cells and spread through the plant by infection to amplify expression of C-terminally truncated interferon.

A viral expression vector that expresses heterologous proteins in plants preferably includes (1) a native viral subgenomic promoter (Dawson, W. O. et al. (1988) *Phytopathology* 78:783-789 and French, R. et al. (1986) *Science* 231:1294-1297), (2) preferably, one or more non-native viral subgenomic promoters (Donson, J. et al. (1991) *Proc. Nat. Acad. Sci. USA* 88:7204-7208 and Kumagai, M. H. et al. (1993) *Proc. Nat. Acad. Sci. USA* 90:427-430), (3) a sequence encoding viral coat protein (native or not), and (4) nucleic acid encoding the desired heterologous protein. Vectors that include only non-native subgenomic promoters may also be used. The minimal requirement for the present vector is the combination of a replicase gene and the coding sequence that is to be expressed, driven by a native or non-native subgenomic promoter. The viral replicase is expressed from the viral genome and is required to replicate extrachromosomally. The subgenomic promoters allow the expression of the foreign or heterologous coding sequence and any other useful genes such as those encoding viral proteins that facilitate viral replication, proteins required for movement, capsid proteins, etc. The viral vectors are encapsidated by the encoded viral coat proteins, yielding a recombinant plant virus. This recombinant virus is used to infect appropriate host plants. The recombinant viral nucleic acid can thus replicate, spread systemically in the host plant and direct RNA and protein synthesis to yield the desired heterologous protein in the plant. In addition, the recombinant vector maintains the non-viral heterologous coding sequence and control elements for periods sufficient for desired expression of this coding sequence.

The recombinant viral nucleic acid is prepared from the nucleic acid of any suitable plant virus, though members of the tobamovirus family are preferred. The native viral nucleotide sequences may be modified by known techniques providing that the necessary biological functions of the viral nucleic acid (replication, transcription, etc.) are preserved. As noted, one or more subgenomic promoters may be inserted. These are capable of regulating expression of the adjacent heterologous coding sequences in infected or transfected plant host. Native viral coat protein may be encoded by this RNA, or this coat protein sequence may be deleted and replaced by a sequence encoding a coat protein of a different plant virus ("non-native" or "foreign viral"). A foreign viral coat protein gene may be placed under the control of either a native or a non-native subgenomic promoter. The foreign viral coat protein should be capable of encapsidating the recombinant viral nucleic acid to produce functional, infectious virions. In a preferred embodiment, the coat protein is foreign viral coat protein encoded by a nucleic acid sequence that is placed adjacent to either a native viral promoter or a non-native subgenomic promoter. Preferably, the nucleic acid encoding the heterologous protein, e.g., a C-terminally truncated interferon, to be expressed in the plant, is placed under the control of a native subgenomic promoter.

In another embodiment, a sequence encoding a movement protein is also incorporated into the viral vector because movement proteins promote rapid cell-to-cell movement of the virus in the plant, facilitating systemic infection of the entire plant.

Either RNA or DNA plant viruses are suitable for use as expression vectors. The DNA or RNA may be single- or double-stranded. Single-stranded RNA viruses preferably may have a plus strand, though a minus strand RNA virus is also intended.

The recombinant viral nucleic acid is prepared by cloning in an appropriate production cell. Conventional cloning techniques (for both DNA and RNA) are well known. For example, with a DNA virus, an origin of replication compatible with the production cell may be spliced to the viral DNA.

With an RNA virus, a full-length DNA copy of the viral genome is first prepared by conventional procedures: for example, the viral RNA is reverse transcribed to form +subgenomic pieces of DNA which are rendered double-stranded using DNA polymerases. The DNA is cloned into an appropriate vector and inserted into a production cell. The DNA pieces are mapped and combined in proper sequence to produce a full-length DNA copy of the viral genome. DNA encoding subgenomic promoter sequences with or without a coat protein gene, is inserted into non-essential sites of the viral nucleic acid as described herein. Non-essential sites are those that do not affect the biological properties of the viral nucleic acid or the assembled plant virion. cDNA complementary to the viral RNA is placed under control of a suitable promoter so that (recombinant) viral RNA is produced in the production cell. If the RNA must be capped for infectivity, this is done by conventional techniques. Examples of suitable promoters include the lac, lacuv5, trp, tac, lp1 and ompF promoters. A preferred promoter is the phage SP6 promoter or $T_7$ RNA polymerase promoter. Production cells can be prokaryotic or eukaryotic and include *Escherichia coli*, yeast, plant and mammalian cells.

Numerous plant viral vectors are available and well known in the art (Grierson, D. et al. (1984) *Plant Molecular Biology*, Blackie, London, pp. 126-146; Gluzman, Y. et al. (1988) *Communications in Molecular Biology: Viral Vectors*, Cold Spring Harbor Laboratory, New York, pp. 172-189). The viral vector and its control elements must obviously be compatible with the plant host to be infected. Suitable viruses are (a) those from the Tobacco Mosaic virus (TMV) group, such as TMV, Tobacco Mild Green Mosaic virus (TMGMV), Cowpea Mosaic virus (CMV), Alfalfa Mosaic virus (AMV), Cucumber Green Mottle Mosaic virus-watermelon strain (CGMMV-W), Oat Mosaic virus (OMV), (b) viruses from the Brome Mosaic virus (BMV) group, such as BMV, Broad Bean Mottle virus and Cowpea Chlorotic Mottle virus, (c) other viruses such as Rice Necrosis virus (RNV), geminiviruses such as Tomato Golden Mosaic virus (TGMV), Cassava Latent virus (CLV) and Maize Streak virus (MSV).

A preferred host is *Nicotiana benthamiana*. The host plant, as the term is used here, may be a whole plant, a plant cell, a leaf, a root shoot, a flower or any other plant part. The plant or plant cell is grown using conventional methods.

A preferred viral vector for use with *N. benthamiana* is a modified TTO1A vector containing a hybrid fusion of TMV and tomato mosaic virus (ToMV) (Kumagai, M H. et al. (1995) *Proc. Natl. Acad. Sci. USA* 92:1679-1683). As described in the "Examples" section, below, another viral vector useful for expressing C-terminally truncated interferon is DN15 (SEQ ID NO:24), which is derived from tobacco mosaic virus. The inserted subgenomic promoters must be compatible with TMV nucleic acid and capable of directing transcription of properly situated (e.g., adjacent) nucleic acids sequences in the infected plant. The coat protein should permit the virus to infect systemically the plant host. TMV coat protein promotes systemic infection of *N. benthamiana*.

Infection of the plant with the recombinant viral vector is accomplished using a number of conventional techniques known to promote infection. These include, but are not limited to, leaf abrasion, abrasion in solution and high velocity water spray. The viral vector can be delivered by hand, mechanically or by high pressure spray of single leaves.

C-terminally truncated interferon proteins with enhanced biological activity are recovered and purified using standard techniques known to those of skill in the art. Suitable methods include homogenizing or grinding the plant or the producing plant parts in liquid nitrogen to form crude plant extracts, or homogenates, followed by extraction of protein. In one embodiment, the polypeptide can be removed by vacuum infiltration and centrifugation followed by sterile filtration. Other purification methods are described in the "Examples" section, below. Protein yield may be estimated by any acceptable technique. Polypeptides are purified according to size, isoelectric point or other physical property. Following isolation of the total secreted proteins from the plant material, further purification steps may be performed. Immunological methods such as immunoprecipitation or, preferably, affinity chromatography, with antibodies specific for epitopes of the desired polypeptide may be used. Various solid supports may be used in the present methods: agarose®, Sephadex®, derivatives of cellulose or other polymers. For example, staphylococcal protein A (or protein L) immobilized to Sepharose® can be used to isolate the target protein by first incubating the protein with specific antibodies in solution and contacting the mixture with the immobilized protein A which binds and retains the antibody-target protein complex.

Using any of the foregoing or other well-known methods, the polypeptide is purified from the plant material to a purity of greater than about 50%, more preferably greater than about 75%, even more preferably greater than about 95%.

Methods for Use

C-terminally truncated interferons with enhanced biological activity are useful in the treatment of interferon-affected diseases, including various viral diseases, cancers and immune diseases. Their immunomodulatory properties also make them useful as adjuvants that modify immune responsiveness to various antigens and vaccines.

Pharmaceutical compositions of the present invention comprise C-terminally truncated interferon with enhanced biological activity in a form suitable for administration to a patient. Pharmaceutical compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of injectable compositions can be brought about by including in the composition an agent which delays absorption, for example, monostearate salts and gelatin.

Moreover, the pharmaceutical compositions of the present invention can be administered in a time release formulation, for example in a composition which includes a slow release polymer. The active compounds can be prepared with carriers that will protect the compound against rapid release, such as a controlled release formulation, including implants and microencapsulated delivery systems. Many methods for the preparation of such formulations are patented or generally known to those skilled in the art.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Pharmaceutical compositions of C-terminally truncated interferon with enhanced biological activity may also be formulated for delivery by inhalation, such as via a nebulizer, an inhaler, or dry powder dispersion devices. Such pulmonary delivery can be effective both for systemic delivery and for localized delivery to treat diseases of the lungs. Several companies, such as Inhale Therapeutic Systems (San Carlos, Calif.) and Alkermes (Cambridge, Mass.), have developed drug formulations suitable for inhalation. One example of a process for preparing compositions suitable for pulmonary delivery is provided in U.S. Pat. No. 6,592,904.

Also contemplated is a method for treating interferon-affected diseases comprising administering to a patient a therapeutically effective amount of a C-terminally truncated interferon with enhanced biological activity. A "therapeutically effective amount" refers to an amount effective, at dosages and for periods of time necessary, to achieve the desired therapeutic result, such as reduction of viral load or slowing or stopping the proliferation of cancer cells. In one embodiment, a therapeutically effective amount comprises 5-20 μg.

The method of administration can be any suitable method that effectively alleviates the particular interferon-affected disease being treated. Possible methods of administration are subcutaneous, intramuscular, oral, by inhalation, rectal, parenteral, enterical, transdermal, peritoneal, intratumoral, or intravenous.

While this invention has been described in conjunction with the specific embodiments outlined above, it is evident that many alternatives, modifications and variations will be apparent to those skilled in the art. Accordingly, the preferred embodiments of the invention, as set forth above, are intended to be illustrative, not limiting. Various changes may be made without departing from the spirit and scope of this invention.

EXAMPLES

Example 1

Cloning of Human Interferon Alpha 2a and Human Interferon Alpha 2b and Expression in *Nicotiana Benthamiana*

The human interferon alpha 2a and 2b genes were codon optimized for expression in tobacco mosaic virus (TMV) viral vectors. Overlapping synthetic oligonucleotides were designed and assembled via PCR amplification to obtain the full-length interferon sequences. To assemble human interferon alpha 2b, an assembly reaction containing 0.2 μM of each of sixteen synthetic oligonucleotides (SEQ ID NOs:3-18), was added to a PCR reaction containing 0.16 mM of each dATP, dCTP, dGGT, dTTP, 7 units Expand® Polymerase (Roche Diagnostics, Indianapolis) in 100 μL 1× Expand® Buffer and amplified by incubation at 95° C. for 2 min., 15 cycles of 95° C., 30 sec, 50° C., 30 sec., 72° C., 30 sec. followed by 5 min at 72° C. 1 μL of the above amplification product was re-amplified in a reaction containing 0.8 μM of the oligonucleotide of SEQ ID NO:3 and 0.8 μM of the oligonucleotide of SEQ ID NO:18, 0.16 mM of each dATP, dCTP, dGGT, dTTP, 1.8 units Expand® Polymerase (Roche Diagnostics, Indianapolis) in 25 μL 1× Expand® Buffer and amplified by incubation at 95° C. for 2 min., 15 cycles of 95° C., 30 sec, 50° C., 30 sec., 72° C., 30 sec. followed by 5 min at 72° C. Human interferon alpha 2a was amplified under the same conditions above except the oligonucleotide of SEQ ID NO:5 was replaced by the oligonucleotide of SEQ ID NO: 19 in the first amplification.

The amplified sequences were blunt cloned into TOPO TA cloning vector (Invitrogen, Carlsbad, Calif.) following the manufacturer's instructions. Clones with a nucleotide insert that encoded the correct protein sequence were identified. (SEQ ID NO:20 and SEQ ID NO:22 set forth the sequence of the nucleotide inserts encoding interferon alpha 2a and interferon alpha 2b, respectively.) These clones were restriction enzyme digested with Pac I and Xho I and the nucleotide inserts of SEQ ID NO:20 and SEQ ID NO:22 cloned into Pac I and Xho I prepared viral vector DN15 (SEQ ID NO:24) to create vectors LSBC 2529 (interferon alpha 2a) and LSBC 2530 (interferon alpha 2b). All viral vectors described in this "Examples" section are derived from tobacco mosaic virus. The native signal peptide sequence, which has the amino acid sequence MALTFALLVALLVLSCKSSCSVG (residues −23-−1 of SEQ ID NO:21 or of SEQ ID NO:23), was used to direct the interferon protein to the secretory pathway, with mature interferon alpha protein containing 165 amino acids.

Infectious transcripts were synthesized in vitro from vectors LSBC 2529 and LSBC 2530 using the mMessage mMachine® T7 kit (Ambion, Austin, Tex.) following the manufacturers directions. Briefly, a 20 µL reaction containing 2 µL 10× Reaction buffer, 10 µL 2× NTP/CAP mix, 2 µL Enzyme mix and 4 µL plasmid was incubated at 37° C. for 1 hour. The synthesized transcripts were encapsidated in a 200 µL reaction containing 0.1 M $Na_2HPO_4$-$NaH_2PO_4$ (pH 7.0), 0.5 mg/mL purified U1 coat protein (LSBC, Vacaville, Calif.) which was incubated overnight at room temperature. 200 µL of FES (0.1 M Glycine, 60 mM $K_2HPO_4$, 22 mM $Na_2P_2O_7$, 10 g/L Bentonite, 10 g/L Celite® 545) was added to each encapsidated transcript. The encapsidated transcript from each individual clone was used to inoculate two 23 day post sow *Nicotiana benthamiana* plants (Dawson, W O et al. (1986) Proc. Natl. Acad Sci. USA 83:1832-1836).

Systemically infected tissue was harvested at 10 days post inoculation and protein extracted by either homogenization in 50 mM Na Acetate, 2 mM EDTA, 0.04% sodium metabisulfite, 0.86M NaCl, pH 5.0 buffer or vacuum infiltration in 50 mM Na Acetate, 2 mM EDTA, 0.04% sodium metabisulfite, 0.86M NaCl, pH 5.0 buffer or vacuum infiltration in 50 mM Tris-HCl, 2 mM EDTA pH 7.5. The protein extracts were analyzed by Coomassie stained SDS-PAGE gel and western blot of proteins separated by SDS PAGE gel and transferred to membrane which was probed with rabbit anti-human interferon alpha sera (PBL Biomedical Laboratories, New Brunswick, N.J.). The interferon protein was found to accumulate at low levels with a significant amount of the interferon protein being degraded when extracted by vacuum infiltration or homogenization with buffer.

Example 2

Cloning of Human Interferon Alpha 2a and Human Interferon Alpha 2b with a KDEL C-terminal Extension and Expression in *Nicotiana benthamiana*

Modified interferon alpha 2a and 2b sequences were designed to modify the sub-cellular localization of the expressed interferon which was directed to the secretory pathway by its native signal peptide and secreted into the interstitial fluid. To accomplish the modified localization of the newly expressed proteins, a C-terminal extension encoding the amino acids K-D-E-L was fused to the mature interferon sequences of alpha 2a and alpha 2b. The addition of the K-D-E-L is predicted to retain the protein in the endoplasmic reticulum of the secretory pathway. 1 µL of the assembly reaction described in Example 1 above was re-amplified in a reaction containing 50 µM of the oligonucleotide of SEQ ID NO:3 and 50 µM of the oligonucleotide of SEQ ID NO:25, 0.16 mM of each dATP, dCTP, dGGT, dTTP, 1.8 units Expand® Polymerase (Roche Diagnostics, Indianapolis) in 25 µL 1× Expand® Buffer and amplified by incubation at 95° C. for 2 min., 15 cycles of 95° C., 30 sec, 50° C., 30 sec., 72° C., 30 sec. followed by 5 min at 72° C. The amplified sequences were blunt cloned into TOPO TA cloning vector (Invitrogen, Carlsbad, Calif.) following the manufacturer's instructions. Clones which encoded the correct protein sequence were restriction enzyme digested with Pac I and Xho I and cloned into Pac I and Xho I prepared viral vector DN15 (SEQ ID NO:24) to create a C-terminal extension encoding the amino acids K-D-E- L fused to the mature interferon sequences of alpha 2a and alpha 2b to create vectors LSBC 2542 and LSBC 2544, respectively.

Encapsidated in vitro transcripts of these vectors were prepared as described above in Example 1 and used to infect *Nicotiana benthamiana* plants. Systemically infected tissue was harvested and protein extracted by homogenization in buffer with buffer. The protein extracts were analyzed by Coomassie stained SDS-PAGE gel. The interferon protein was found to accumulate at very high levels with the majority of the interferon protein being mature interferon containing the carboxy terminal KDEL (SEQ ID NO:64) sequence and interferon protein containing truncations at the carboxy terminus. The resulting protein was purified and determined to have anti-proliferative activity comparable to reference standards, as indicated in Example 4, below.

Example 3

Cloning of Human Interferon Alpha 2a and Human Interferon Alpha 2b with an Extensin Signal Peptide and Expression in *Nicotiana benthamiana*

The interferon alpha 2a and human interferon alpha 2b sequences were also modified by replacing the native interferon signal peptide sequence with the *Nicotiana benthamiana* extensin signal peptide sequence to direct the protein to the plant cell secretory pathway. The *Nicotiana benthamiana* extensin signal peptide sequence was assembled in a 25 µL reaction containing 0.8 µM each of synthetic oligonucleotides PacIexSP5' (SEQ ID NO:26), EXIFNaSOE3' (SEQ ID NO:27) and KP111 (SEQ ID NO:28), 0.16 mM of each dATP, dCTP, dGGT, dTTP, 1.8 units Expand® Polymerase (Roche Diagnostics, Indianapolis) in 25 µL 1× Expand® Buffer. The human interferon alpha 2a and 2b sequences were amplified in separate reactions from plasmid DNA LSBC 2529 and LSBC 2530, respectively. 25 µL reactions contained 0.03 µL plasmid DNA, 0.8 µM each of synthetic oligonucleotides EXIFNaSOE5' (SEQ ID NO:29) and the oligonucleotide of SEQ ID NO:18, 0.16 mM of each dATP, dCTP, dGGT, dTTP, 1.8 units Expand® Polymerase (Roche Diagnostics, Indianapolis) in 25 µL 1× Expand® Buffer. The signal peptide and interferon genes reactions were incubated at 95° C. for 2 min., 15 cycles of 95° C., 30 sec, 55° C., 30 sec., 72° C., 30 sec. followed by 5 min at 72° C. The amplified signal peptide sequence and the amplified interferon alpha 2a and 2b sequences were joined by PCR amplification. Separate reactions for interferon 2a and 2b containing 0.03 µL of amplified signal sequence, 0.03 µL amplified interferon sequence, 0.8 µM each of synthetic oligonucleotides PacIexSP5' (SEQ ID NO:26) and the oligonucleotide of SEQ ID NO:18, 0.16 mM of each dATP, dCTP, dGGT, dTTP, 1.8 units Expand® Polymerase (Roche Diagnostics, Indianapolis) in 25 µL 1× Expand® Buffer were incubate as described above. The amplified extensin/interferon fusion genes (SEQ ID NO:30 for interferon alpha 2a and SEQ ID NO:32 for interferon alpha 2b) were restriction enzyme digested with Pac I and Xho I and cloned into Pac I and Xho I prepared viral vector DN15 (SEQ ID NO:24) to create LSBC 2722 and LSBC 2723.

Encapsidated in vitro transcripts of vectors LSBC 2722 and LSBC 2723 were prepared as described above and used to infect *Nicotiana benthamiana* plants. Systemically infected tissue was harvested and protein extracted by either homogenization in buffer or by vacuum infiltration with buffer. The protein extracts were analyzed by Coomassie stained SDS-PAGE gel. The interferon protein was obtained predominantly in the homogenate and the protein accumulated at a significantly higher levels than observed with the native signal and less degradation was observed.

In order to reduce the level of carboxy terminal interferon truncations present in the plant homogenate, the harvested tissue was pre-treated by vacuum infiltration with buffer to remove the majority of truncated species based on the ability to fractionate them from the full-length species by buffer infiltration and centrifugation. The protein containing buffer removed by centrifugation was discarded as it contained predominantly truncated human proteins. Extraction of the predominantly full-length interferon product and a smaller amount of truncated human proteins was accomplished by homogenization of infected material followed by pH adjustment to 4.5 to 5.2 in order to remove the fraction 1 proteins and resulted in a substantial degradation of the interferon protein. Homogenization of the plant material in a buffer that maintained the extract pH at or above 7.0 followed by a rapid adjustment of the pH to less than 3.0, preferably 2.0, resulted in a significant reduction in degradation and recovery of predominantly full-length mature interferon alpha. The acidified extract was centrifuged to remove insoluble proteins and the supernatant adjusted to pH 7.0. Virus was removed by precipitation with polyethylene glycol or ammonium sulfate and pelleted by centrifugation. The resulting interferon-containing supernatant was diafiltered to remove small molecules. If diafiltration was not performed, a significant amount of the interferon product was modified in process to contain an additional 164 Daltons of mass. The diafiltered material was applied to a Q-Sepharose column and the interferon-containing fractions pooled and applied to a Blue-sepharose column. The ethylene glycol gradient results in a separation of smaller interferon species and full-length interferon species such that fractions containing predominantly full-length interferon were pooled, concentrated and diafiltered into PBS. MALDI-TOF analysis was used to verify the mass of the purified interferon.

Example 4

Evaluation of Biological Activity of Modified Interferon

The anti-proliferative activity of the purified interferons was evaluated in Daudi cells (human B lymphoblast, derived from Burkitt's lymphoma), purchased from ATCC (CCL-213, Manassas, Va.). The cells were grown in RPMI 1640 supplemented with 10% fetal calf serum, 2 mM Glutamax®, 100 U/ml penicillin, and 100 µg/ml streptomycin. All items for the growth medium were purchased from Invitrogen (Carlsbad, Calif.). All cultures were incubated at 37° C. in a humidified atmosphere containing 5% $CO_2$. Daudi cells in exponential growth phase were counted by hemacytometer and viability was assessed by trypan blue exclusion (Sigma, St. Louis, Mo.). Cells were plated in 96-well flat-bottom plates at $2 \times 10^4$ cells/well. Cells were then incubated with test compounds (5 different concentrations, in triplicate) or medium control for 72 hours. During the final 6 hours of culture, $^3$H-thymidine was added at 1 µCi/well. Cells were harvested onto glass fiber mats using a Tomtec® Harvester 96 (Tomtec®, Orange, Conn.), and uptake of $^3$H-thymidine was measured on a Betaplate 1205 liquid scintillation counter (Wallac Instruments, Gaithersburg, Md.). To evaluate the antiproliferative activity of each compound, the counts per minute (cpm) data were converted to a percentage of the control value by the following formula: Percent Control=100×[(Mean cpm of test wells)/(Mean of medium control wells)]. The $EC_{50}$ for each test compound was determined by linear regression analysis of the linear portion of the inhibition curve.

In Tables 1, 2, 6 and 7 below, WHO IFNa refers to the World Health Organization recombinant interferon alpha; rhIFNa2A lot 0404132722 refers to purified recombinant interferon alpha 2a (mainly full-length with some truncated interferon impurities) produced as described above in plants via LSBC 2722 (the plasmid containing the extensin/interferon alpha 2a fusion gene); rhIFNa2B lot 0403192723 refers to purified recombinant interferon alpha 2b (mainly full-length with some truncated interferon impurities) produced as described above via LSBC 2723 (the plasmid containing the extensin/interferon alpha 2b fusion gene); rhkIFNa2A KDELlot 0401272542 refers to purified recombinant interferon alpha 2a (mainly full-length containing the carboxy terminal KDEL (SEQ ID NO:64) with some truncated interferon impurities) produced in plants as described above via LSBC 2544 (the plasmid containing the interferon alpha 2a-KDEL fusion gene), and rhkIFNa2B KDEL lot 0401202544 refers to purified recombinant interferon alpha 2b (mainly full-length containing the carboxy terminal KDEL (SEQ ID NO:64) with some truncated interferon impurities) produced in plants via LSBC 2544 (the plasmid containing the interferon alpha 2b-KDEL fusion gene).

TABLE 1

Interferon Antiproliferative Activity

|  | Unitage (IU) | Weight (ng) | Avg. EC50 (pg/mL) |
|---|---|---|---|
| WHO IFNa 2a control | 63000 | 250 | 5.28 |
| rhIFNa2A lot 0404132722 |  |  | 5.61 |
| WHO IFNa 2b control | 70000 | 500 | 6.39 |
| rhIFNa2B lot 0403192723 |  |  | 5.23 |
| WHO IFNa 2a control | 63000 | 250 | 9.81 |
| rhkIFNa2A KDELlot 0401272542 |  |  | 17.08 |
| WHO IFNa 2b control | 70000 | 500 | 15.45 |
| rhkIFNa2B KDEL lot 0401202544 |  |  | 17.44 |

As shown in Table 1, the interferon species, including mature (full-length), C-terminally truncated interferon impurities (mainly interferon with 161 amino acids, referred to herein as IFN-Δ4 protein) and C-terminal KDEL (SEQ ID NO:64) interferon proteins all have anti-proliferative activity comparable to the reference controls.

The antiviral activity of the purified interferon was evaluated by cytopathic effect inhibition assay (Rubinstein, S., Familletti, P. C. and Pestka, S. 1981. J Virol. 37, 755-758; Famelletti, P. C., Rubinstein, S., and Pestka, S. 1981. Methods in Enzymology, (S. Petska ed.) Academic Press, New York, 78, 387-394. In this antiviral assay for interferon, one unit per milliliter of interferon is the quantity necessary to produce a cytopathic effect of 50% with Vesicular stomatitis virus (VSV) in H226 cells . Samples were assayed in duplicate using human IFN-alpha2 (NIH reference material Gxa01-901-535).

TABLE 2

Interferon Antiviral Activity

|  | Concentration (mg/mL) | Mean Value (units/mL) | Specific Activity (units/mg) |
|---|---|---|---|
| rhIFNa2A lot 0404132722 | 1 | $4.96 \times 10e8$ | $4.96 \times 10e8$ |
| WHO IFNa 2a reference | $250 \times 10e-6$ | $7.94 \times 10e4$ | $3.18 \times 10e8$ |
| rhIFNa2B lot 0403192723 | 1 | $4.96 \times 10e8$ | $4.96 \times 10e8$ |
| WHO IFNa 2b reference | $500 \times 10e-6$ | $1.59 \times 10e5$ | $3.18 \times 10e8$ |

As shown in Table 2 above, the interferon species, which include full-length interferon and C-terminally truncated interferon impurities (mainly interferon with 161 amino acids, referred to herein as IFN-Δ4) all have anti-viral activity comparable to the reference controls.

Table 3, below, summarizes the properties of purified interferon produced from the various plasmids described above. The plasmid from which the interferon was produced is listed in parentheses below the composition in the table below.

TABLE 3

Comparison of Recombinant IFN properties

| Composition | Yield | Proteolytic Sensitivity | Activity | Other Human Proteins |
|---|---|---|---|---|
| Native IFN (2529, 2530) | +/− | +++++ | | IFN-Δ4, other C-term truncations |
| Extensin IFN (2722, 2723) | +++ | ++ | ++++ | IFN-Δ4, other C-term truncations |
| Native IFN-KDEL (2542, 2544) | ++++ | + | ++++ | other C-term truncations |

Example 5

Cloning of C-Terminally Truncated Interferon Alpha and Expression in *Nicotiana Benthamiana*

In order to reduce the level of heterogeneity in the interferon product, a series of interferon genes encoding carboxy terminal deletions were designed and constructed. Genes encoding carboxy truncated interferons were generated by PCR amplification of the LSBC 2723 plasmid using synthetic oligonucleotide PacIexSP5' (SEQ ID NO: 26) and oligonucleotides (SEQ ID NOs: 34-43) shown below that were designed to delete the codons for the indicated C-terminal amino acids, followed immediately by a translation termination codon and a restriction enzyme suitable for cloning into the expression vector. The amplified C-terminally truncated interferon nucleotide sequences (SEQ ID NO:44, 46, 48, 50, 52, 54, 56, 58, 60 and 62) were restriction enzyme digested with Pac I and Xho I and cloned into Pac I and Xho I prepared viral vector DN15 (SEQ ID NO:24) to create plasmids IFN-Δ1 through IFN-Δ10, which were then sequenced verified. The nucleotide sequence of each amplified C-terminally truncated interferon and the corresponding amino acid sequence are provided in the Sequence Listing, as summarized in Table 4 below.

TABLE 4

| Insert | Nucleotide Sequence | Amino Acid Sequence |
|---|---|---|
| IFN-Δ1 Insert | SEQ ID NO: 44 | SEQ ID NO: 45 |
| IFN-Δ2 Insert | SEQ ID NO: 46 | SEQ ID NO: 47 |
| IFN-Δ3 Insert | SEQ ID NO: 48 | SEQ ID NO: 49 |
| IFN-Δ4 Insert | SEQ ID NO: 50 | SEQ ID NO: 51 |
| IFN-Δ5 Insert | SEQ ID NO: 52 | SEQ ID NO: 53 |
| IFN-Δ6 Insert | SEQ ID NO: 54 | SEQ ID NO: 55 |
| IFN-Δ7 Insert | SEQ ID NO: 56 | SEQ ID NO: 57 |
| IFN-Δ8 Insert | SEQ ID NO: 58 | SEQ ID NO: 59 |
| IFN-Δ9 Insert | SEQ ID NO: 60 | SEQ ID NO: 61 |
| IFN-Δ10 Insert | SEQ ID NO: 62 | SEQ ID NO: 63 |

Listed below for each C-terminally truncated interferon nucleotide insert are the sequence of the 3' PCR amplification primers designed to delete the codons for C-terminal amino acids 1-10, the corresponding 3' coding region for the truncated interferon insert, and the sequence of the carboxy terminus of the truncated interferon. In the identifier, IFN-ΔX, "X" identifies the number of C-terminal amino acid residues removed from the full-length interferon.

```
IFN-Δ1 Insert
Primer:            5' GTGCTCGAGTCATTTAGAACGTAAACTTTCTTGC 3'      (SEQ ID NO: 34)

3'coding region:   G CAA GAA AGT TTA CGT TCT AAA TGA CTCGAGCAC
                   (nucleotides #556-589 of SEQ ID NO: 44))

Carboxy terminus:  Q E S L R S K *                              (Xho I)
                   (residues #158-164 of SEQ ID NO: 45)

IFNΔ2 Insert
Primer:            5' GTGCTCGAGTCAAGAACGTAAACTTTCTTGCAAG 3'      (SEQ ID NO: 35)

3'coding region:   C TTG CAA GAA AGT TTA CGT TCT TGA CTCGAGCAC
                   (nucleotides #553-586 of SEQ ID NO: 46)

Carboxy terminus:  L Q E S L R S *                              (Xho I)
                   (residues #157-163 of SEQ ID NO: 47)

IFNΔ3 Insert
Primer:            5' GTGCTCGAGTCAACGTAAACTTTCTTGCAAGTTAG 3'     (SEQ ID NO: 36)

3'coding region:   CT AAC TTG CAA GAA AGT TTA CGT TGA CTCGAGCAC
                   (nucleotides #550-583 of SEQ ID NO: 48)

Carboxy terminus:  N L Q E S L R *                              (Xho I)
                   (residues #156-162 of SEQ ID NO: 49)

IFNΔ4 Insert
Primer:            5' GTGCTCGAGTCATAAACTTTCTTGCAAGTTAGTAG 3'     (SEQ ID NO: 37)

3'coding region:   CT ACT AAC TTG CAA GAA AGT TTA TGA CTCGAGCAC
                   (nucleotides #547-580 of SEQ ID NO: 50)

Carboxy terminus:  T N L Q E S L *                              (Xho I)
                   (residues #155-161 of SEQ ID NO: 51)
```

-continued

```
IFNΔ5 Insert
Primer:            5' GTGCTCGAGTCAACTTTCTTGCAAGTTAGTAGAAAG 3'    (SEQ ID NO: 38)

3'coding region:   CTT TCT ACT AAC TTG CAA GAA AGT TGA CTCGAGCAC
                   (nucleotides #544-577 of SEQ ID NO: 52)

Carboxy terminus:  L S T N L Q E S *                              (Xho I)
                   (residues #154-160 of SEQ ID NO: 53)

IFNΔ6 Insert
Primer:            5' GTGCTCGAGTCATTCTTGCAAGTTAGTAGAAAGAC 3'      (SEQ ID NO: 39)

3'coding region:   GT CTT TCT ACT AAC TTG CAA GAA TGA CTCGAGCAC
                   (nucleotides #541-574 of SEQ ID NO: 54)

Carboxy terminus:  L S T N L Q E *                                (Xho I)
                   (residues #153-159 of SEQ ID NO: 55)

IFNΔ7 Insert
Primer:            5' GTGCTCGAGTCATTGCAAGTTAGTAGAAAGACTG 3'       (SEQ ID NO: 40)

3'coding region:   C AGT CTT TCT ACT AAC TTG CAA TGA CTCGAGCAC
                   (nucleotides #538-571 of SEQ ID NO: 56)

Carboxy terminus:  S L S T N Q *                                  (Xho I)
                   (residues #152-158 of SEQ ID NO: 57)

IFNΔ8 Insert
Primer:            5' GTGCTCGAGTCACAAGTTAGTAGAAAGACTGAAAG 3'      (SEQ ID NO: 41)

3'coding region:   CT TTC AGT CTT TCT ACT AAC TTG TGA CTCGAGCAC
                   (nucleotides #535-568 of SEQ ID NO: 58)

Carboxy terminus:  F S L S T N L *                                (Xho I)
                   (residues #151-157 of SEQ ID NO: 59)

IFNΔ9 Insert
Primer:            5' GTGCTCGAGTCAGTTAGTAGAAAGACTGAAAGATC 3'      (SEQ ID NO: 42)

3'coding region:   GA TCT TTC AGT CTT TCT ACT AAC TGA CTCGAGCAC
                   (nucleotides #532-565 of SEQ ID NO: 60)

Carboxy terminus:  S F S L S T N *                                (Xho I)
                   (residues #150-156 of SEQ ID NO: 61)

IFNΔ10 Insert
Primer:            5' GTGCTCGAGTCAAGTAGAAAGACTGAAAGATCTC 3'       (SEQ ID NO: 43)

3'coding region:   G AGA TCT TTC AGT CTT TCT ACT TGA CTCGAGCAC
                   (nucleotides #529-562 of SEQ ID NO: 62)

Carboxy terminus:  R S F S L S T *                                (Xho I)
                   (residues #149-155 of SEQ ID NO: 63)
```

Encapsidated in-vitro transcripts of vectors IFN-Δ1, IFN-Δ2, IFN-Δ3, IFN-Δ4, IFN-Δ5, IFN-Δ6, IFN-Δ7, IFN-Δ8, and IFN-Δ9 were prepared as described above and used to infect *Nicotiana benthamiana* plants. Plasmid-containing vectors with the IFN-Δ10 were not identified and IFN-Δ10 was not further evaluated. Systemically infected tissue was harvested and protein extracted by homogenization in buffer containing 50 mM Tris-HCl, 2 mM PMFS, 0.1% sodium metabisulfite and 10 mM EDTA, pH 8.3. The protein extracts were analyzed by Coomassie stained SDS-PAGE gel, as shown in FIG. 2. The various C-terminal truncations were evaluated for product accumulation and homogeneity as determined by accumulation of a single, predominant, product band. IFN-Δ2, IFN-Δ3, IFN-Δ7, IFN-Δ8 and IFN-Δ9 were selected for further purification and evaluation based on the above criteria.

The IFN-Δ2, IFN-Δ3, IFN-Δ7, IFN-Δ8 and IFN-Δ9 products were extracted by homogenization of infected material such that the extract pH was above 7.0 followed by pH adjustment to 2.0 and centrifugation to remove the fraction 1 proteins. The supernatant was pH adjusted to 7.2 and PEG precipitation and differential centrifugation was performed to separate the viral vector from the interferon protein. The resulting interferon containing supernatant was diluted with water, applied to a Q-Sepharose column and the interferon containing fractions pooled, concentrated and diafiltered into PBS.

Alternatively, the IFN-Δ7 and IFN-Δ8 products were extracted by homogenization of infected material such that the extract pH was above 7.0 followed by pH adjustment to 2.0, subsequently adjusted to 5.0 and centrifuged to remove the fraction 1 proteins. The resulting interferon containing supernatant was diluted with water, applied to a SP-Sepharose column and the interferon containing fractions pooled, concentrated and diafiltered into PBS. The C-terminally truncated interferon proteins were purified by SP-Sepharose chromatography at pH 4.0 to 5.0 as they were less susceptible to carboxy terminal truncations at this pH range. Yields of IFN-Δ7 and IFN-Δ8 purified by this process, as compared to yields of the full length interferon proteins, which were purified by a more complex process, are shown in Table 5, below. The protein identified as IFNa2B(2732), below, refers to full-length interferon protein purified from plants infected with transcripts from viral vector LSBC 2723.

TABLE 5

| Protein | Yield fw | Purity | Process |
|---|---|---|---|
| IFNd7 | 71 mg/kg | 98% | SP, blue |
| IFNd8 | 56 mg/kg | 98% | SP, blue |
| IFNa2B(2723) | 23 mg/kg | 96%, 100% | PEG, Q, blue |

The purified C-terminally truncated interferons were analyzed by Coomassie stained SDS-PAGE gel, shown in FIG. 3, and MALDI-TOF analysis was used to verify the mass of the interferons. The IFN-Δ7, IFN-Δ8 and IFN-Δ9 proteins had significantly reduced to undetectable heterogeneity at their carboxy termini.

Example 6

Biological Activity of C-Terminally Truncated Interferon

The anti-proliferative activity of the purified truncated interferon products was evaluated in Daudi cells (human B lymphoblast, derived from Burkitt's lymphoma), purchased from ATCC (CCL-213, Manassas, Va.). The cells were grown in RPMI 1640 supplemented with 10% fetal calf serum, 2 mM Glutamax®, 100 U/ml penicillin, and 100 μg/ml streptomycin. All items for the growth medium were purchased from Invitrogen (Carlsbad, Calif.). All cultures were incubated at 37° C. in a humidified atmosphere containing 5% $CO_2$. Daudi cells in exponential growth phase were counted by hemacytometer and viability was assessed by trypan blue exclusion (Sigma, St. Louis, Mo.). Cells were plated in 96-well flat-bottom plates at $2 \times 10^4$ cells/well. Cells were then incubated with test compounds (5 different concentrations, in triplicate) or medium control for 72 hours. During the final 6 hours of culture, $^3$H-thymidine was added at 1 μCi/well. Cells were harvested onto glass fiber mats using a Tomtec® Harvester 96 (Tomtec®, Orange, Conn.), and uptake of $^3$H-thymidine was measured on a Betaplate 1205 liquid scintillation counter (Wallac Instruments, Gaithersburg, Md.).

To evaluate the antiproliferative activity of each compound, each sample was assayed in triplicate and the counts per minute (cpm) data were converted to a percentage of the control value by the following formula: Percent Control=100×[(Mean cpm of test wells)/(Mean of medium control wells)] The $EC_{50}$ for each test compound was determined by linear regression analysis of the linear portion of the inhibition curve.

The IFN-Δ7, IFN-Δ8 and IFN-Δ9 proteins have anti-proliferative activity that is 207%, 191% and 154% of the WHO IFN alpha 2b reference, respectively, and 151%, 139% and 112% of the full length rhIFNa2B, respectively. Therefore these C-terminally truncated interferon alpha 2b have anti-proliferative activity that is enhanced compared to one or both of the reference controls.

TABLE 6

Interferon Antiproliferative Activity

|  | Size (a.a.) | Unitage (IU) | Weight (ng) | Spec. Activity (IU/ng) | Spec. Activity as % WHO ref | Spec. Activity as % 2723 ref |
|---|---|---|---|---|---|---|
| IFN-Δ7 | 158 | | | 290 | 207% | 151% |
| IFN-Δ8 | 157 | | | 267 | 191% | 139% |
| IFN-Δ9 | 156 | | | 216 | 154% | 112% |
| WHO IFNa 2b control | 165 | 70000 | 500 | 140 | 100% | 73% |
| rhIFNa2B lot 0403192723 | 165 | | | 192 | 137% | 100% |

The antiviral activity of the purified IFN-Δ7, IFN-Δ8 and IFN-Δ9 C-terminally truncated interferon proteins was evaluated by cytopathic effect inhibition assay (Rubinstein, S., Familletti, P. C. and Pestka, S. 1981. J Virol. 37, 755-758; Famelletti, P. C., Rubinstein, S., and Pestka, S. 1981). Methods in Enzymology, (S. Petska ed.) Academic Press, New York, 78, 387-394. In this antiviral assay for interferon, one unit per milliliter of interferon is the quantity necessary to produce a cytopathic effect of 50% with Vesicular stomatitis virus (VSV) in MDBK cells. Samples were assayed in duplicate using human interferon alpha2 (NIH reference material Gxa01-901-535).

TABLE 7

Interferon Antiviral Activity

|  | Concentration (mg/mL) | Mean Value (units/mL) | Specific Activity (units/mg) |
|---|---|---|---|
| IFN-Δ7 | 1.28 | 4.65 × 10e8 | 3.63 × 10e8 |
| IFN-Δ8 | 0.77 | 2.33 × 10e4 | 3.03 × 10e8 |
| IFN-Δ9 | 0.171 | 5.82 × 10e7 | 3.40 × 10e8 |
| rhIFNa2B lot 0403192723 | 1 | 4.96 × 10e8 | 4.96 × 10e8 |
| WHO IFNa 2b reference | 500 × 10e-6 | 1.59 × 10e5 | 3.18 × 10e8 |

The interferon species including native, IFN-Δ7, IFN-Δ8 and IFN-Δ9 carboxy terminal truncations all have anti-viral activity comparable to the reference controls.

Deposit Information

The following plasmids were deposited under the terms of the Budapest Treaty with the American Type Culture Collection, 10801 University Blvd., Manassas, Va. 20110-2209, USA (ATCC):

Plasmid DNA IFN-Δ1 is Patent Deposit ATCC PTA-6817, deposited Jun. 29, 2005.
Plasmid DNA IFN-Δ7 is Patent Deposit ATCC PTA-6818, deposited Jun. 29, 2005.
Plasmid DNA IFN-Δ8 is Patent Deposit ATCC PTA-6819, deposited Jun. 29, 2005.

These deposits were made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit or 5 years after the last request, whichever is later. The assignee of the present application has agreed that if a culture of the materials on deposit should be found nonviable or be lost or destroyed, the materials will be promptly replaced on notification with another of the same. Availability of the deposited material is not to be construed as a license to practice the invention in contravention of the rights granted under the authority of any government in accordance with its patent laws, or as a license to use the deposited material for research.

Accordingly, the present invention has been described with some degree of particularity directed to the preferred embodiment of the present invention. It should be appreciated, though, that the present invention is defined by the following claims construed in light of the prior art so that modifications or changes may be made to the preferred embodiment of the present invention without departing from the inventive concepts contained herein.

What is claimed is:

1. An artificial polynucleotide encoding a polypeptide comprising a C-terminally truncated interferon having enhanced anti-proliferative activity as compared to full length interferon, wherein said C-terminally truncated interferon consists of amino acids 1-156 of SEQ ID NO:2.

2. The artificial polynucleotide of claim 1 further comprising a nucleotide sequence that encodes the amino acid sequence of an extensin signal peptide.

3. The artificial polynucleotide of claim 1, wherein said polynucleotide comprises a fragment of SEQ ID NO: 1 consisting of nucleotides 1-468.

4. A host plant cell comprising an expression vector wherein said vector comprises an artificial polynucleotide encoding a polypeptide comprising a C-terminally truncated interferon having enhanced anti-proliferative activity as compared to full length interferon, wherein said C-terminally truncated interferon consists of amino acids 1-156 of SEQ ID NO:2.

5. A process for producing a polypeptide comprising a C-terminally truncated interferon having enhanced anti-proliferative activity as compared to full length interferon; said process comprising transforming a plant with an expression vector wherein said vector comprises an artificial polynucleotide encoding a polypeptide comprising said C-terminally truncated interferon, wherein said C-terminally truncated interferon consists of amino acids 1-156 of SEQ ID NO:2.

6. The process of claim 5 comprising infecting the plant with a viral vector comprising the expression vector.

7. The process of claim 5 wherein the expression vector further comprises a nucleotide sequence that encodes the amino acid sequence of an extensin signal peptide.

8. The process of claim 5 comprising stably incorporating the expression vector into the genome of the plant.

9. A plant comprising an expression vector wherein said vector comprises an artificial polynucleotide encoding a polypeptide comprising a C-terminally truncated interferon having enhanced anti-proliferative activity as compared to full-length interferon, wherein said C-terminally truncated interferon consists of amino acids 1-156 of SEQ ID NO:2.

10. The plant of claim 9 wherein the expression vector is a viral vector.

11. The plant of claim 9 wherein the expression vector is stably incorporated into the plant genome.

* * * * *

SEQUENCE LISTING

```
<160> NUMBER OF SEQ ID NOS: 64

<210> SEQ ID NO 1
<211> LENGTH: 495
<212> TYPE: DNA
<213> ORGANISM: Homo sapiens
<220> FEATURE:
<221> NAME/KEY: CDS
<222> LOCATION: (1)..(495)

<400> SEQUENCE: 1 tgc gac tta cca caa act cac agc ctt ggt agt agg aga acg ttg atg         48
Cys Asp Leu Pro Gln Thr His Ser Leu Gly Ser Arg Arg Thr Leu Met
1               5                   10                  15 tta ttg gcg cag atg agg aga ata tct tta ttc tct tgt ttg aag gat         96
Leu Leu Ala Gln Met Arg Arg Ile Ser Leu Phe Ser Cys Leu Lys Asp
            20                  25                  30 aga cat gac ttc gga ttt cca caa gag gaa ttt ggt aat caa ttc caa        144
Arg His Asp Phe Gly Phe Pro Gln Glu Glu Phe Gly Asn Gln Phe Gln
        35                  40                  45 aag gct gaa act ata cct gta tta cat gag atg ata cag caa atc ttc        192
Lys Ala Glu Thr Ile Pro Val Leu His Glu Met Ile Gln Gln Ile Phe
    50                  55                  60 aat ctg ttt agc aca aaa gac tca tct gct gca tgg gac gaa act ctc        240
Asn Leu Phe Ser Thr Lys Asp Ser Ser Ala Ala Trp Asp Glu Thr Leu
65                  70                  75                  80 tta gac aaa ttc tac act gaa ttg tac caa cag ctt aat gac ttg gaa        288
Leu Asp Lys Phe Tyr Thr Glu Leu Tyr Gln Gln Leu Asn Asp Leu Glu
                85                  90                  95 gcc tgt gtg ata cag gga gtg ggt gta acg gag act cca ttg atg aag        336
Ala Cys Val Ile Gln Gly Val Gly Val Thr Glu Thr Pro Leu Met Lys
            100                 105                 110 gag gac agc ata ctg gca gtg agg aaa tac ttc caa cga atc act tta        384
Glu Asp Ser Ile Leu Ala Val Arg Lys Tyr Phe Gln Arg Ile Thr Leu
        115                 120                 125 tac ctg aaa gag aag aaa tac tca cct tgt gcc tgg gag gtt gtc aga        432
Tyr Leu Lys Glu Lys Lys Tyr Ser Pro Cys Ala Trp Glu Val Val Arg
    130                 135                 140 gca gaa ata atg aga tct ttc agt ctt tct act aac ttg caa gaa agt        480
Ala Glu Ile Met Arg Ser Phe Ser Leu Ser Thr Asn Leu Gln Glu Ser
145                 150                 155                 160 tta cgt tct aaa gag                                                    495
Leu Arg Ser Lys Glu
                165

<210> SEQ ID NO 2
<211> LENGTH: 165
<212> TYPE: PRT
```

<213> ORGANISM: Homo sapiens

<400> SEQUENCE: 2

```
Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165
```

<210> SEQ ID NO 3
<211> LENGTH: 23
<212> TYPE: DNA
<213> ORGANISM: Artificial
<220> FEATURE:
<223> OTHER INFORMATION: synthetic oligonucleotide, see Example 1

<400> SEQUENCE: 3
gtgttaatta acaatggcac taa        23

<210> SEQ ID NO 4
<211> LENGTH: 60
<212> TYPE: DNA
<213> ORGANISM: Artificial
<220> FEATURE:
<223> OTHER INFORMATION: synthetic oligonucleotide, see Example 1

<400> SEQUENCE: 4
caagacaaca ctagcagagc aactaatagt gcgaaagtta gtgccattgt taattaacac        60

<210> SEQ ID NO 5
<211> LENGTH: 60
<212> TYPE: DNA
<213> ORGANISM: Artificial
<220> FEATURE:
<223> OTHER INFORMATION: synthetic oligonucleotide, see Example 1

<400> SEQUENCE: 5
gctctgctag tgttgtcttg taagagctca tgctctgttg gatgcgactt accacaaact        60

<210> SEQ ID NO 6
<211> LENGTH: 60
<212> TYPE: DNA
<213> ORGANISM: Artificial
<220> FEATURE:
<223> OTHER INFORMATION: synthetic oligonucleotide, see Example 1

<400> SEQUENCE: 6
gcgccaataa catcaacgtt ctcctactac caaggctgtg agtttgtggt aagtcgcatc    60

<210> SEQ ID NO 7
<211> LENGTH: 60
<212> TYPE: DNA
<213> ORGANISM: Artificial
<220> FEATURE:
<223> OTHER INFORMATION: synthetic oligonucleotide, see Example 1

<400> SEQUENCE: 7
aacgttgatg ttattggcgc agatgaggag aatatcttta ttctcttgtt tgaaggatag    60

<210> SEQ ID NO 8
<211> LENGTH: 60
<212> TYPE: DNA
<213> ORGANISM: Artificial
<220> FEATURE:
<223> OTHER INFORMATION: synthetic oligonucleotide, see Example 1

<400> SEQUENCE: 8
ttgattacca aattcctctt gtggaaatcc gaagtcatgt ctatccttca acaagagaa     60

<210> SEQ ID NO 9
<211> LENGTH: 60
<212> TYPE: DNA
<213> ORGANISM: Artificial
<220> FEATURE:
<223> OTHER INFORMATION: synthetic oligonucleotide, see Example 1

<400> SEQUENCE: 9
aagaggaatt tggtaatcaa ttccaaaagg ctgaaactat acctgtatta catgagatga    60

<210> SEQ ID NO 10
<211> LENGTH: 60
<212> TYPE: DNA
<213> ORGANISM: Artificial
<220> FEATURE:
<223> OTHER INFORMATION: synthetic oligonucleotide, see Example 1

<400> SEQUENCE: 10
gatgagtctt ttgtgctaaa cagattgaag atttgctgta tcatctcatg taatacaggt    60

<210> SEQ ID NO 11
<211> LENGTH: 60
<212> TYPE: DNA
<213> ORGANISM: Artificial
<220> FEATURE:
<223> OTHER INFORMATION: synthetic oligonucleotide, see Example 1

<400> SEQUENCE: 11
tttagcacaa aagactcatc tgctgcatgg gacgaaactc tcttagacaa attctacact    60

<210> SEQ ID NO 12
<211> LENGTH: 60
<212> TYPE: DNA
<213> ORGANISM: Artificial
<220> FEATURE:
<223> OTHER INFORMATION: synthetic oligonucleotide, see Example 1

<400> SEQUENCE: 12
tcacacaggc ttccaagtca ttaagctgtt ggtacaattc agtgtagaat tgtctaaga     60

<210> SEQ ID NO 13
<211> LENGTH: 60

```
<212> TYPE: DNA
<213> ORGANISM: Artificial
<220> FEATURE:
<223> OTHER INFORMATION: synthetic oligonucleotide, see Example 1

<400> SEQUENCE: 13
tgacttggaa gcctgtgtga tacagggagt gggtgtaacg agactccat tgatgaagga    60

<210> SEQ ID NO 14
<211> LENGTH: 60
<212> TYPE: DNA
<213> ORGANISM: Artificial
<220> FEATURE:
<223> OTHER INFORMATION: synthetic oligonucleotide, see Example 1

<400> SEQUENCE: 14
gattcgttgg aagtatttcc tcactgccag tatgctgtcc tccttcatca atggagtctc    60

<210> SEQ ID NO 15
<211> LENGTH: 60
<212> TYPE: DNA
<213> ORGANISM: Artificial
<220> FEATURE:
<223> OTHER INFORMATION: synthetic oligonucleotide, see Example 1

<400> SEQUENCE: 15
ggaaatactt ccaacgaatc actttatacc tgaaagagaa gaaatactca ccttgtgcct    60

<210> SEQ ID NO 16
<211> LENGTH: 60
<212> TYPE: DNA
<213> ORGANISM: Artificial
<220> FEATURE:
<223> OTHER INFORMATION: synthetic oligonucleotide, see Example 1

<400> SEQUENCE: 16
agactgaaag atctcattat ttctgctctg acaacctccc aggcacaagg tgagtatttc    60

<210> SEQ ID NO 17
<211> LENGTH: 60
<212> TYPE: DNA
<213> ORGANISM: Artificial
<220> FEATURE:
<223> OTHER INFORMATION: synthetic oligonucleotide, see Example 1

<400> SEQUENCE: 17
ataatgagat ctttcagtct ttctactaac ttgcaagaaa gtttacgttc taaagagtga    60

<210> SEQ ID NO 18
<211> LENGTH: 31
<212> TYPE: DNA
<213> ORGANISM: Artificial
<220> FEATURE:
<223> OTHER INFORMATION: synthetic oligonucleotide, see Example 1

<400> SEQUENCE: 18
gtgctcgagt cactctttag aacgtaaact t                                   31

<210> SEQ ID NO 19
<211> LENGTH: 60
<212> TYPE: DNA
<213> ORGANISM: Artificial
<220> FEATURE:
<223> OTHER INFORMATION: synthetic oligonucleotide, see Example 1

<400> SEQUENCE: 19
aacgttgatg ttattggcgc agatgaggaa gatatcttta ttctcttgtt tgaaggatag    60
```

<210> SEQ ID NO 20
<211> LENGTH: 583
<212> TYPE: DNA
<213> ORGANISM: Artificial
<220> FEATURE:
<223> OTHER INFORMATION: human interferon alpha 2a with restriction
     enzyme sites, see Example 1
<220> FEATURE:
<221> NAME/KEY: CDS
<222> LOCATION: (11)..(574)
<220> FEATURE:
<221> NAME/KEY: mat_peptide
<222> LOCATION: (80)..(574)

<400> SEQUENCE: 20

```
ttaattaaca atg gca cta act ttc gca cta tta gtt gct ctg cta gtg           49
           Met Ala Leu Thr Phe Ala Leu Leu Val Ala Leu Leu Val
               -20              -15 ttg tct tgt aag agc tca tgc tct gtt gga tgc gac tta cca caa act         97
Leu Ser Cys Lys Ser Ser Cys Ser Val Gly Cys Asp Leu Pro Gln Thr
-10              -5              -1  1               5 cac agc ctt ggt agt agg aga acg ttg atg tta ttg gcg cag atg agg        145
His Ser Leu Gly Ser Arg Arg Thr Leu Met Leu Leu Ala Gln Met Arg
            10              15              20 aag ata tct tta ttc tct tgt ttg aag gat aga cat gac ttc gga ttt        193
Lys Ile Ser Leu Phe Ser Cys Leu Lys Asp Arg His Asp Phe Gly Phe
        25              30              35 cca caa gag gaa ttt ggt aat caa ttc caa aag gct gaa act ata cct        241
Pro Gln Glu Glu Phe Gly Asn Gln Phe Gln Lys Ala Glu Thr Ile Pro
    40              45              50 gta tta cat gag atg ata cag caa atc ttc aat ctg ttt agc aca aaa        289
Val Leu His Glu Met Ile Gln Gln Ile Phe Asn Leu Phe Ser Thr Lys
55              60              65              70 gac tca tct gct gca tgg gac gaa act ctc tta gac aaa ttc tac act        337
Asp Ser Ser Ala Ala Trp Asp Glu Thr Leu Leu Asp Lys Phe Tyr Thr
                75              80              85 gaa ttg tac caa cag ctt aat gac ttg gaa gcc tgt gtg ata cag gga        385
Glu Leu Tyr Gln Gln Leu Asn Asp Leu Glu Ala Cys Val Ile Gln Gly
            90              95              100 gtg ggt gta acg gag act cca ttg atg aag gag gac agc ata ctg gca        433
Val Gly Val Thr Glu Thr Pro Leu Met Lys Glu Asp Ser Ile Leu Ala
        105             110             115 gtg agg aaa tac ttc caa cga atc act tta tac ctg aaa gaa aag aaa        481
Val Arg Lys Tyr Phe Gln Arg Ile Thr Leu Tyr Leu Lys Glu Lys Lys
    120             125             130 tac tca cct tgt gcc tgg gag gtt gtc aga gca gaa ata atg aga tct        529
Tyr Ser Pro Cys Ala Trp Glu Val Val Arg Ala Glu Ile Met Arg Ser
135             140             145             150 ttc agt ctt tct act aac ttg caa gaa agt tta cgt tct aaa gag             574
Phe Ser Leu Ser Thr Asn Leu Gln Glu Ser Leu Arg Ser Lys Glu
                155             160             165 tgactcgag                                                                583
```

<210> SEQ ID NO 21
<211> LENGTH: 188
<212> TYPE: PRT
<213> ORGANISM: Artificial
<220> FEATURE:
<223> OTHER INFORMATION: Synthetic Construct

<400> SEQUENCE: 21

```
Met Ala Leu Thr Phe Ala Leu Leu Val Ala Leu Leu Val Leu Ser Cys
            -20             -15             -10
```

```
Lys Ser Ser Cys Ser Val Gly Cys Asp Leu Pro Gln Thr His Ser Leu
        -5              -1   1               5
Gly Ser Arg Arg Thr Leu Met Leu Leu Ala Gln Met Arg Lys Ile Ser
 10              15                  20                  25
Leu Phe Ser Cys Leu Lys Asp Arg His Asp Phe Gly Phe Pro Gln Glu
                30                  35                  40
Glu Phe Gly Asn Gln Phe Gln Lys Ala Glu Thr Ile Pro Val Leu His
                45                  50                  55
Glu Met Ile Gln Gln Ile Phe Asn Leu Phe Ser Thr Lys Asp Ser Ser
             60                  65                  70
Ala Ala Trp Asp Glu Thr Leu Leu Asp Lys Phe Tyr Thr Glu Leu Tyr
 75                  80                  85
Gln Gln Leu Asn Asp Leu Glu Ala Cys Val Ile Gln Gly Val Gly Val
 90                  95                 100                 105
Thr Glu Thr Pro Leu Met Lys Glu Asp Ser Ile Leu Ala Val Arg Lys
                110                 115                 120
Tyr Phe Gln Arg Ile Thr Leu Tyr Leu Lys Glu Lys Lys Tyr Ser Pro
                125                 130                 135
Cys Ala Trp Glu Val Val Arg Ala Glu Ile Met Arg Ser Phe Ser Leu
                140                 145                 150
Ser Thr Asn Leu Gln Glu Ser Leu Arg Ser Lys Glu
                155                 160                 165

<210> SEQ ID NO 22
<211> LENGTH: 583
<212> TYPE: DNA
<213> ORGANISM: Artificial
<220> FEATURE:
<223> OTHER INFORMATION: human interferon alpha 2b with restriction
      enzyme sites, see Example 1
<220> FEATURE:
<221> NAME/KEY: CDS
<222> LOCATION: (11)..(574)
<220> FEATURE:
<221> NAME/KEY: mat_peptide
<222> LOCATION: (80)..(574)

<400> SEQUENCE: 22
ttaattaaca atg gca cta act ttc gca cta tta gtt gct ctg cta gtg       49
           Met Ala Leu Thr Phe Ala Leu Leu Val Ala Leu Leu Val
               -20                 -15 ttg tct tgt aag agc tca tgc tct gtt gga tgc gac tta cca caa act      97
Leu Ser Cys Lys Ser Ser Cys Ser Val Gly Cys Asp Leu Pro Gln Thr
-10              -5              -1   1               5 cac agc ctt ggt agt agg aga acg ttg atg tta ttg gcg cag atg agg     145
His Ser Leu Gly Ser Arg Arg Thr Leu Met Leu Leu Ala Gln Met Arg
            10                  15                  20 aga ata tct tta ttc tct tgt ttg aag gat aga cat gac ttc gga ttt     193
Arg Ile Ser Leu Phe Ser Cys Leu Lys Asp Arg His Asp Phe Gly Phe
        25                  30                  35 cca caa gag gaa ttt ggt aat caa ttc caa aag gct gaa act ata cct     241
Pro Gln Glu Glu Phe Gly Asn Gln Phe Gln Lys Ala Glu Thr Ile Pro
 40                  45                  50 gta tta cat gag atg ata cag caa atc ttc aat ctg ttt agc aca aaa     289
Val Leu His Glu Met Ile Gln Gln Ile Phe Asn Leu Phe Ser Thr Lys
 55                  60                  65                  70 gac tca tct gct gca tgg gac gaa act ctc tta gac aaa ttc tac act     337
Asp Ser Ser Ala Ala Trp Asp Glu Thr Leu Leu Asp Lys Phe Tyr Thr
                 75                  80                  85 gaa ttg tac caa cag ctt aat gac ttg gaa gcc tgt gtg ata cag gga     385
```

```
                 Glu Leu Tyr Gln Gln Leu Asn Asp Leu Glu Ala Cys Val Ile Gln Gly
                              90                  95                 100 gtg ggt gta acg gag act cca ttg atg aag gag gac agc ata ctg gca       433
Val Gly Val Thr Glu Thr Pro Leu Met Lys Glu Asp Ser Ile Leu Ala
             105                 110                 115 gtg agg aaa tac ttc caa cga atc act tta tac ctg aaa gag aag aaa       481
Val Arg Lys Tyr Phe Gln Arg Ile Thr Leu Tyr Leu Lys Glu Lys Lys
120                 125                 130 tac tca cct tgt gcc tgg gag gtt gtc aga gca gaa ata atg aga tct       529
Tyr Ser Pro Cys Ala Trp Glu Val Val Arg Ala Glu Ile Met Arg Ser
135                 140                 145                 150 ttc agt ctt tct act aac ttg caa gaa agt tta cgt tct aaa gag           574
Phe Ser Leu Ser Thr Asn Leu Gln Glu Ser Leu Arg Ser Lys Glu
                155                 160                 165 tgactcgag                                                             583

<210> SEQ ID NO 23
<211> LENGTH: 188
<212> TYPE: PRT
<213> ORGANISM: Artificial
<220> FEATURE:
<223> OTHER INFORMATION: Synthetic Construct

<400> SEQUENCE: 23

Met Ala Leu Thr Phe Ala Leu Leu Val Ala Leu Leu Val Leu Ser Cys
             -20                 -15                 -10

Lys Ser Ser Cys Ser Val Gly Cys Asp Leu Pro Gln Thr His Ser Leu
             -5              -1   1               5

Gly Ser Arg Arg Thr Leu Met Leu Leu Ala Gln Met Arg Arg Ile Ser
10                  15                  20                  25

Leu Phe Ser Cys Leu Lys Asp Arg His Asp Phe Gly Phe Pro Gln Glu
                30                  35                  40

Glu Phe Gly Asn Gln Phe Gln Lys Ala Glu Thr Ile Pro Val Leu His
                45                  50                  55

Glu Met Ile Gln Gln Ile Phe Asn Leu Phe Ser Thr Lys Asp Ser Ser
                60                  65                  70

Ala Ala Trp Asp Glu Thr Leu Leu Asp Lys Phe Tyr Thr Glu Leu Tyr
75                  80                  85

Gln Gln Leu Asn Asp Leu Glu Ala Cys Val Ile Gln Gly Val Gly Val
90                  95                  100                 105

Thr Glu Thr Pro Leu Met Lys Glu Asp Ser Ile Leu Ala Val Arg Lys
                110                 115                 120

Tyr Phe Gln Arg Ile Thr Leu Tyr Leu Lys Glu Lys Lys Tyr Ser Pro
                125                 130                 135

Cys Ala Trp Glu Val Val Arg Ala Glu Ile Met Arg Ser Phe Ser Leu
                140                 145                 150

Ser Thr Asn Leu Gln Glu Ser Leu Arg Ser Lys Glu
                155                 160                 165

<210> SEQ ID NO 24
<211> LENGTH: 20251
<212> TYPE: DNA
<213> ORGANISM: Artificial
<220> FEATURE:
<223> OTHER INFORMATION: viral vector DN15, see Example 1

<400> SEQUENCE: 24
gtatttttac aacaattacc aacaacaaca aacaacagac aacattacaa ttactattta     60
caattacaat ggcatacaca cagacagcta ccacatcagc tttgctggac actgtccgag    120
```

```
gaaacaactc cttggtcaat gatctagcaa agcgtcgtct ttacgacaca gcggttgaag      180
agtttaacgc tcgtgaccgc aggcccaagg tgaacttttc aaaagtaata agcgaggagc      240
agacgcttat tgctacccgg gcgtatccag aattccaaat tacattttat aacacgcaaa      300
atgccgtgca ttcgcttgca ggtggattgc gatctttaga actggaatat ctgatgatgc      360
aaattcccta cggatcattg acttatgaca taggcgggaa ttttgcatcg catctgttca      420
agggacgagc atatgtacac tgctgcatgc ccaacctgga cgttcgagac atcatgcggc      480
acgaaggcca gaaagacagt attgaactat acctttctag gctagagaga gggggaaaa      540 cagtccccaa cttccaaaag gaagcatttg acagatacgc agaaattcct gaagacgctg      600
tctgtcacaa tactttccag acatgcgaac atcagccgat gcagcaatca ggcagagtgt      660
atgccattgc gctacacagc atatatgaca taccagccga tgagttcggg gcggcactct      720
tgaggaaaaa tgtccatacg tgctatgccg ctttccactt ctccgagaac ctgcttcttg      780
aagattcatg cgtcaatttg gacgaaatca acgcgtgttt ttcgcgcgat ggagacaagt      840 tgacctttc ttttgcatca gagagtactc ttaattactg tcatagttat tctaatattc      900
ttaagtatgt gtgcaaaact tacttcccgg cctctaatag agaggtttac atgaaggagt      960
ttttagtcac cagagttaat acctggtttt gtaagttttc tagaatagat acttttcttt     1020
tgtacaaagg tgtggcccat aaaagtgtag atagtgagca gttttatact gcaatgaaag     1080
acgcatggca ttacaaaaag actcttgcaa tgtgcaacag cgagagaatc ctccttgagg     1140
attcatcatc agtcaattac tggtttccca aaatgaggga tatggtcatc gtaccattat     1200
tcgacatttc tttggagact agtaagagga cgcgcaagga agtcttagtg tccaaggatt     1260
tcgtgtttac agtgcttaac cacattcgaa cataccaggc gaaagctctt acatacgcaa     1320
atgttttgtc cttcgtcgaa tcgattcgat cgagggtaat cattaacggt gtgacagcga     1380
ggtccgaatg ggatgtggac aaatctttgt tacaatcctt gtccatgacg ttttacctgc     1440
atactaagct tgccgttcta aaggatgact tactgattag caagtttagt ctcggttcga     1500
aaacggtgtg ccagcatgtg tgggatgaga tttcgctggc gtttgggaac gcatttccct     1560
ccgtgaaaga gaggctcttg aacaggaaac ttatcagagt ggcaggcgac gcattagaga     1620
tcagggtgcc tgatctatat gtgaccttcc acgacagatt agtgactgag tacaaggcct     1680
ctgtggacat gcctgcgctt gacattagga agaagatgga agaaacggaa gtgatgtaca     1740
atgcactttc agaattatcg gtgttaaggg agtctgacaa attcgatgtt gatgtttttt     1800
cccagatgtg ccaatctttg gaagttgacc caatgacggc agcgaaggtt atagtcgcgg     1860
tcatgagcaa tgagagcggt ctgactctca catttgaacg acctactgag gcgaatgttg     1920
cgctagcttt acaggatcaa gagaaggctt cagaaggtgc attggtagtt acctcaagag     1980
aagttgaaga accgtccatg aagggttcga tggccagagg agagttacaa ttagctggtc     2040
ttgctggaga tcatccggaa tcgtcctatt ctaagaacga ggagatagag tctttagagc     2100
agtttcatat ggcgacggca gattcgttaa ttcgtaagca gatgagctcg attgtgtaca     2160
cgggtccgat taaagttcag caaatgaaaa actttatcga tagcctggta gcatcactat     2220
ctgctgcggt gtcgaatctc gtcaagatcc tcaaagatac agctgctatt gaccttgaaa     2280
cccgtcaaaa gtttggagtc ttggatgttg catctaggaa gtggttaatc aaaccaacgg     2340
ccaagagtca tgcatggggt gttgttgaaa cccacgcgag gaagtatcat gtggcgcttt     2400
tggaatatga tgagcagggt gtggtgacat gcgatgattg gagaagagta gctgttagct     2460
ctgagtctgt tgtttattcc gacatggcga aactcagaac tctgcgcaga ctgcttcgaa     2520
```

```
acggagaacc gcatgtcagt agcgcaaagg ttgttcttgt ggacggagtt ccgggctgtg   2580
gaaaaaccaa agaaattctt tccagggtta attttgatga agatctaatt ttagtacctg   2640
ggaagcaagc cgcggaaatg atcagaagac gtgcgaattc ctcagggatt attgtggcca   2700
cgaaggacaa cgttaaaacc gttgattctt tcatgatgaa ttttgggaaa agcacacgct   2760
gtcagttcaa gaggttattc attgatgaag ggttgatgtt gcatactggt tgtgttaatt   2820
ttcttgtggc gatgtcattg tgcgaaattg catatgttta cggagacaca cagcagattc   2880
catacatcaa tagagtttca ggattcccgt accccgccca ttttgccaaa ttggaagttg   2940
acgaggtgga gacacgcaga actactctcc gttgtccagc cgatgtcaca cattatctga   3000
acaggagata tgagggcttt gtcatgagca cttcttcggt taaaaagtct gtttcgcagg   3060
agatggtcgg cggagccgcc gtgatcaatc cgatctcaaa acccttgcat ggcaagatcc   3120
tgacttttac ccaatcggat aaagaagctc tgctttcaag agggtattca gatgttcaca   3180
ctgtgcatga agtgcaaggc gagacatact ctgatgtttc actagttagg ttaaccccta   3240
caccggtctc catcattgca ggagacagcc acatgttttt ggtcgcattg tcaaggcaca   3300
cctgttcgct caagtactac actgttgtta tggatccttt agttagtatc attagagatc   3360
tagagaaact tagctcgtac ttgttagata tgtataaggt cgatgcagga acacaatagc   3420
aattacagat tgactcggtg ttcaaaggtt ccaatctttt tgttgcagcg ccaaagactg   3480
gtgatatttc tgatatgcag ttttactatg ataagtgtct cccaggcaac agcaccatga   3540
tgaataattt tgatgctgtt accatgaggt tgactgacat ttcattgaat gtcaaaaatt   3600
gcatattgga tatgtctaag tctgttgctg cgcctaagga tcaaatcaaa ccactaatac   3660
ctatggtacg aacggcggca gaaatgccac gccagactgg actattggaa aatttagtgg   3720
cgatgattaa agaaactttt aacgcacccg agttgtctgg catcattgat attgaaaata   3780
ctgcatcttt ggttgtagat aagttttttg atagttattt gcttaaagaa aaagaaaac   3840 caaataaaaa tgtttctttg ttcagtagag agtctctcaa tagatggtta gaaaagcagg   3900
aacaggtaac aataggccag ctcgcagatt ttgattttgt ggatttgcca gcagttgatc   3960
agtacagaca catgattaaa gcacaaccca aacaaaagtt ggacacttca atccaaacgg   4020
agtacccggc tttgcagacg attgtgtacc attcaaaaaa gatcaatgca atattcggcc   4080
cgttgtttag tgagcttact aggcaattac tggacagtgt tgattcgagc agattttttgt   4140 ttttcacaag aaagacacca gcgcagattg aggattcctt cggagatctc gacagtcatg   4200
tgccgatgga tgtcttggag ctggatatat caaaatacga caaatctcag aatgaattcc   4260
actgtgcagt agaatacgag atctggcgaa gattgggttt cgaagacttc ttgggagaag   4320
tttggaaaca agggcataga aagaccaccc tcaaggatta taccgcaggt ataaaaactt   4380
gcatctggta tcaaagaaag agcggggacg tcacgacgtt cattggaaac actgtgatca   4440
ttgctgcatg tttggcctcg atgcttccga tggagaaaat aatcaaagga gccttttgcg   4500
gtgacgatag tctgctgtac tttccaaagg gttgtgagtt tccggatgtg caacactccg   4560
cgaatcttat gtggaatttt gaagcaaaac tgttaaaaa acagtatgga tacttttgcg   4620
gaagatatgt aatacatcac gacagaggat gcattgtgta ttacgatccc taaagttga   4680 tctcgaaact tggtgctaaa cacatcaagg attgggaaca cttggaggag ttcagaaggt   4740
ctctttgtga tgttgctgtt tcgttgaaca attgtgcgta ttacacacag ttggacgacg   4800
ctgtatggga ggttcataag accgcccctc caggttcgtt tgtttataaa agtctggtga   4860
agtatttgtc tgataaagtt cttttagaa gtttgtttat agatggctct agttgttaaa   4920
```

```
ggaaaagtga atatcaatga gtttatcgac ctgacaaaaa tggagaagat cttaccgtcg   4980
atgtttaccc gtgtaaagag tgttatgtgt tccaaagttg ataaaataat ggttcatgag   5040
aatgagtcat tgtcaggggt gaaccttctt aaaggagtta agcttattga tagtggatac   5100
gtctgtttag ccggtttggt cgtcacgggc gagtggaact tgcctgacaa ttgcagagga   5160
ggtgtgagcg tgtgtctggt ggacaaaagg atggaaagag ccgacgaggc cactctcgga   5220
tcttactaca cagcagctgc aaagaaaaga tttcagttca aggtcgttcc caattatgct   5280
ataaccaccc aggacgcgat gaaaaacgtc tggcaagttt tagttaatat tagaaatgtg   5340
aagatgtcag cgggtttctg tccgcttcct ctggagtttg tgtcggtgtg tattgtttat   5400
agaaataata taaaattagg tttgagagag aagattacaa acgtgagaga cggagggccc   5460
atggaactta cagaagaagt cgttgatgag ttcatggaag atgtccctat gtcgatcagg   5520
cttgcaaagt ttcgatctcg aaccggaaaa aagagtgatg tccgcaaagg gaaaaatagt   5580
agtagtgatc ggtcagtgcc gaacaagaac tatagaaatg ttaaggattt tggaggaatg   5640
agttttaaaa agaataattt aatcgatgat gattcggagg ctactgtcgc cgaatcggat   5700 tcgtttttaaa tagatcttac agtatcacta ctccatctca gttcgtgttc ttgtcattaa   5760
ttaaatggct agcaaaggag aagaactttt cactggagtt gtcccaattc ttgttgaatt   5820
agatggtgat gttaatgggc acaaattttc tgtcagtgga gagggtgaag gtgatgctac   5880
atacggaaag cttaccctta aatttatttg cactactgga aaactacctg ttccatggcc   5940
aacacttgtc actactttct cttatggtgt tcaatgcttt tcccgttatc cggatcatat   6000
gaaacggcat gactttttca gagtgccat gcccgaaggt tatgtacagg aacgcactat   6060
atctttcaaa gatgacggga actacaagac gcgtgctgaa gtcaagtttg aaggtgatac   6120
ccttgttaat cgtatcgagt taaaaggtat tgattttaaa gaagatggaa acattctcgg   6180
acacaaactc gagtacaact ataactcaca caatgtatac atcacggcag acaaacaaaa   6240
gaatggaatc aaagctaact tcaaaattcg ccacaacatt gaagatggat ccgttcaact   6300
agcagaccat tatcaacaaa atactccaat tggcgatggc cctgtccttt taccagacaa   6360
ccattacctg tcgacacaat ctgccctttc gaaagatccc aacgaaaagc gtgaccacat   6420
ggtccttctt gagtttgtaa ctgctgctgg gattacacat ggcatggatg agctctacaa   6480
ataatgacac tcgaggggta gtcaagatgc ataataaata acggattgtg tccgtaatca   6540
cacgtggtgc gtacgataac gcatagtgtt tttccctcca cttaaatcga agggttgtgt   6600
cttggatcgc gcgggtcaaa tgtatatggt tcatatacat ccgcaggcac gtaataaagc   6660
gaggggttcg ggtcgaggtc ggctgtgaaa ctcgaaaagg ttccggaaaa caaaaaagag   6720
agtggtaggt aatagtgtta ataataagaa ataaataat agtggtaaga aaggtttgaa   6780
agttgaggaa attgaggata atgtaagtga tgacgagtct atcgcgtcat cgagtacgtt   6840
ttaatcaata tgccttatac aatcaactct ccgagccaat tgtttactt aagttccgct   6900 tatgcagatc ctgtgcagct gatcaatctg tgtacaaatg cattgggtaa ccagtttcaa   6960
acgcaacaag ctaggacaac agtccaacag caatttgcgg atgcctggaa acctgtgcct   7020
agtatgacag tgagatttcc tgcatcggat ttctatgtgt atagatataa ttcgacgctt   7080
gatccgttga tcacggcgtt attaaatagc ttcgatacta gaaatagaat aatagaggtt   7140
gataatcaac ccgcaccgaa tactactgaa atcgttaacg cgactcagag ggtagacgat   7200
gcgactgtag ctataaggc ttcaatcaat aatttggcta atgaactggt tcgtggaact   7260
ggcatgttca atcaagcaag ctttgagact gctagtggac ttgtctggac cacaactccg   7320
```

```
gctacttagc tattgttgtg agatttccta aaataaagtc actgaagact taaaattcag   7380
ggtggctgat accaaaatca gcagtggttg ttcgtccact taaatataac gattgtcata   7440
tctggatcca acagttaaac catgtgatgg tgtatactgt ggtatggcgt aaaacaacgg   7500
aaaagtcgct gaagacttaa aattcagggt ggctgatacc aaaatcagca gtggttgttc   7560
gtccacttaa aaataacgat tgtcatatct ggatccaaca gttaaaccat gtgatggtgt   7620
atactgtggt atggcgtaaa acaacggaga ggttcgaatc ctcccctaac cgcgggtagc   7680
ggcccaggta cccggatgtg ttttccgggc tgatgagtcc gtgaggacga aacctggctg   7740
caggcatgca agcttggcgt aatcatggtc atagctgttt cctgtgtgaa attgttatcc   7800
gctcacaatt ccacacaaca tacgagccgg aagcataaag tgtaaagcct ggggtgccta   7860
atgagtgagc taactcacat taattgcgtt gcgctcactg cccgctttcc agtcgggaaa   7920
cctgtcgtgc cagctgcatt aatgaatcgg ccaacgcgcg gggagaggcg gtttgcgtat   7980
tgggccctct tccgcttcct cgctcactga ctcgctgcgc tcggtcgttc ggctgcggcg   8040
agcggtatca gctcactcaa aggcggtaat acggttatcc acagaatcag gggataacgc   8100
aggaaagaac atgtgagcaa aaggccagca aaaggccagg aaccgtaaaa aggccgcgtt   8160
gctggcgttt ttccataggc tccgcccccc tgacgagcat cacaaaaatc gacgctcaag   8220
tcagaggtgg cgaaacccga caggactata agataccag gcgtttcccc ctggaagctc   8280
cctcgtgcgc tctcctgttc cgaccctgcc gcttaccgga tacctgtccg cctttctccc   8340
ttcgggaagc gtggcgcttt ctcatagctc acgctgtagg tatctcagtt cggtgtaggt   8400
cgttcgctcc aagctgggct gtgtgcacga accccccgtt cagcccgacc gctgcgcctt   8460
atccggtaac tatcgtcttg agtccaaccc ggtaagacac gacttatcgc cactggcagc   8520
agccactggt aacaggatta gcagagcgag gtatgtaggc ggtgctacag agttcttgaa   8580
gtggtggcct aactacggct acactagaag gacagtattt ggtatctgcg ctctgctgaa   8640
gccagttacc ttcggaaaaa gagttggtag ctcttgatcc ggcaaacaaa ccaccgctgg   8700
tagcggtggt ttttttgttt gcaagcagca gattacgcgc agaaaaaaag gatctcaaga   8760
agatcctttg atcttttcta cggggtctga cgctcagtgg aacgaaaact cacgttaagg   8820
gattttggtc atgagattat caaaaaggat cttcacctag atccttttaa attaaaaatg   8880
aagttttaaa tcaatctaaa gtatatatga gtaaacttgg tctgacagtt accaatgctt   8940
aatcagtgag gcacctatct cagcgatctg tctatttcgt tcatccatag ttgcctgact   9000
ccccgtcgtg tagataacta cgatacggga gggcttacca tctggcccca gtgctgcaat   9060
gataccgcga acccacgct caccggctcc agatttatca gcaataaacc agccagccgg   9120
aagggccgag cgcagaagtg gtcctgcaac tttatccgcc tccatccagt ctattaattg   9180
ttgccgggaa gctagagtaa gtagttcgcc agttaatagt ttgcgcaacg ttgttgccat   9240
tgctacaggc atcgtggtgt cacgctcgtc gtttggtatg gcttcattca gctccggttc   9300
ccaacgatca aggcgagtta catgatcccc catgttgtgc aaaaaagcgg ttagctcctt   9360
cggtcctccg atcgttgtca gaagtaagtt ggccgcagtg ttatcactca tggttatggc   9420
agcactgcat aattctctta ctgtcatgcc atccgtaaga tgcttttctg tgactggtga   9480
gtactcaacc aagtcattct gagaatagtg tatgcggcga ccgagttgct cttgcccggc   9540
gtcaatacgg gataataccg cgccacatag cagaacttta aaagtgctca tcattggaaa   9600
acgttcttcg gggcgaaaac tctcaaggat cttaccgctg ttgagatcca gttcgatgta   9660
acccactcgt gcacccaact gatcttcagc atcttttact ttcaccagcg tttctgggtg   9720
```

```
agcaaaaaca ggaaggcaaa atgccgcaaa aagggaata agggcgacac ggaaatgttg   9780
aatactcata ctcttccttt ttcaatatta ttgaagcatt tatcagggtt attgtctcat   9840 gtattttac aacaattacc aacaacaaca aacaacagac aacattacaa ttactattta   9900
caattacaat ggcatacaca cagacagcta ccacatcagc tttgctggac actgtccgag   9960
gaaacaactc cttggtcaat gatctagcaa agcgtcgtct ttacgacaca gcggttgaag  10020
agtttaacgc tcgtgaccgc aggcccaagg tgaacttttc aaaagtaata agcgaggagc  10080
agacgcttat tgctacccgg gcgtatccag aattccaaat tacatttat aacacgcaaa  10140 atgccgtgca ttcgcttgca ggtggattgc gatctttaga actggaatat ctgatgatgc  10200
aaattcccta cggatcattg acttatgaca taggcgggaa ttttgcatcg catctgttca  10260
agggacgagc atatgtacac tgctgcatgc ccaacctgga cgttcgagac atcatgcggc  10320
acgaaggcca gaaagacagt attgaactat acctttctag gctagagaga gggggggaaaa  10380 cagtcccccaa cttccaaaag gaagcatttg acagatacgg agaaattcct gaagacgctg  10440
tctgtcacaa tactttccag acatgcgaac atcagccgat gcagcaatca ggcagagtgt  10500
atgccattgc gctacacagc atatatgaca taccagccga tgagttcggg gcggcactct  10560
tgaggaaaaa tgtccatacg tgctatgccg cttttccactt ctccgagaac ctgcttcttg  10620
aagattcatg cgtcaatttg gacgaaatca acgcgtgttt ttcgcgcgat ggagacaagt  10680 tgacctttc ttttgcatca gagagtactc ttaattactg tcatagttat tctaatattc  10740
ttaagtatgt gtgcaaaact tacttcccgg cctctaatag agaggtttac atgaaggagt  10800
ttttagtcac cagagttaat acctggtttt gtaagttttc tagaatagat acttttcttt  10860
tgtacaaagg tgtggcccat aaaagtgtag atagtgagca gttttatact gcaatggaag  10920
acgcatggca ttacaaaaag actcttgcaa tgtgcaacag cgagagaatc ctccttgagg  10980
attcatcatc agtcaattac tggttttccca aaatgaggga tatggtcatc gtaccattat  11040
tcgacatttc tttggagact agtaagagga cgcgcaagga agtcttagtg tccaaggatt  11100
tcgtgtttac agtgcttaac cacattcgaa cataccaggc gaaagctctt acatacgcaa  11160
atgttttgtc cttcgtcgaa tcgattcgat cgagggtaat cattaacggt gtgacagcga  11220
ggtccgaatg ggatgtggac aaatctttgt tacaatcctt gtccatgacg ttttacctgc  11280
atactaagct tgccgttcta aaggatgact tactgattag caagtttagt ctcggttcga  11340
aaacggtgtg ccagcatgtg tgggatgaga tttcgctggc gtttgggaac gcatttccct  11400
ccgtgaaaga gaggctcttg aacaggaaac ttatcagagt ggcaggcgac gcattagaga  11460
tcagggtgcc tgatctatat gtgaccttcc acgacagatt agtgactgag tacaaggcct  11520
ctgtggacat gcctgcgctt gacattagga agaagatgga agaaacggaa gtgatgtaca  11580
atgcactttc agaattatcg gtgttaaggg agtctgacaa attcgatgtt gatgtttttt  11640
cccagatgtg ccaatctttg gaagttgacc caatgacggc agcgaaggtt atagtcgcgg  11700
tcatgagcaa tgagagcggt ctgactctca catttgaacg acctactgag gcgaatgttg  11760
cgctagcttt acaggatcaa gagaaggctt cagaaggtgc attggtagtt acctcaagag  11820
aagttgaaga accgtccatg aagggttcga tggccagagg agagttacaa ttagctggtc  11880
ttgctggaga tcatccggaa tcgtcctatt ctaagaacga ggagatagag tctttagagc  11940
agtttcatat ggcgacggca gattcgttaa ttcgtaagca gatgagctcg attgtgtaca  12000
cgggtccgat taaagttcag caaatgaaaa actttatcga tagcctggta gcatcactat  12060
ctgctgcggt gtcgaatctc gtcaagatcc tcaaagatac agctgctatt gaccttgaaa  12120
```

```
cccgtcaaaa gtttggagtc ttggatgttg catctaggaa gtggttaatc aaaccaacgg    12180
ccaagagtca tgcatggggt gttgttgaaa cccacgcgag gaagtatcat gtggcgcttt    12240
tggaatatga tgagcagggt gtggtgacat gcgatgattg gagaagagta gctgttagct    12300
ctgagtctgt tgtttattcc gacatggcga aactcagaac tctgcgcaga ctgcttcgaa    12360
acggagaacc gcatgtcagt agcgcaaagg ttgttcttgt ggacggagtt ccgggctgtg    12420
gaaaaaccaa agaaattctt tccagggtta attttgatga agatctaatt ttagtacctg    12480
ggaagcaagc cgcggaaatg atcagaagac gtgcgaattc ctcagggatt attgtggcca    12540
cgaaggacaa cgttaaaacc gttgattctt tcatgatgaa ttttgggaaa agcacacgct    12600
gtcagttcaa gaggttattc attgatgaag ggttgatgtt gcatactggt tgtgttaatt    12660
ttcttgtggc gatgtcattg tgcgaaattg catatgttta cggagacaca cagcagattc    12720
catacatcaa tagagtttca ggattcccgt accccgccca ttttgccaaa ttggaagttg    12780
acgaggtgga gacacgcaga actactctcc gttgtccagc cgatgtcaca cattatctga    12840
acaggagata tgagggcttt gtcatgagca cttcttcggt taaaaagtct gtttcgcagg    12900
agatggtcgg cggagccgcc gtgatcaatc cgatctcaaa acccttgcat ggcaagatcc    12960
tgacttttac ccaatcggat aaagaagctc tgctttcaag agggtattca gatgttcaca    13020
ctgtgcatga agtgcaaggc gagacatact ctgatgtttc actagttagg ttaacccca    13080 caccggtctc catcattgca ggagacagcc cacatgtttt ggtcgcattg tcaaggcaca    13140
cctgttcgct caagtactac actgttgtta tggatccttt agttagtatc attagagatc    13200
tagagaaact tagctcgtac ttgttagata tgtataaggt cgatgcagga acacaatagc    13260
aattacagat tgactcggtg ttcaaaggtt ccaatctttt tgttgcagcg ccaaagactg    13320
gtgatatttc tgatatgcag ttttactatg ataagtgtct cccaggcaac agcaccatga    13380
tgaataattt tgatgctgtt accatgaggt tgactgacat ttcattgaat gtcaaaaatt    13440
gcatattgga tatgtctaag tctgttgctg cgcctaagga tcaaatcaaa ccactaatac    13500
ctatggtacg aacggcggca gaaatgccac gccagactgg actattggaa aatttagtgg    13560
cgatgattaa aagaaacttt aacgcacccg agttgtctgg catcattgat attgaaaata    13620
ctgcatcttt ggttgtagat aagttttttg atagttattt gcttaaagaa aaagaaaac    13680 caaataaaaa tgtttctttg ttcagtagag agtctctcaa tagatggtta gaaaagcagg    13740
aacaggtaac aataggccag ctcgcagatt ttgattttgt ggatttgcca gcagttgatc    13800
agtacagaca catgattaaa gcacaaccca acaaaagtt ggacacttca atccaaacgg    13860
agtacccggc tttgcagacg attgtgtacc attcaaaaaa gatcaatgca atattcggcc    13920
cgttgtttag tgagcttact aggcaattac tggacagtgt tgattcgagc agatttttgt    13980
ttttcacaag aaagacacca gcgcagattg aggattcctt cggagatctc gacagtcatg    14040
tgccgatgga tgtcttggag ctggatatat caaaatacga caaatctcag aatgaattcc    14100
actgtgcagt agaatacgag atctggcgaa gattgggttt cgaagacttc ttgggagaag    14160
tttgaaaaca agggcataga aagaccaccc tcaaggatta taccgcaggt ataaaaactt    14220
gcatctggta tcaaagaaag agcggggacg tcacgacgtt cattggaaac actgtgatca    14280
ttgctgcatg tttggcctcg atgcttccga tggaaaaat aatcaaagga gccttttgcg    14340
gtgacgatag tctgctgtac tttccaaagg gttgtgagtt ccggatgtg caacactccg    14400 cgaatcttat gtggaatttt gaagcaaaac tgttaaaaa acagtatgga tacttttgcg    14460
gaagatatgt aatacatcac gacagaggat gcattgtgta ttacgatccc ctaaagttga    14520
```

```
tctcgaaact tggtgctaaa cacatcaagg attgggaaca cttggaggag ttcagaaggt   14580
ctctttgtga tgttgctgtt tcgttgaaca attgtgcgta ttacacacag ttggacgacg   14640
ctgtatggga ggttcataag accgcccctc caggttcgtt tgtttataaa agtctggtga   14700
agtatttgtc tgataaagtt cttttttagaa gtttgtttat agatggctct agttgttaaa   14760
ggaaaagtga atatcaatga gtttatcgac ctgacaaaaa tggagaagat cttaccgtcg   14820
atgtttaccc gtgtaaagag tgttatgtgt tccaaagttg ataaaataat ggttcatgag   14880
aatgagtcat tgtcagggt gaaccttctt aaaggagtta agcttattga tagtggatac   14940
gtctgtttag ccggtttggt cgtcacgggc gagtggaact tgcctgacaa ttgcagagga   15000
ggtgtgagcg tgtgtctggt ggacaaaagg atggaaagag ccgacgaggc cactctcgga   15060
tcttactaca cagcagctgc aaagaaaaga tttcagttca aggtcgttcc caattatgct   15120
ataaccaccc aggacgcgat gaaaaacgtc tggcaagttt tagttaatat tagaaatgtg   15180
aagatgtcag cgggtttctg tccgcttct ctggagtttg tgtcggtgtg tattgttat   15240 agaaataata taaaattagg tttgagagag aagattacaa acgtgagaga cggagggccc   15300
atggaactta cagaagaagt cgttgatgag ttcatggaag atgtccctat gtcgatcagg   15360
cttgcaaagt ttcgatctcg aaccggaaaa aagagtgatg tccgcaaagg gaaaaatagt   15420
agtagtgatc ggtcagtgcc gaacaagaac tatagaaatg ttaaggattt tggaggaatg   15480
agttttaaaa agaataattt aatcgatgat gattcggagg ctactgtcgc cgaatcggat   15540
tcgttttaaa tagatcttac agtatcacta ctccatctca gttcgtgttc ttgtcattaa   15600
ttaaatggct agcaaaggag aagaactttt cactggagtt gtcccaattc ttgttgaatt   15660
agatggtgat gttaatgggc acaaatttc tgtcagtgga gagggtgaag gtgatgctac   15720
atacggaaag cttaccctta aattatttg cactactgga aaactacctg ttccatggcc   15780
aacacttgtc actactttct cttatggtgt tcaatgcttt tcccgttatc cggatcatat   15840
gaaacggcat gactttttca agagtgccat gcccgaaggt tatgtacagg aacgcactat   15900 atcttcaaa gatgacggga actacaagac gcgtgctgaa gtcaagtttg aaggtgatac   15960
ccttgttaat cgtatcgagt taaaaggtat tgattttaaa gaagatggaa acattctcgg   16020
acacaaactc gagtacaact ataactcaca caatgtatac atcacggcag acaaacaaaa   16080
gaatggaatc aaagctaact tcaaaattcg ccacaacatt gaagatggat ccgttcaact   16140
agcagaccat tatcaacaaa atactccaat tggcgatggc cctgtccttt taccagacaa   16200
ccattacctg tcgacacaat ctgcccttc gaaagatccc aacgaaaagc gtgaccacat   16260
ggtccttctt gagtttgtaa ctgctgctgg gattacacat ggcatggatg agctctacaa   16320
ataatgacac tcgaggggta gtcaagatgc ataataaata acggattgtg tccgtaatca   16380
cacgtggtgc gtacgataac gcatagtgtt tttccctcca cttaaatcga agggttgtgt   16440
cttggatcgc gcgggtcaaa tgtatatggt tcatatacat ccgcaggcac gtaataaagc   16500
gaggggttcg ggtcgaggtc ggctgtgaaa ctcgaaaagg ttccggaaaa caaaaaagag   16560
agtggtaggt aatagtgtta ataataagaa ataaataat agtggtaaga aaggtttgaa   16620
agttgaggaa attgaggata atgtaagtga tgacgagtct atcgcgtcat cgagtacgtt   16680
ttaatcaata tgcctatac aatcaactct ccgagccaat ttgtttactt aagttccgct   16740
tatgcagatc ctgtgcagct gatcaatctg tgtacaaatg cattgggtaa ccagtttcaa   16800
acgcaacaag ctaggacaac agtccaacag caatttgcgg atgcctggaa acctgtgcct   16860
agtatgacag tgagatttcc tgcatcggat ttctatgtgt atagatataa ttcgacgctt   16920
```

```
gatccgttga tcacggcgtt attaaatagc ttcgatacta gaaatagaat aatagaggtt   16980
gataatcaac ccgcaccgaa tactactgaa atcgttaacg cgactcagag ggtagacgat   17040
gcgactgtag ctataagggc ttcaatcaat aatttggcta atgaactggt tcgtggaact   17100
ggcatgttca atcaagcaag ctttgagact gctagtggac ttgtctggac cacaactccg   17160
gctacttagc tattgttgtg agatttccta aaataaagtc actgaagact taaaattcag   17220
ggtggctgat accaaaatca gcagtggttg ttcgtccact taaatataac gattgtcata   17280
tctggatcca acagttaaac catgtgatgg tgtatactgt ggtatggcgt aaaacaacgg   17340
aaaagtcgct gaagacttaa aattcagggt ggctgatacc aaaatcagca gtggttgttc   17400
gtccacttaa aaataacgat tgtcatatct ggatccaaca gttaaaccat gtgatggtgt   17460
atactgtggt atggcgtaaa acaacggaga ggttcgaatc ctcccctaac cgcgggtagc   17520
ggcccaggta cccggatgtg ttttccgggc tgatgagtcc gtgaggacga aacctggctg   17580
caggcatgca agcttggcgt aatcatggtc atagctgttt cctgtgtgaa attgttatcc   17640
gctcacaatt ccacacaaca tacgagccgg aagcataaag tgtaaagcct ggggtgccta   17700
atgagtgagc taactcacat taattgcgtt gcgctcactg cccgctttcc agtcgggaaa   17760
cctgtcgtgc cagctgcatt aatgaatcgg ccaacgcgcg gggagaggcg gtttgcgtat   17820
tgggccctct tccgcttcct cgctcactga ctcgctgcgc tcggtcgttc ggctgcggcg   17880
agcggtatca gctcactcaa aggcggtaat acggttatcc acagaatcag ggataacgc   17940 aggaaagaac atgtgagcaa aaggccagca aaaggccagg aaccgtaaaa aggccgcgtt   18000
gctggcgttt ttccataggc tccgcccccc tgacgagcat cacaaaaatc gacgctcaag   18060
tcagaggtgg cgaaacccga caggactata aagataccag gcgtttcccc ctggaagctc   18120
cctcgtgcgc tctcctgttc cgaccctgcc gcttaccgga tacctgtccg cctttctccc   18180
ttcgggaagc gtggcgcttt ctcatagctc acgctgtagg tatctcagtt cggtgtaggt   18240
cgttcgctcc aagctgggct gtgtgcacga accccccgtt cagcccgacc gctgcgcctt   18300
atccggtaac tatcgtcttg agtccaaccc ggtaagacac gacttatcgc cactggcagc   18360
agccactggt aacaggatta gcagagcgag gtatgtaggc ggtgctacag agttcttgaa   18420
gtggtggcct aactacggct acactagaag gacagtattt ggtatctgcg ctctgctgaa   18480
gccagttacc ttcggaaaaa gagttggtag ctcttgatcc ggcaaacaaa ccaccgctgg   18540
tagcggtggt ttttttgttt gcaagcagca gattacgcgc agaaaaaaag gatctcaaga   18600
agatcctttg atcttttcta cggggtctga cgctcagtgg aacgaaaact cacgttaagg   18660
gattttggtc atgagattat caaaaaggat cttcacctag atccttttaa attaaaaatg   18720
aagttttaaa tcaatctaaa gtatatatga gtaaacttgg tctgacagtt accaatgctt   18780
aatcagtgag gcacctatct cagcgatctg tctatttcgt tcatccatag ttgcctgact   18840
ccccgtcgtg tagataacta cgatacggga gggcttacca tctggcccca gtgctgcaat   18900
gataccgcga gacccacgct caccggctcc agatttatca gcaataaacc agccagccgg   18960
aagggccgag cgcagaagtg gtcctgcaac tttatccgcc tccatccagt ctattaattg   19020
ttgccgggaa gctagagtaa gtagttcgcc agttaatagt ttgcgcaacg ttgttgccat   19080
tgctacaggc atcgtggtgt cacgctcgtc gtttggtatg gcttcattca gctccggttc   19140
ccaacgatca aggcgagtta catgatcccc catgttgtgc aaaaaagcgg ttagctcctt   19200
cggtcctccg atcgttgtca gaagtaagtt ggccgcagtg ttatcactca tggttatggc   19260
agcactgcat aattctctta ctgtcatgcc atccgtaaga tgcttttctg tgactggtga   19320
```

-continued

```
gtactcaacc aagtcattct gagaatagtg tatgcggcga ccgagttgct cttgcccggc    19380
gtcaatacgg gataataccg cgccacatag cagaacttta aaagtgctca tcattggaaa    19440
acgttcttcg gggcgaaaac tctcaaggat cttaccgctg ttgagatcca gttcgatgta    19500
acccactcgt gcacccaact gatcttcagc atctttttact ttcaccagcg tttctgggtg   19560
agcaaaaaca ggaaggcaaa atgccgcaaa aagggaata agggcgacac ggaaatgttg     19620
aatactcata ctcttccttt ttcaatatta ttgaagcatt tatcagggtt attgtctcat    19680
gagcggatac atatttgaat gtatttagaa aaataaacaa ataggggttc cgcgcacatt    19740
tccccgaaaa gtgccacctg acgtctaaga aaccattatt atcatgacat taacctataa    19800
aaataggcgt atcacgaggc cctttcgtct cgcgcgtttc ggtgatgacg gtgaaaacct    19860
ctgacacatg cagctcccgg agacggtcac agcttgtctg taagcggatg ccgggagcag    19920
acaagcccgt cagggcgcgt cagcgggtgt tggcgggtgt cggggctggc ttaactatgc    19980
ggcatcagag cagattgtac tgagagtgca ccatatgcgg tgtgaaatac cgcacagatg    20040
cgtaaggaga aaataccgca tcaggcgcat tcgccattca ggctgcgcaa ctgttgggaa    20100
gggcgatcgg tgcgggcctc ttcgctatta cgccagctgg cgaaagggggg atgtgctgca   20160 aggcgattaa gttgggtaac gccagggttt tcccagtcac gacgttgtaa aacgacggcc    20220
agtgaattca agcttaatac gactcactat a                                    20251
```

<210> SEQ ID NO 25
<211> LENGTH: 43
<212> TYPE: DNA
<213> ORGANISM: Artificial
<220> FEATURE:
<223> OTHER INFORMATION: synthetic oligonucleotide, see Example 2

<400> SEQUENCE: 25

```
gtgctcgagt cacagttcgt ccttctcttt agaacgtaaa ctt                         43
```

<210> SEQ ID NO 26
<211> LENGTH: 35
<212> TYPE: DNA
<213> ORGANISM: Artificial
<220> FEATURE:
<223> OTHER INFORMATION: synthetic oligonucleotide PacIexSP5', see
      Example 3

<400> SEQUENCE: 26

```
gtgttaatta acaatgggaa aaatggcttc tctat                                  35
```

<210> SEQ ID NO 27
<211> LENGTH: 28
<212> TYPE: DNA
<213> ORGANISM: Artificial
<220> FEATURE:
<223> OTHER INFORMATION: synthetic oligonucleotide EXIFNaSOE3', see
      Example 3

<400> SEQUENCE: 27

```
gtaagtcgca ggcggagctt tcgctagc                                          28
```

<210> SEQ ID NO 28
<211> LENGTH: 73
<212> TYPE: DNA
<213> ORGANISM: Artificial
<220> FEATURE:
<223> OTHER INFORMATION: synthetic oligonucleotide KP111, see Example 3

<400> SEQUENCE: 28

```
atgggaaaaa tggcttctct atttgccaca ttttagtgg ttttagtgtc acttagctta      60
gctagcgaaa gct                                                        73
```

<210> SEQ ID NO 29
<211> LENGTH: 28
<212> TYPE: DNA
<213> ORGANISM: Artificial
<220> FEATURE:
<223> OTHER INFORMATION: synthetic oligonucleotideEXIFNaSOE5', see
      Example 3

<400> SEQUENCE: 29

```
gctccgcctg cgacttacca caaactca                                        28
```

<210> SEQ ID NO 30
<211> LENGTH: 592
<212> TYPE: DNA
<213> ORGANISM: Artificial
<220> FEATURE:
<223> OTHER INFORMATION: human interferon alpha 2a extensin fusion with
      restriction enzyme sites, see Example 3
<220> FEATURE:
<221> NAME/KEY: CDS
<222> LOCATION: (11)..(583)
<220> FEATURE:
<221> NAME/KEY: mat_peptide
<222> LOCATION: (89)..(583)

<400> SEQUENCE: 30

```
ttaattaaca atg gga aaa atg gct tct cta ttt gcc aca ttt tta gtg         49
             Met Gly Lys Met Ala Ser Leu Phe Ala Thr Phe Leu Val
                 -25                 -20                 -15 gtt tta gtg tca ctt agc tta gct agc gaa agc tcc gcc tgc gac tta        97
Val Leu Val Ser Leu Ser Leu Ala Ser Glu Ser Ser Ala Cys Asp Leu
        -10                  -5              -1   1 cca caa act cac agc ctt ggt agt agg aga acg ttg atg tta ttg gcg       145
Pro Gln Thr His Ser Leu Gly Ser Arg Arg Thr Leu Met Leu Leu Ala
          5                  10                  15 cag atg agg aag ata tct tta ttc tct tgt ttg aag gat aga cat gac       193
Gln Met Arg Lys Ile Ser Leu Phe Ser Cys Leu Lys Asp Arg His Asp
 20                  25                  30                  35 ttc gga ttt cca caa gag gaa ttt ggt aat caa ttc caa aag gct gaa       241
Phe Gly Phe Pro Gln Glu Glu Phe Gly Asn Gln Phe Gln Lys Ala Glu
                 40                  45                  50 act ata cct gta tta cat gag atg ata cag caa atc ttc aat ctg ttt       289
Thr Ile Pro Val Leu His Glu Met Ile Gln Gln Ile Phe Asn Leu Phe
             55                  60                  65 agc aca aaa gac tca tct gct gca tgg gac gaa act ctc tta gac aaa       337
Ser Thr Lys Asp Ser Ser Ala Ala Trp Asp Glu Thr Leu Leu Asp Lys
         70                  75                  80 ttc tac act gaa ttg tac caa cag ctt aat gac ttg gaa gcc tgt gtg       385
Phe Tyr Thr Glu Leu Tyr Gln Gln Leu Asn Asp Leu Glu Ala Cys Val
     85                  90                  95 ata cag gga gtg ggt gta acg gag act cca ttg atg aag gag gac agc       433
Ile Gln Gly Val Gly Val Thr Glu Thr Pro Leu Met Lys Glu Asp Ser
100                 105                 110                 115 ata ctg gca gtg agg aaa tac ttc caa cga atc act tta tac ctg aaa       481
Ile Leu Ala Val Arg Lys Tyr Phe Gln Arg Ile Thr Leu Tyr Leu Lys
                120                 125                 130 gaa aag aaa tac tca cct tgt gcc tgg gag gtt gtc aga gca gaa ata       529
Glu Lys Lys Tyr Ser Pro Cys Ala Trp Glu Val Val Arg Ala Glu Ile
            135                 140                 145 atg aga tct ttc agt ctt tct act aac ttg caa gaa agt tta cgt tct       577
```

```
Met Arg Ser Phe Ser Leu Ser Thr Asn Leu Gln Glu Ser Leu Arg Ser
        150                 155                 160 aaa gag tgactcgag                                                    592
Lys Glu
    165

<210> SEQ ID NO 31
<211> LENGTH: 191
<212> TYPE: PRT
<213> ORGANISM: Artificial
<220> FEATURE:
<223> OTHER INFORMATION: Synthetic Construct

<400> SEQUENCE: 31

Met Gly Lys Met Ala Ser Leu Phe Ala Thr Phe Leu Val Val Leu Val
    -25                 -20                 -15

Ser Leu Ser Leu Ala Ser Glu Ser Ser Ala Cys Asp Leu Pro Gln Thr
-10                  -5                  -1  1               5

His Ser Leu Gly Ser Arg Arg Thr Leu Met Leu Leu Ala Gln Met Arg
                10                  15                  20

Lys Ile Ser Leu Phe Ser Cys Leu Lys Asp Arg His Asp Phe Gly Phe
            25                  30                  35

Pro Gln Glu Glu Phe Gly Asn Gln Phe Gln Lys Ala Glu Thr Ile Pro
        40                  45                  50

Val Leu His Glu Met Ile Gln Gln Ile Phe Asn Leu Phe Ser Thr Lys
55                  60                  65                  70

Asp Ser Ser Ala Ala Trp Asp Glu Thr Leu Leu Asp Lys Phe Tyr Thr
                75                  80                  85

Glu Leu Tyr Gln Gln Leu Asn Asp Leu Glu Ala Cys Val Ile Gln Gly
            90                  95                  100

Val Gly Val Thr Glu Thr Pro Leu Met Lys Glu Asp Ser Ile Leu Ala
        105                 110                 115

Val Arg Lys Tyr Phe Gln Arg Ile Thr Leu Tyr Leu Lys Glu Lys Lys
    120                 125                 130

Tyr Ser Pro Cys Ala Trp Glu Val Val Arg Ala Glu Ile Met Arg Ser
135                 140                 145                 150

Phe Ser Leu Ser Thr Asn Leu Gln Glu Ser Leu Arg Ser Lys Glu
                155                 160                 165

<210> SEQ ID NO 32
<211> LENGTH: 592
<212> TYPE: DNA
<213> ORGANISM: Artificial
<220> FEATURE:
<223> OTHER INFORMATION: human interferon alpha 2b extensin fusion with
      restriction enzyme sites, see Example 3
<220> FEATURE:
<221> NAME/KEY: CDS
<222> LOCATION: (11)..(583)
<220> FEATURE:
<221> NAME/KEY: mat_peptide
<222> LOCATION: (89)..(583)

<400> SEQUENCE: 32
ttaattaaca atg gga aaa atg gct tct cta ttt gcc aca ttt tta gtg      49
            Met Gly Lys Met Ala Ser Leu Phe Ala Thr Phe Leu Val
                -25                 -20                 -15 gtt tta gtg tca ctt agc tta gct agc gaa agc tcc gcc tgc gac tta    97
Val Leu Val Ser Leu Ser Leu Ala Ser Glu Ser Ser Ala Cys Asp Leu
            -10                  -5                  -1  1 cca caa act cac agc ctt ggt agt agg aga acg ttg atg tta ttg gcg   145
Pro Gln Thr His Ser Leu Gly Ser Arg Arg Thr Leu Met Leu Leu Ala
```

```
                    5                  10                 15
cag atg agg aga ata tct tta ttc tct tgt ttg aag gat aga cat gac   193
Gln Met Arg Arg Ile Ser Leu Phe Ser Cys Leu Lys Asp Arg His Asp
 20                 25                 30                 35 ttc gga ttt cca caa gag gaa ttt ggt aat caa ttc caa aag gct gaa   241
Phe Gly Phe Pro Gln Glu Glu Phe Gly Asn Gln Phe Gln Lys Ala Glu
                    40                 45                 50 act ata cct gta tta cat gag atg ata cag caa atc ttc aat ctg ttt   289
Thr Ile Pro Val Leu His Glu Met Ile Gln Gln Ile Phe Asn Leu Phe
                55                 60                 65 agc aca aaa gac tca tct gct gca tgg gac gaa act ctc tta gac aaa   337
Ser Thr Lys Asp Ser Ser Ala Ala Trp Asp Glu Thr Leu Leu Asp Lys
            70                 75                 80 ttc tac act gaa ttg tac caa cag ctt aat gac ttg gaa gcc tgt gtg   385
Phe Tyr Thr Glu Leu Tyr Gln Gln Leu Asn Asp Leu Glu Ala Cys Val
        85                 90                 95 ata cag gga gtg ggt gta acg gag act cca ttg atg aag gag gac agc   433
Ile Gln Gly Val Gly Val Thr Glu Thr Pro Leu Met Lys Glu Asp Ser
100                105                110                115 ata ctg gca gtg agg aaa tac ttc caa cga atc act tta tac ctg aaa   481
Ile Leu Ala Val Arg Lys Tyr Phe Gln Arg Ile Thr Leu Tyr Leu Lys
                   120                125                130 gag aag aaa tac tca cct tgt gcc tgg gag gtt gtc aga gca gaa ata   529
Glu Lys Lys Tyr Ser Pro Cys Ala Trp Glu Val Val Arg Ala Glu Ile
               135                140                145 atg aga tct ttc agt ctt tct act aac ttg caa gaa agt tta cgt tct   577
Met Arg Ser Phe Ser Leu Ser Thr Asn Leu Gln Glu Ser Leu Arg Ser
           150                155                160 aaa gag tgactcgag                                                  592
Lys Glu
   165
```

<210> SEQ ID NO 33
<211> LENGTH: 191
<212> TYPE: PRT
<213> ORGANISM: Artificial
<220> FEATURE:
<223> OTHER INFORMATION: Synthetic Construct

<400> SEQUENCE: 33

```
Met Gly Lys Met Ala Ser Leu Phe Ala Thr Phe Leu Val Val Leu Val
    -25                 -20                 -15

Ser Leu Ser Leu Ala Ser Glu Ser Ser Ala Cys Asp Leu Pro Gln Thr
-10                  -5              -1   1                  5

His Ser Leu Gly Ser Arg Arg Thr Leu Met Leu Leu Ala Gln Met Arg
                 10                  15                  20

Arg Ile Ser Leu Phe Ser Cys Leu Lys Asp Arg His Asp Phe Gly Phe
             25                  30                  35

Pro Gln Glu Glu Phe Gly Asn Gln Phe Gln Lys Ala Glu Thr Ile Pro
         40                  45                  50

Val Leu His Glu Met Ile Gln Gln Ile Phe Asn Leu Phe Ser Thr Lys
 55                  60                  65                  70

Asp Ser Ser Ala Ala Trp Asp Glu Thr Leu Leu Asp Lys Phe Tyr Thr
                 75                  80                  85

Glu Leu Tyr Gln Gln Leu Asn Asp Leu Glu Ala Cys Val Ile Gln Gly
             90                  95                 100

Val Gly Val Thr Glu Thr Pro Leu Met Lys Glu Asp Ser Ile Leu Ala
        105                 110                 115

Val Arg Lys Tyr Phe Gln Arg Ile Thr Leu Tyr Leu Lys Glu Lys Lys
```

```
                 120                 125                 130
Tyr Ser Pro Cys Ala Trp Glu Val Val Arg Ala Glu Ile Met Arg Ser
135                 140                 145                 150

Phe Ser Leu Ser Thr Asn Leu Gln Glu Ser Leu Arg Ser Lys Glu
                155                 160                 165

<210> SEQ ID NO 34
<211> LENGTH: 34
<212> TYPE: DNA
<213> ORGANISM: Artificial
<220> FEATURE:
<223> OTHER INFORMATION: synthetic oligonucleotide, see Example 5

<400> SEQUENCE: 34
gtgctcgagt catttagaac gtaaactttc ttgc                              34

<210> SEQ ID NO 35
<211> LENGTH: 34
<212> TYPE: DNA
<213> ORGANISM: Artificial
<220> FEATURE:
<223> OTHER INFORMATION: synthetic oligonucleotide, see Example 5

<400> SEQUENCE: 35
gtgctcgagt caagaacgta aactttcttg caag                              34

<210> SEQ ID NO 36
<211> LENGTH: 35
<212> TYPE: DNA
<213> ORGANISM: Artificial
<220> FEATURE:
<223> OTHER INFORMATION: synthetic oligonucleotide, see Example 5

<400> SEQUENCE: 36
gtgctcgagt caacgtaaac tttcttgcaa gttag                             35

<210> SEQ ID NO 37
<211> LENGTH: 35
<212> TYPE: DNA
<213> ORGANISM: Artificial
<220> FEATURE:
<223> OTHER INFORMATION: synthetic oligonucleotide, see Example 5

<400> SEQUENCE: 37
gtgctcgagt cataaacttt cttgcaagtt agtag                             35

<210> SEQ ID NO 38
<211> LENGTH: 36
<212> TYPE: DNA
<213> ORGANISM: Artificial
<220> FEATURE:
<223> OTHER INFORMATION: synthetic oligonucleotide, see Example 5

<400> SEQUENCE: 38
gtgctcgagt caactttctt gcaagttagt agaaag                            36

<210> SEQ ID NO 39
<211> LENGTH: 35
<212> TYPE: DNA
<213> ORGANISM: Artificial
<220> FEATURE:
<223> OTHER INFORMATION: synthetic oligonucleotide, see Example 5

<400> SEQUENCE: 39
gtgctcgagt cattcttgca agttagtaga aagac                             35
```

-continued

```
<210> SEQ ID NO 40
<211> LENGTH: 34
<212> TYPE: DNA
<213> ORGANISM: Artificial
<220> FEATURE:
<223> OTHER INFORMATION: synthetic oligonucleotide, see Example 5

<400> SEQUENCE: 40
gtgctcgagt cattgcaagt tagtagaaag actg                              34

<210> SEQ ID NO 41
<211> LENGTH: 35
<212> TYPE: DNA
<213> ORGANISM: Artificial
<220> FEATURE:
<223> OTHER INFORMATION: synthetic oligonucleotide, see Example 5

<400> SEQUENCE: 41
gtgctcgagt cacaagttag tagaaagact gaaag                             35

<210> SEQ ID NO 42
<211> LENGTH: 35
<212> TYPE: DNA
<213> ORGANISM: Artificial
<220> FEATURE:
<223> OTHER INFORMATION: synthetic oligonucleotide, see Example 5

<400> SEQUENCE: 42
gtgctcgagt cagttagtag aaagactgaa agatc                             35

<210> SEQ ID NO 43
<211> LENGTH: 34
<212> TYPE: DNA
<213> ORGANISM: Artificial
<220> FEATURE:
<223> OTHER INFORMATION: synthetic oligonucleotide, see Example 5

<400> SEQUENCE: 43
gtgctcgagt caagtagaaa gactgaaaga tctc                              34

<210> SEQ ID NO 44
<211> LENGTH: 589
<212> TYPE: DNA
<213> ORGANISM: Artificial
<220> FEATURE:
<223> OTHER INFORMATION: truncated human interferon alpha 2b extensin
      fusion with restriction enzyme sites, see Example 5
<220> FEATURE:
<221> NAME/KEY: CDS
<222> LOCATION: (11)..(580)
<220> FEATURE:
<221> NAME/KEY: mat_peptide
<222> LOCATION: (89)..(580)

<400> SEQUENCE: 44
ttaattaaca atg gga aaa atg gct tct cta ttt gcc aca ttt tta gtg     49
           Met Gly Lys Met Ala Ser Leu Phe Ala Thr Phe Leu Val
               -25                 -20                 -15 gtt tta gtg tca ctt agc tta gct agc gaa agc tcc gcc tgc gac tta    97
Val Leu Val Ser Leu Ser Leu Ala Ser Glu Ser Ser Ala Cys Asp Leu
        -10                 -5              -1  1 cca caa act cac agc ctt ggt agt agg aga acg ttg atg tta ttg gcg   145
Pro Gln Thr His Ser Leu Gly Ser Arg Arg Thr Leu Met Leu Leu Ala
    5                   10                  15 cag atg agg aga ata tct tta ttc tct tgt ttg aag gat aga cat gac   193
Gln Met Arg Arg Ile Ser Leu Phe Ser Cys Leu Lys Asp Arg His Asp
20                  25                  30                  35
```

```
ttc gga ttt cca caa gag gaa ttt ggt aat caa ttc caa aag gct gaa      241
Phe Gly Phe Pro Gln Glu Glu Phe Gly Asn Gln Phe Gln Lys Ala Glu
                40                  45                  50 act ata cct gta tta cat gag atg ata cag caa atc ttc aat ctg ttt      289
Thr Ile Pro Val Leu His Glu Met Ile Gln Gln Ile Phe Asn Leu Phe
        55                  60                  65 agc aca aaa gac tca tct gct gca tgg gac gaa act ctc tta gac aaa      337
Ser Thr Lys Asp Ser Ser Ala Ala Trp Asp Glu Thr Leu Leu Asp Lys
    70                  75                  80 ttc tac act gaa ttg tac caa cag ctt aat gac ttg gaa gcc tgt gtg      385
Phe Tyr Thr Glu Leu Tyr Gln Gln Leu Asn Asp Leu Glu Ala Cys Val
85                  90                  95 ata cag gga gtg ggt gta acg gag act cca ttg atg aag gag gac agc      433
Ile Gln Gly Val Gly Val Thr Glu Thr Pro Leu Met Lys Glu Asp Ser
100                 105                 110                 115 ata ctg gca gtg agg aaa tac ttc caa cga atc act tta tac ctg aaa      481
Ile Leu Ala Val Arg Lys Tyr Phe Gln Arg Ile Thr Leu Tyr Leu Lys
            120                 125                 130 gag aag aaa tac tca cct tgt gcc tgg gag gtt gtc aga gca gaa ata      529
Glu Lys Lys Tyr Ser Pro Cys Ala Trp Glu Val Val Arg Ala Glu Ile
                135                 140                 145 atg aga tct ttc agt ctt tct act aac ttg caa gaa agt tta cgt tct      577
Met Arg Ser Phe Ser Leu Ser Thr Asn Leu Gln Glu Ser Leu Arg Ser
                    150                 155                 160 aaa tgactcgag                                                        589
Lys

<210> SEQ ID NO 45
<211> LENGTH: 190
<212> TYPE: PRT
<213> ORGANISM: Artificial
<220> FEATURE:
<223> OTHER INFORMATION: Synthetic Construct

<400> SEQUENCE: 45

Met Gly Lys Met Ala Ser Leu Phe Ala Thr Phe Leu Val Val Leu Val
    -25                 -20                 -15

Ser Leu Ser Leu Ala Ser Glu Ser Ser Ala Cys Asp Leu Pro Gln Thr
-10                  -5                  -1  1                5

His Ser Leu Gly Ser Arg Arg Thr Leu Met Leu Leu Ala Gln Met Arg
            10                  15                  20

Arg Ile Ser Leu Phe Ser Cys Leu Lys Asp Arg His Asp Phe Gly Phe
                25                  30                  35

Pro Gln Glu Glu Phe Gly Asn Gln Phe Gln Lys Ala Glu Thr Ile Pro
        40                  45                  50

Val Leu His Glu Met Ile Gln Gln Ile Phe Asn Leu Phe Ser Thr Lys
55                  60                  65                  70

Asp Ser Ser Ala Ala Trp Asp Glu Thr Leu Leu Asp Lys Phe Tyr Thr
                75                  80                  85

Glu Leu Tyr Gln Gln Leu Asn Asp Leu Glu Ala Cys Val Ile Gln Gly
            90                  95                  100

Val Gly Val Thr Glu Thr Pro Leu Met Lys Glu Asp Ser Ile Leu Ala
        105                 110                 115

Val Arg Lys Tyr Phe Gln Arg Ile Thr Leu Tyr Leu Lys Glu Lys Lys
    120                 125                 130

Tyr Ser Pro Cys Ala Trp Glu Val Val Arg Ala Glu Ile Met Arg Ser
135                 140                 145                 150

Phe Ser Leu Ser Thr Asn Leu Gln Glu Ser Leu Arg Ser Lys
```

```
                     155                 160

<210> SEQ ID NO 46
<211> LENGTH: 586
<212> TYPE: DNA
<213> ORGANISM: Artificial
<220> FEATURE:
<223> OTHER INFORMATION: truncated human interferon alpha 2b extensin
      fusion with restriction enzyme sites, see Example 5
<220> FEATURE:
<221> NAME/KEY: CDS
<222> LOCATION: (11)..(577)
<220> FEATURE:
<221> NAME/KEY: mat_peptide
<222> LOCATION: (89)..(577)

<400> SEQUENCE: 46
ttaattaaca atg gga aaa atg gct tct cta ttt gcc aca ttt tta gtg         49
            Met Gly Lys Met Ala Ser Leu Phe Ala Thr Phe Leu Val
                -25                 -20                 -15 gtt tta gtg tca ctt agc tta gct agc gaa agc tcc gcc tgc gac tta        97
Val Leu Val Ser Leu Ser Leu Ala Ser Glu Ser Ser Ala Cys Asp Leu
        -10                 -5                 -1  1 cca caa act cac agc ctt ggt agt agg aga acg ttg atg tta ttg gcg       145
Pro Gln Thr His Ser Leu Gly Ser Arg Arg Thr Leu Met Leu Leu Ala
    5                   10                  15 cag atg agg aga ata tct tta ttc tct tgt ttg aag gat aga cat gac       193
Gln Met Arg Arg Ile Ser Leu Phe Ser Cys Leu Lys Asp Arg His Asp
 20                 25                  30                  35 ttc gga ttt cca caa gag gaa ttt ggt aat caa ttc caa aag gct gaa       241
Phe Gly Phe Pro Gln Glu Glu Phe Gly Asn Gln Phe Gln Lys Ala Glu
                40                  45                  50 act ata cct gta tta cat gag atg ata cag caa atc ttc aat ctg ttt       289
Thr Ile Pro Val Leu His Glu Met Ile Gln Gln Ile Phe Asn Leu Phe
            55                  60                  65 agc aca aaa gac tca tct gct gca tgg gac gaa act ctc tta gac aaa       337
Ser Thr Lys Asp Ser Ser Ala Ala Trp Asp Glu Thr Leu Leu Asp Lys
        70                  75                  80 ttc tac act gaa ttg tac caa cag ctt aat gac ttg gaa gcc tgt gtg       385
Phe Tyr Thr Glu Leu Tyr Gln Gln Leu Asn Asp Leu Glu Ala Cys Val
    85                  90                  95 ata cag gga gtg ggt gta acg gag act cca ttg atg aag gag gac agc       433
Ile Gln Gly Val Gly Val Thr Glu Thr Pro Leu Met Lys Glu Asp Ser
100                 105                 110                 115 ata ctg gca gtg agg aaa tac ttc caa cga atc act tta tac ctg aaa       481
Ile Leu Ala Val Arg Lys Tyr Phe Gln Arg Ile Thr Leu Tyr Leu Lys
                120                 125                 130 gag aag aaa tac tca cct tgt gcc tgg gag gtt gtc aga gca gaa ata       529
Glu Lys Lys Tyr Ser Pro Cys Ala Trp Glu Val Val Arg Ala Glu Ile
            135                 140                 145 atg aga tct ttc agt ctt tct act aac ttg caa gaa agt tta cgt tct       577
Met Arg Ser Phe Ser Leu Ser Thr Asn Leu Gln Glu Ser Leu Arg Ser
        150                 155                 160 tgactcgag                                                             586

<210> SEQ ID NO 47
<211> LENGTH: 189
<212> TYPE: PRT
<213> ORGANISM: Artificial
<220> FEATURE:
<223> OTHER INFORMATION: Synthetic Construct

<400> SEQUENCE: 47

Met Gly Lys Met Ala Ser Leu Phe Ala Thr Phe Leu Val Val Leu Val
```

```
                -25                 -20                 -15
Ser Leu Ser Leu Ala Ser Glu Ser Ser Ala Cys Asp Leu Pro Gln Thr
-10                 -5                  -1  1                   5

His Ser Leu Gly Ser Arg Arg Thr Leu Met Leu Leu Ala Gln Met Arg
                10                  15                  20

Arg Ile Ser Leu Phe Ser Cys Leu Lys Asp Arg His Asp Phe Gly Phe
                25                  30                  35

Pro Gln Glu Glu Phe Gly Asn Gln Phe Gln Lys Ala Glu Thr Ile Pro
    40                  45                  50

Val Leu His Glu Met Ile Gln Gln Ile Phe Asn Leu Phe Ser Thr Lys
55                  60                  65                  70

Asp Ser Ser Ala Ala Trp Asp Glu Thr Leu Leu Asp Lys Phe Tyr Thr
                75                  80                  85

Glu Leu Tyr Gln Gln Leu Asn Asp Leu Glu Ala Cys Val Ile Gln Gly
                90                  95                  100

Val Gly Val Thr Glu Thr Pro Leu Met Lys Glu Asp Ser Ile Leu Ala
                105                 110                 115

Val Arg Lys Tyr Phe Gln Arg Ile Thr Leu Tyr Leu Lys Glu Lys Lys
                120                 125                 130

Tyr Ser Pro Cys Ala Trp Glu Val Val Arg Ala Glu Ile Met Arg Ser
135                 140                 145                 150

Phe Ser Leu Ser Thr Asn Leu Gln Glu Ser Leu Arg Ser
                155                 160

<210> SEQ ID NO 48
<211> LENGTH: 583
<212> TYPE: DNA
<213> ORGANISM: Artificial
<220> FEATURE:
<223> OTHER INFORMATION: truncated human interferon alpha 2b extensin
      fusion with restriction enzyme sites, see Example 5
<220> FEATURE:
<221> NAME/KEY: CDS
<222> LOCATION: (11)..(574)
<220> FEATURE:
<221> NAME/KEY: mat_peptide
<222> LOCATION: (89)..(574)

<400> SEQUENCE: 48
ttaattaaca atg gga aaa atg gct tct cta ttt gcc aca ttt tta gtg         49
           Met Gly Lys Met Ala Ser Leu Phe Ala Thr Phe Leu Val
               -25                 -20                 -15 gtt tta gtg tca ctt agc tta gct agc gaa agc tcc gcc tgc gac tta       97
Val Leu Val Ser Leu Ser Leu Ala Ser Glu Ser Ser Ala Cys Asp Leu
    -10                 -5                  -1  1 cca caa act cac agc ctt ggt agt agg aga acg ttg atg tta ttg gcg      145
Pro Gln Thr His Ser Leu Gly Ser Arg Arg Thr Leu Met Leu Leu Ala
        5                   10                  15 cag atg agg aga ata tct tta ttc tct tgt ttg aag gat aga cat gac      193
Gln Met Arg Arg Ile Ser Leu Phe Ser Cys Leu Lys Asp Arg His Asp
20                  25                  30                  35 ttc gga ttt cca caa gag gaa ttt ggt aat caa ttc caa aag gct gaa      241
Phe Gly Phe Pro Gln Glu Glu Phe Gly Asn Gln Phe Gln Lys Ala Glu
                40                  45                  50 act ata cct gta tta cat gag atg ata cag caa atc ttc aat ctg ttt      289
Thr Ile Pro Val Leu His Glu Met Ile Gln Gln Ile Phe Asn Leu Phe
            55                  60                  65 agc aca aaa gac tca tct gct gca tgg gac gaa act ctc tta gac aaa      337
Ser Thr Lys Asp Ser Ser Ala Ala Trp Asp Glu Thr Leu Leu Asp Lys
        70                  75                  80
```

```
ttc tac act gaa ttg tac caa cag ctt aat gac ttg gaa gcc tgt gtg    385
Phe Tyr Thr Glu Leu Tyr Gln Gln Leu Asn Asp Leu Glu Ala Cys Val
     85                  90                  95 ata cag gga gtg ggt gta acg gag act cca ttg atg aag gag gac agc    433
Ile Gln Gly Val Gly Val Thr Glu Thr Pro Leu Met Lys Glu Asp Ser
100                 105                 110                 115 ata ctg gca gtg agg aaa tac ttc caa cga atc act tta tac ctg aaa    481
Ile Leu Ala Val Arg Lys Tyr Phe Gln Arg Ile Thr Leu Tyr Leu Lys
                120                 125                 130 gag aag aaa tac tca cct tgt gcc tgg gag gtt gtc aga gca gaa ata    529
Glu Lys Lys Tyr Ser Pro Cys Ala Trp Glu Val Val Arg Ala Glu Ile
                    135                 140                 145 atg aga tct ttc agt ctt tct act aac ttg caa gaa agt tta cgt        574
Met Arg Ser Phe Ser Leu Ser Thr Asn Leu Gln Glu Ser Leu Arg
            150                 155                 160 tgactcgag                                                          583
```

<210> SEQ ID NO 49
<211> LENGTH: 188
<212> TYPE: PRT
<213> ORGANISM: Artificial
<220> FEATURE:
<223> OTHER INFORMATION: Synthetic Construct

<400> SEQUENCE: 49

```
Met Gly Lys Met Ala Ser Leu Phe Ala Thr Phe Leu Val Val Leu Val
    -25                 -20                 -15

Ser Leu Ser Leu Ala Ser Glu Ser Ser Ala Cys Asp Leu Pro Gln Thr
-10                  -5              -1   1                   5

His Ser Leu Gly Ser Arg Arg Thr Leu Met Leu Leu Ala Gln Met Arg
             10                  15                  20

Arg Ile Ser Leu Phe Ser Cys Leu Lys Asp Arg His Asp Phe Gly Phe
            25                  30                  35

Pro Gln Glu Glu Phe Gly Asn Gln Phe Gln Lys Ala Glu Thr Ile Pro
        40                  45                  50

Val Leu His Glu Met Ile Gln Gln Ile Phe Asn Leu Phe Ser Thr Lys
55                  60                  65                  70

Asp Ser Ser Ala Ala Trp Asp Glu Thr Leu Leu Asp Lys Phe Tyr Thr
                75                  80                  85

Glu Leu Tyr Gln Gln Leu Asn Asp Leu Glu Ala Cys Val Ile Gln Gly
            90                  95                  100

Val Gly Val Thr Glu Thr Pro Leu Met Lys Glu Asp Ser Ile Leu Ala
        105                 110                 115

Val Arg Lys Tyr Phe Gln Arg Ile Thr Leu Tyr Leu Lys Glu Lys Lys
    120                 125                 130

Tyr Ser Pro Cys Ala Trp Glu Val Val Arg Ala Glu Ile Met Arg Ser
135                 140                 145                 150

Phe Ser Leu Ser Thr Asn Leu Gln Glu Ser Leu Arg
                155                 160
```

<210> SEQ ID NO 50
<211> LENGTH: 580
<212> TYPE: DNA
<213> ORGANISM: Artificial
<220> FEATURE:
<223> OTHER INFORMATION: truncated human interferon alpha 2b extensin
      fusion with restriction enzyme sites, see Example 5
<220> FEATURE:
<221> NAME/KEY: CDS
<222> LOCATION: (11)..(571)
<220> FEATURE:

<221> NAME/KEY: mat_peptide
<222> LOCATION: (89)..(571)

<400> SEQUENCE: 50

```
ttaattaaca atg gga aaa atg gct tct cta ttt gcc aca ttt tta gtg        49
           Met Gly Lys Met Ala Ser Leu Phe Ala Thr Phe Leu Val
               -25             -20                 -15 gtt tta gtg tca ctt agc tta gct agc gaa agc tcc gcc tgc gac tta        97
Val Leu Val Ser Leu Ser Leu Ala Ser Glu Ser Ser Ala Cys Asp Leu
            -10             -5              -1  1 cca caa act cac agc ctt ggt agt agg aga acg ttg atg tta ttg gcg       145
Pro Gln Thr His Ser Leu Gly Ser Arg Arg Thr Leu Met Leu Leu Ala
     5               10                  15 cag atg agg aga ata tct tta ttc tct tgt ttg aag gat aga cat gac       193
Gln Met Arg Arg Ile Ser Leu Phe Ser Cys Leu Lys Asp Arg His Asp
 20              25                  30                  35 ttc gga ttt cca caa gag gaa ttt ggt aat caa ttc caa aag gct gaa       241
Phe Gly Phe Pro Gln Glu Glu Phe Gly Asn Gln Phe Gln Lys Ala Glu
                 40                  45                  50 act ata cct gta tta cat gag atg ata cag caa atc ttc aat ctg ttt       289
Thr Ile Pro Val Leu His Glu Met Ile Gln Gln Ile Phe Asn Leu Phe
             55                  60                  65 agc aca aaa gac tca tct gct gca tgg gac gaa act ctc tta gac aaa       337
Ser Thr Lys Asp Ser Ser Ala Ala Trp Asp Glu Thr Leu Leu Asp Lys
         70                  75                  80 ttc tac act gaa ttg tac caa cag ctt aat gac ttg gaa gcc tgt gtg       385
Phe Tyr Thr Glu Leu Tyr Gln Gln Leu Asn Asp Leu Glu Ala Cys Val
     85                  90                  95 ata cag gga gtg ggt gta acg gag act cca ttg atg aag gag gac agc       433
Ile Gln Gly Val Gly Val Thr Glu Thr Pro Leu Met Lys Glu Asp Ser
100                 105                 110                 115 ata ctg gca gtg agg aaa tac ttc caa cga atc act tta tac ctg aaa       481
Ile Leu Ala Val Arg Lys Tyr Phe Gln Arg Ile Thr Leu Tyr Leu Lys
                 120                 125                 130 gag aag aaa tac tca cct tgt gcc tgg gag gtt gtc aga gca gaa ata       529
Glu Lys Lys Tyr Ser Pro Cys Ala Trp Glu Val Val Arg Ala Glu Ile
             135                 140                 145 atg aga tct ttc agt ctt tct act aac ttg caa gaa agt tta tgactcgag    580
Met Arg Ser Phe Ser Leu Ser Thr Asn Leu Gln Glu Ser Leu
         150                 155                 160
```

<210> SEQ ID NO 51
<211> LENGTH: 187
<212> TYPE: PRT
<213> ORGANISM: Artificial
<220> FEATURE:
<223> OTHER INFORMATION: Synthetic Construct

<400> SEQUENCE: 51

```
Met Gly Lys Met Ala Ser Leu Phe Ala Thr Phe Leu Val Val Leu Val
    -25             -20                 -15

Ser Leu Ser Leu Ala Ser Glu Ser Ser Ala Cys Asp Leu Pro Gln Thr
-10             -5              -1  1               5

His Ser Leu Gly Ser Arg Arg Thr Leu Met Leu Leu Ala Gln Met Arg
         10                  15                  20

Arg Ile Ser Leu Phe Ser Cys Leu Lys Asp Arg His Asp Phe Gly Phe
             25                  30                  35

Pro Gln Glu Glu Phe Gly Asn Gln Phe Gln Lys Ala Glu Thr Ile Pro
         40                  45                  50

Val Leu His Glu Met Ile Gln Gln Ile Phe Asn Leu Phe Ser Thr Lys
55                  60                  65                  70
```

```
Asp Ser Ser Ala Ala Trp Asp Glu Thr Leu Leu Asp Lys Phe Tyr Thr
             75                  80                  85

Glu Leu Tyr Gln Gln Leu Asn Asp Leu Glu Ala Cys Val Ile Gln Gly
         90                  95                 100

Val Gly Val Thr Glu Thr Pro Leu Met Lys Glu Asp Ser Ile Leu Ala
        105                 110                 115

Val Arg Lys Tyr Phe Gln Arg Ile Thr Leu Tyr Leu Lys Glu Lys Lys
    120                 125                 130

Tyr Ser Pro Cys Ala Trp Glu Val Val Arg Ala Glu Ile Met Arg Ser
135                 140                 145                 150

Phe Ser Leu Ser Thr Asn Leu Gln Glu Ser Leu
                155                 160

<210> SEQ ID NO 52
<211> LENGTH: 577
<212> TYPE: DNA
<213> ORGANISM: Artificial
<220> FEATURE:
<223> OTHER INFORMATION: truncated human interferon alpha 2b extensin
      fusion with restriction enzyme sites, see Example 5
<220> FEATURE:
<221> NAME/KEY: CDS
<222> LOCATION: (11)..(568)
<220> FEATURE:
<221> NAME/KEY: mat_peptide
<222> LOCATION: (89)..(568)

<400> SEQUENCE: 52
ttaattaaca atg gga aaa atg gct tct cta ttt gcc aca ttt tta gtg       49
           Met Gly Lys Met Ala Ser Leu Phe Ala Thr Phe Leu Val
               -25                 -20                 -15 gtt tta gtg tca ctt agc tta gct agc gaa agc tcc gcc tgc gac tta     97
Val Leu Val Ser Leu Ser Leu Ala Ser Glu Ser Ser Ala Cys Asp Leu
            -10                 -5             -1  1 cca caa act cac agc ctt ggt agt agg aga acg ttg atg tta ttg gcg    145
Pro Gln Thr His Ser Leu Gly Ser Arg Arg Thr Leu Met Leu Leu Ala
      5                  10                  15 cag atg agg aga ata tct tta ttc tct tgt ttg aag gat aga cat gac    193
Gln Met Arg Arg Ile Ser Leu Phe Ser Cys Leu Lys Asp Arg His Asp
 20                  25                  30                  35 ttc gga ttt cca caa gag gaa ttt ggt aat caa ttc caa aag gct gaa    241
Phe Gly Phe Pro Gln Glu Glu Phe Gly Asn Gln Phe Gln Lys Ala Glu
                 40                  45                  50 act ata cct gta tta cat gag atg ata cag caa atc ttc aat ctg ttt    289
Thr Ile Pro Val Leu His Glu Met Ile Gln Gln Ile Phe Asn Leu Phe
             55                  60                  65 agc aca aaa gac tca tct gct gca tgg gac gaa act ctc tta gac aaa    337
Ser Thr Lys Asp Ser Ser Ala Ala Trp Asp Glu Thr Leu Leu Asp Lys
         70                  75                  80 ttc tac act gaa ttg tac caa cag ctt aat gac ttg gaa gcc tgt gtg    385
Phe Tyr Thr Glu Leu Tyr Gln Gln Leu Asn Asp Leu Glu Ala Cys Val
     85                  90                  95 ata cag gga gtg ggt gta acg gag act cca ttg atg aag gag gac agc    433
Ile Gln Gly Val Gly Val Thr Glu Thr Pro Leu Met Lys Glu Asp Ser
100                 105                 110                 115 ata ctg gca gtg agg aaa tac ttc caa cga atc act tta tac ctg aaa    481
Ile Leu Ala Val Arg Lys Tyr Phe Gln Arg Ile Thr Leu Tyr Leu Lys
                 120                 125                 130 gag aag aaa tac tca cct tgt gcc tgg gag gtt gtc aga gca gaa ata    529
Glu Lys Lys Tyr Ser Pro Cys Ala Trp Glu Val Val Arg Ala Glu Ile
             135                 140                 145
```

```
atg aga tct ttc agt ctt tct act aac ttg caa gaa agt tgactcgag    577
Met Arg Ser Phe Ser Leu Ser Thr Asn Leu Gln Glu Ser
        150                 155                 160
```

<210> SEQ ID NO 53
<211> LENGTH: 186
<212> TYPE: PRT
<213> ORGANISM: Artificial
<220> FEATURE:
<223> OTHER INFORMATION: Synthetic Construct

<400> SEQUENCE: 53

```
Met Gly Lys Met Ala Ser Leu Phe Ala Thr Phe Leu Val Val Leu Val
    -25                 -20                 -15

Ser Leu Ser Leu Ala Ser Glu Ser Ser Ala Cys Asp Leu Pro Gln Thr
-10                  -5                 -1   1               5

His Ser Leu Gly Ser Arg Arg Thr Leu Met Leu Leu Ala Gln Met Arg
                10                  15                  20

Arg Ile Ser Leu Phe Ser Cys Leu Lys Asp Arg His Asp Phe Gly Phe
            25                  30                  35

Pro Gln Glu Glu Phe Gly Asn Gln Phe Gln Lys Ala Glu Thr Ile Pro
        40                  45                  50

Val Leu His Glu Met Ile Gln Gln Ile Phe Asn Leu Phe Ser Thr Lys
55                  60                  65                  70

Asp Ser Ser Ala Ala Trp Asp Glu Thr Leu Leu Asp Lys Phe Tyr Thr
                75                  80                  85

Glu Leu Tyr Gln Gln Leu Asn Asp Leu Glu Ala Cys Val Ile Gln Gly
            90                  95                  100

Val Gly Val Thr Glu Thr Pro Leu Met Lys Glu Asp Ser Ile Leu Ala
        105                 110                 115

Val Arg Lys Tyr Phe Gln Arg Ile Thr Leu Tyr Leu Lys Glu Lys Lys
    120                 125                 130

Tyr Ser Pro Cys Ala Trp Glu Val Val Arg Ala Glu Ile Met Arg Ser
135                 140                 145                 150

Phe Ser Leu Ser Thr Asn Leu Gln Glu Ser
                155                 160
```

<210> SEQ ID NO 54
<211> LENGTH: 574
<212> TYPE: DNA
<213> ORGANISM: Artificial
<220> FEATURE:
<223> OTHER INFORMATION: truncated human interferon alpha 2b extensin
      fusion with restriction enzyme sites, see Example 5
<220> FEATURE:
<221> NAME/KEY: CDS
<222> LOCATION: (11)..(565)
<220> FEATURE:
<221> NAME/KEY: mat_peptide
<222> LOCATION: (89)..(565)

<400> SEQUENCE: 54

```
ttaattaaca atg gga aaa atg gct tct cta ttt gcc aca ttt tta gtg    49
            Met Gly Lys Met Ala Ser Leu Phe Ala Thr Phe Leu Val
                -25                 -20                 -15 gtt tta gtg tca ctt agc tta gct agc gaa agc tcc gcc tgc gac tta   97
Val Leu Val Ser Leu Ser Leu Ala Ser Glu Ser Ser Ala Cys Asp Leu
            -10                  -5                 -1   1 cca caa act cac agc ctt ggt agt agg aga acg ttg atg tta ttg gcg   145
Pro Gln Thr His Ser Leu Gly Ser Arg Arg Thr Leu Met Leu Leu Ala
         5                  10                  15 cag atg agg aga ata tct tta ttc tct tgt ttg aag gat aga cat gac   193
Gln Met Arg Arg Ile Ser Leu Phe Ser Cys Leu Lys Asp Arg His Asp
```

```
Gln Met Arg Arg Ile Ser Leu Phe Ser Cys Leu Lys Asp Arg His Asp
 20                  25                  30                  35 ttc gga ttt cca caa gag gaa ttt ggt aat caa ttc caa aag gct gaa      241
Phe Gly Phe Pro Gln Glu Glu Phe Gly Asn Gln Phe Gln Lys Ala Glu
                 40                  45                  50 act ata cct gta tta cat gag atg ata cag caa atc ttc aat ctg ttt      289
Thr Ile Pro Val Leu His Glu Met Ile Gln Gln Ile Phe Asn Leu Phe
                     55                  60                  65 agc aca aaa gac tca tct gct gca tgg gac gaa act ctc tta gac aaa      337
Ser Thr Lys Asp Ser Ser Ala Ala Trp Asp Glu Thr Leu Leu Asp Lys
         70                  75                  80 ttc tac act gaa ttg tac caa cag ctt aat gac ttg gaa gcc tgt gtg      385
Phe Tyr Thr Glu Leu Tyr Gln Gln Leu Asn Asp Leu Glu Ala Cys Val
 85                  90                  95 ata cag gga gtg ggt gta acg gag act cca ttg atg aag gag gac agc      433
Ile Gln Gly Val Gly Val Thr Glu Thr Pro Leu Met Lys Glu Asp Ser
100                 105                 110                 115 ata ctg gca gtg agg aaa tac ttc caa cga atc act tta tac ctg aaa      481
Ile Leu Ala Val Arg Lys Tyr Phe Gln Arg Ile Thr Leu Tyr Leu Lys
                120                 125                 130 gag aag aaa tac tca cct tgt gcc tgg gag gtt gtc aga gca gaa ata      529
Glu Lys Lys Tyr Ser Pro Cys Ala Trp Glu Val Val Arg Ala Glu Ile
                    135                 140                 145 atg aga tct ttc agt ctt tct act aac ttg caa gaa tgactcgag            574
Met Arg Ser Phe Ser Leu Ser Thr Asn Leu Gln Glu
                150                 155

<210> SEQ ID NO 55
<211> LENGTH: 185
<212> TYPE: PRT
<213> ORGANISM: Artificial
<220> FEATURE:
<223> OTHER INFORMATION: Synthetic Construct

<400> SEQUENCE: 55

Met Gly Lys Met Ala Ser Leu Phe Ala Thr Phe Leu Val Val Leu Val
            -25                 -20                 -15

Ser Leu Ser Leu Ala Ser Glu Ser Ser Ala Cys Asp Leu Pro Gln Thr
-10                  -5                  -1  1                   5

His Ser Leu Gly Ser Arg Arg Thr Leu Met Leu Leu Ala Gln Met Arg
                 10                  15                  20

Arg Ile Ser Leu Phe Ser Cys Leu Lys Asp Arg His Asp Phe Gly Phe
                 25                  30                  35

Pro Gln Glu Glu Phe Gly Asn Gln Phe Gln Lys Ala Glu Thr Ile Pro
 40                  45                  50

Val Leu His Glu Met Ile Gln Gln Ile Phe Asn Leu Phe Ser Thr Lys
 55                  60                  65                  70

Asp Ser Ser Ala Ala Trp Asp Glu Thr Leu Leu Asp Lys Phe Tyr Thr
                 75                  80                  85

Glu Leu Tyr Gln Gln Leu Asn Asp Leu Glu Ala Cys Val Ile Gln Gly
                 90                  95                 100

Val Gly Val Thr Glu Thr Pro Leu Met Lys Glu Asp Ser Ile Leu Ala
            105                 110                 115

Val Arg Lys Tyr Phe Gln Arg Ile Thr Leu Tyr Leu Lys Glu Lys Lys
            120                 125                 130

Tyr Ser Pro Cys Ala Trp Glu Val Val Arg Ala Glu Ile Met Arg Ser
135                 140                 145                 150

Phe Ser Leu Ser Thr Asn Leu Gln Glu
                155
```

<210> SEQ ID NO 56
<211> LENGTH: 571
<212> TYPE: DNA
<213> ORGANISM: Artificial
<220> FEATURE:
<223> OTHER INFORMATION: truncated human interferon alpha 2b extensin
      fusion with restriction enzyme sites, see Example 5
<220> FEATURE:
<221> NAME/KEY: CDS
<222> LOCATION: (11)..(562)
<220> FEATURE:
<221> NAME/KEY: mat_peptide
<222> LOCATION: (89)..(562)

<400> SEQUENCE: 56

```
ttaattaaca atg gga aaa atg gct tct cta ttt gcc aca ttt tta gtg          49
           Met Gly Lys Met Ala Ser Leu Phe Ala Thr Phe Leu Val
               -25                 -20                 -15 gtt tta gtg tca ctt agc tta gct agc gaa agc tcc gcc tgc gac tta         97
Val Leu Val Ser Leu Ser Leu Ala Ser Glu Ser Ser Ala Cys Asp Leu
            -10                 -5                  -1  1 cca caa act cac agc ctt ggt agt agg aga acg ttg atg tta ttg gcg        145
Pro Gln Thr His Ser Leu Gly Ser Arg Arg Thr Leu Met Leu Leu Ala
  5                  10                  15 cag atg agg aga ata tct tta ttc tct tgt ttg aag gat aga cat gac        193
Gln Met Arg Arg Ile Ser Leu Phe Ser Cys Leu Lys Asp Arg His Asp
 20                  25                  30                  35 ttc gga ttt cca caa gag gaa ttt ggt aat caa ttc caa aag gct gaa        241
Phe Gly Phe Pro Gln Glu Glu Phe Gly Asn Gln Phe Gln Lys Ala Glu
                 40                  45                  50 act ata cct gta tta cat gag atg ata cag caa atc ttc aat ctg ttt        289
Thr Ile Pro Val Leu His Glu Met Ile Gln Gln Ile Phe Asn Leu Phe
             55                  60                  65 agc aca aaa gac tca tct gct gca tgg gac gaa act ctc tta gac aaa        337
Ser Thr Lys Asp Ser Ser Ala Ala Trp Asp Glu Thr Leu Leu Asp Lys
         70                  75                  80 ttc tac act gaa ttg tac caa cag ctt aat gac ttg gaa gcc tgt gtg        385
Phe Tyr Thr Glu Leu Tyr Gln Gln Leu Asn Asp Leu Glu Ala Cys Val
     85                  90                  95 ata cag gga gtg ggt gta acg gag act cca ttg atg aag gag gac agc        433
Ile Gln Gly Val Gly Val Thr Glu Thr Pro Leu Met Lys Glu Asp Ser
100                 105                 110                 115 ata ctg gca gtg agg aaa tac ttc caa cga atc act tta tac ctg aaa        481
Ile Leu Ala Val Arg Lys Tyr Phe Gln Arg Ile Thr Leu Tyr Leu Lys
                 120                 125                 130 gag aag aaa tac tca cct tgt gcc tgg gag gtt gtc aga gca gaa ata        529
Glu Lys Lys Tyr Ser Pro Cys Ala Trp Glu Val Val Arg Ala Glu Ile
             135                 140                 145 atg aga tct ttc agt ctt tct act aac ttg caa tgactcgag                  571
Met Arg Ser Phe Ser Leu Ser Thr Asn Leu Gln
         150                 155
```

<210> SEQ ID NO 57
<211> LENGTH: 184
<212> TYPE: PRT
<213> ORGANISM: Artificial
<220> FEATURE:
<223> OTHER INFORMATION: Synthetic Construct

<400> SEQUENCE: 57

```
Met Gly Lys Met Ala Ser Leu Phe Ala Thr Phe Leu Val Val Leu Val
    -25                 -20                 -15

Ser Leu Ser Leu Ala Ser Glu Ser Ser Ala Cys Asp Leu Pro Gln Thr
```

```
            -10                -5             -1  1              5
His Ser Leu Gly Ser Arg Arg Thr Leu Met Leu Leu Ala Gln Met Arg
                10                 15                20

Arg Ile Ser Leu Phe Ser Cys Leu Lys Asp Arg His Asp Phe Gly Phe
        25                  30                 35

Pro Gln Glu Glu Phe Gly Asn Gln Phe Gln Lys Ala Glu Thr Ile Pro
    40                  45                 50

Val Leu His Glu Met Ile Gln Gln Ile Phe Asn Leu Phe Ser Thr Lys
55                  60                  65                 70

Asp Ser Ser Ala Ala Trp Asp Glu Thr Leu Leu Asp Lys Phe Tyr Thr
            75                  80                 85

Glu Leu Tyr Gln Gln Leu Asn Asp Leu Glu Ala Cys Val Ile Gln Gly
        90                  95                100

Val Gly Val Thr Glu Thr Pro Leu Met Lys Glu Asp Ser Ile Leu Ala
        105                 110                115

Val Arg Lys Tyr Phe Gln Arg Ile Thr Leu Tyr Leu Lys Glu Lys Lys
        120                 125                130

Tyr Ser Pro Cys Ala Trp Glu Val Val Arg Ala Glu Ile Met Arg Ser
135                 140                 145                150

Phe Ser Leu Ser Thr Asn Leu Gln
                155

<210> SEQ ID NO 58
<211> LENGTH: 568
<212> TYPE: DNA
<213> ORGANISM: Artificial
<220> FEATURE:
<223> OTHER INFORMATION: truncated human interferon alpha 2b extensin
      fusion with restriction enzyme sites, see Example 5
<220> FEATURE:
<221> NAME/KEY: CDS
<222> LOCATION: (11)..(559)
<220> FEATURE:
<221> NAME/KEY: mat_peptide
<222> LOCATION: (89)..(559)

<400> SEQUENCE: 58
ttaattaaca atg gga aaa atg gct tct cta ttt gcc aca ttt tta gtg        49
           Met Gly Lys Met Ala Ser Leu Phe Ala Thr Phe Leu Val
               -25                 -20                -15 gtt tta gtg tca ctt agc tta gct agc gaa agc tcc gcc tgc gac tta       97
Val Leu Val Ser Leu Ser Leu Ala Ser Glu Ser Ser Ala Cys Asp Leu
            -10                 -5                 -1  1 cca caa act cac agc ctt ggt agt agg aga acg ttg atg tta ttg gcg      145
Pro Gln Thr His Ser Leu Gly Ser Arg Arg Thr Leu Met Leu Leu Ala
    5                  10                 15 cag atg agg aga ata tct tta ttc tct tgt ttg aag gat aga cat gac      193
Gln Met Arg Arg Ile Ser Leu Phe Ser Cys Leu Lys Asp Arg His Asp
20                  25                  30                 35 ttc gga ttt cca caa gag gaa ttt ggt aat caa ttc caa aag gct gaa      241
Phe Gly Phe Pro Gln Glu Glu Phe Gly Asn Gln Phe Gln Lys Ala Glu
            40                  45                 50 act ata cct gta tta cat gag atg ata cag caa atc ttc aat ctg ttt      289
Thr Ile Pro Val Leu His Glu Met Ile Gln Gln Ile Phe Asn Leu Phe
        55                  60                 65 agc aca aaa gac tca tct gct gca tgg gac gaa act ctc tta gac aaa      337
Ser Thr Lys Asp Ser Ser Ala Ala Trp Asp Glu Thr Leu Leu Asp Lys
        70                  75                 80 ttc tac act gaa ttg tac caa cag ctt aat gac ttg gaa gcc tgt gtg      385
Phe Tyr Thr Glu Leu Tyr Gln Gln Leu Asn Asp Leu Glu Ala Cys Val
    85                  90                 95
```

```
ata cag gga gtg ggt gta acg gag act cca ttg atg aag gag gac agc        433
Ile Gln Gly Val Gly Val Thr Glu Thr Pro Leu Met Lys Glu Asp Ser
100             105                 110                 115 ata ctg gca gtg agg aaa tac ttc caa cga atc act tta tac ctg aaa        481
Ile Leu Ala Val Arg Lys Tyr Phe Gln Arg Ile Thr Leu Tyr Leu Lys
            120                 125                 130 gag aag aaa tac tca cct tgt gcc tgg gag gtt gtc aga gca gaa ata        529
Glu Lys Lys Tyr Ser Pro Cys Ala Trp Glu Val Val Arg Ala Glu Ile
                135                 140                 145 atg aga tct ttc agt ctt tct act aac ttg tgactcgag                      568
Met Arg Ser Phe Ser Leu Ser Thr Asn Leu
        150                 155

<210> SEQ ID NO 59
<211> LENGTH: 183
<212> TYPE: PRT
<213> ORGANISM: Artificial
<220> FEATURE:
<223> OTHER INFORMATION: Synthetic Construct

<400> SEQUENCE: 59

Met Gly Lys Met Ala Ser Leu Phe Ala Thr Phe Leu Val Val Leu Val
    -25                 -20                 -15

Ser Leu Ser Leu Ala Ser Glu Ser Ser Ala Cys Asp Leu Pro Gln Thr
-10             -5                  -1  1               5

His Ser Leu Gly Ser Arg Arg Thr Leu Met Leu Leu Ala Gln Met Arg
                10                  15                  20

Arg Ile Ser Leu Phe Ser Cys Leu Lys Asp Arg His Asp Phe Gly Phe
            25                  30                  35

Pro Gln Glu Glu Phe Gly Asn Gln Phe Gln Lys Ala Glu Thr Ile Pro
        40                  45                  50

Val Leu His Glu Met Ile Gln Gln Ile Phe Asn Leu Phe Ser Thr Lys
55                  60                  65                  70

Asp Ser Ser Ala Ala Trp Asp Glu Thr Leu Leu Asp Lys Phe Tyr Thr
                75                  80                  85

Glu Leu Tyr Gln Gln Leu Asn Asp Leu Glu Ala Cys Val Ile Gln Gly
            90                  95                  100

Val Gly Val Thr Glu Thr Pro Leu Met Lys Glu Asp Ser Ile Leu Ala
        105                 110                 115

Val Arg Lys Tyr Phe Gln Arg Ile Thr Leu Tyr Leu Lys Glu Lys Lys
    120                 125                 130

Tyr Ser Pro Cys Ala Trp Glu Val Val Arg Ala Glu Ile Met Arg Ser
135                 140                 145                 150

Phe Ser Leu Ser Thr Asn Leu
                155

<210> SEQ ID NO 60
<211> LENGTH: 565
<212> TYPE: DNA
<213> ORGANISM: Artificial
<220> FEATURE:
<223> OTHER INFORMATION: truncated human interferon alpha 2b extensin
      fusion with restriction enzyme sites, see Example 5
<220> FEATURE:
<221> NAME/KEY: CDS
<222> LOCATION: (11)..(556)
<220> FEATURE:
<221> NAME/KEY: mat_peptide
<222> LOCATION: (89)..(556)

<400> SEQUENCE: 60
```

```
ttaattaaca atg gga aaa atg gct tct cta ttt gcc aca ttt tta gtg        49
           Met Gly Lys Met Ala Ser Leu Phe Ala Thr Phe Leu Val
               -25             -20             -15 gtt tta gtg tca ctt agc tta gct agc gaa agc tcc gcc tgc gac tta        97
Val Leu Val Ser Leu Ser Leu Ala Ser Glu Ser Ser Ala Cys Asp Leu
            -10             -5              -1  1 cca caa act cac agc ctt ggt agt agg aga acg ttg atg tta ttg gcg       145
Pro Gln Thr His Ser Leu Gly Ser Arg Arg Thr Leu Met Leu Leu Ala
    5               10              15 cag atg agg aga ata tct tta ttc tct tgt ttg aag gat aga cat gac       193
Gln Met Arg Arg Ile Ser Leu Phe Ser Cys Leu Lys Asp Arg His Asp
20              25              30              35 ttc gga ttt cca caa gag gaa ttt ggt aat caa ttc caa aag gct gaa       241
Phe Gly Phe Pro Gln Glu Glu Phe Gly Asn Gln Phe Gln Lys Ala Glu
                40              45              50 act ata cct gta tta cat gag atg ata cag caa atc ttc aat ctg ttt       289
Thr Ile Pro Val Leu His Glu Met Ile Gln Gln Ile Phe Asn Leu Phe
                    55              60              65 agc aca aaa gac tca tct gct gca tgg gac gaa act ctc tta gac aaa       337
Ser Thr Lys Asp Ser Ser Ala Ala Trp Asp Glu Thr Leu Leu Asp Lys
            70              75              80 ttc tac act gaa ttg tac caa cag ctt aat gac ttg gaa gcc tgt gtg       385
Phe Tyr Thr Glu Leu Tyr Gln Gln Leu Asn Asp Leu Glu Ala Cys Val
85              90              95 ata cag gga gtg ggt gta acg gag act cca ttg atg aag gag gac agc       433
Ile Gln Gly Val Gly Val Thr Glu Thr Pro Leu Met Lys Glu Asp Ser
100             105             110             115 ata ctg gca gtg agg aaa tac ttc caa cga atc act tta tac ctg aaa       481
Ile Leu Ala Val Arg Lys Tyr Phe Gln Arg Ile Thr Leu Tyr Leu Lys
                120             125             130 gag aag aaa tac tca cct tgt gcc tgg gag gtt gtc aga gca gaa ata       529
Glu Lys Lys Tyr Ser Pro Cys Ala Trp Glu Val Val Arg Ala Glu Ile
                135             140             145 atg aga tct ttc agt ctt tct act aac tgactcgag                         565
Met Arg Ser Phe Ser Leu Ser Thr Asn
                150             155

<210> SEQ ID NO 61
<211> LENGTH: 182
<212> TYPE: PRT
<213> ORGANISM: Artificial
<220> FEATURE:
<223> OTHER INFORMATION: Synthetic Construct

<400> SEQUENCE: 61

Met Gly Lys Met Ala Ser Leu Phe Ala Thr Phe Leu Val Val Leu Val
    -25             -20             -15

Ser Leu Ser Leu Ala Ser Glu Ser Ser Ala Cys Asp Leu Pro Gln Thr
-10             -5              -1  1               5

His Ser Leu Gly Ser Arg Arg Thr Leu Met Leu Leu Ala Gln Met Arg
            10              15              20

Arg Ile Ser Leu Phe Ser Cys Leu Lys Asp Arg His Asp Phe Gly Phe
        25              30              35

Pro Gln Glu Glu Phe Gly Asn Gln Phe Gln Lys Ala Glu Thr Ile Pro
    40              45              50

Val Leu His Glu Met Ile Gln Gln Ile Phe Asn Leu Phe Ser Thr Lys
55              60              65              70

Asp Ser Ser Ala Ala Trp Asp Glu Thr Leu Leu Asp Lys Phe Tyr Thr
            75              80              85

Glu Leu Tyr Gln Gln Leu Asn Asp Leu Glu Ala Cys Val Ile Gln Gly
```

```
                    90                 95                100
Val Gly Val Thr Glu Thr Pro Leu Met Lys Glu Asp Ser Ile Leu Ala
        105                 110                 115

Val Arg Lys Tyr Phe Gln Arg Ile Thr Leu Tyr Leu Lys Glu Lys Lys
120                 125                 130

Tyr Ser Pro Cys Ala Trp Glu Val Val Arg Ala Glu Ile Met Arg Ser
135                 140                 145                 150

Phe Ser Leu Ser Thr Asn
                155

<210> SEQ ID NO 62
<211> LENGTH: 562
<212> TYPE: DNA
<213> ORGANISM: Artificial
<220> FEATURE:
<223> OTHER INFORMATION: truncated human interferon alpha 2b extensin
      fusion with restriction enzyme sites, see Example 5
<220> FEATURE:
<221> NAME/KEY: CDS
<222> LOCATION: (11)..(553)
<220> FEATURE:
<221> NAME/KEY: mat_peptide
<222> LOCATION: (89)..(553)

<400> SEQUENCE: 62
ttaattaaca atg gga aaa atg gct tct cta ttt gcc aca ttt tta gtg        49
           Met Gly Lys Met Ala Ser Leu Phe Ala Thr Phe Leu Val
               -25                 -20                 -15 gtt tta gtg tca ctt agc tta gct agc gaa agc tcc gcc tgc gac tta      97
Val Leu Val Ser Leu Ser Leu Ala Ser Glu Ser Ser Ala Cys Asp Leu
        -10                 -5                  -1  1 cca caa act cac agc ctt ggt agt agg aga acg ttg atg tta ttg gcg     145
Pro Gln Thr His Ser Leu Gly Ser Arg Arg Thr Leu Met Leu Leu Ala
        5                   10                  15 cag atg agg aga ata tct tta ttc tct tgt ttg aag gat aga cat gac     193
Gln Met Arg Arg Ile Ser Leu Phe Ser Cys Leu Lys Asp Arg His Asp
20                  25                  30                  35 ttc gga ttt cca caa gag gaa ttt ggt aat caa ttc caa aag gct gaa     241
Phe Gly Phe Pro Gln Glu Glu Phe Gly Asn Gln Phe Gln Lys Ala Glu
                40                  45                  50 act ata cct gta tta cat gag atg ata cag caa atc ttc aat ctg ttt     289
Thr Ile Pro Val Leu His Glu Met Ile Gln Gln Ile Phe Asn Leu Phe
            55                  60                  65 agc aca aaa gac tca tct gct gca tgg gac gaa act ctc tta gac aaa     337
Ser Thr Lys Asp Ser Ser Ala Ala Trp Asp Glu Thr Leu Leu Asp Lys
        70                  75                  80 ttc tac act gaa ttg tac caa cag ctt aat gac ttg gaa gcc tgt gtg     385
Phe Tyr Thr Glu Leu Tyr Gln Gln Leu Asn Asp Leu Glu Ala Cys Val
    85                  90                  95 ata cag gga gtg ggt gta acg gag act cca ttg atg aag gag gac agc     433
Ile Gln Gly Val Gly Val Thr Glu Thr Pro Leu Met Lys Glu Asp Ser
100                 105                 110                 115 ata ctg gca gtg agg aaa tac ttc caa cga atc act tta tac ctg aaa     481
Ile Leu Ala Val Arg Lys Tyr Phe Gln Arg Ile Thr Leu Tyr Leu Lys
                120                 125                 130 gag aag aaa tac tca cct tgt gcc tgg gag gtt gtc aga gca gaa ata     529
Glu Lys Lys Tyr Ser Pro Cys Ala Trp Glu Val Val Arg Ala Glu Ile
            135                 140                 145 atg aga tct ttc agt ctt tct act tgactcgag                            562
Met Arg Ser Phe Ser Leu Ser Thr
        150                 155
```

```
<210> SEQ ID NO 63
<211> LENGTH: 181
<212> TYPE: PRT
<213> ORGANISM: Artificial
<220> FEATURE:
<223> OTHER INFORMATION: Synthetic Construct

<400> SEQUENCE: 63

Met Gly Lys Met Ala Ser Leu Phe Ala Thr Phe Leu Val Val Leu Val
    -25             -20                 -15
Ser Leu Ser Leu Ala Ser Glu Ser Ser Ala Cys Asp Leu Pro Gln Thr
-10             -5                  -1  1                 5
His Ser Leu Gly Ser Arg Arg Thr Leu Met Leu Leu Ala Gln Met Arg
            10                  15                  20
Arg Ile Ser Leu Phe Ser Cys Leu Lys Asp Arg His Asp Phe Gly Phe
            25                  30                  35
Pro Gln Glu Glu Phe Gly Asn Gln Phe Gln Lys Ala Glu Thr Ile Pro
        40                  45                  50
Val Leu His Glu Met Ile Gln Gln Ile Phe Asn Leu Phe Ser Thr Lys
55                  60                  65                  70
Asp Ser Ser Ala Ala Trp Asp Glu Thr Leu Leu Asp Lys Phe Tyr Thr
                75                  80                  85
Glu Leu Tyr Gln Gln Leu Asn Asp Leu Glu Ala Cys Val Ile Gln Gly
            90                  95                  100
Val Gly Val Thr Glu Thr Pro Leu Met Lys Glu Asp Ser Ile Leu Ala
        105                 110                 115
Val Arg Lys Tyr Phe Gln Arg Ile Thr Leu Tyr Leu Lys Glu Lys Lys
        120                 125                 130
Tyr Ser Pro Cys Ala Trp Glu Val Val Arg Ala Glu Ile Met Arg Ser
135                 140                 145                 150
Phe Ser Leu Ser Thr
                155

<210> SEQ ID NO 64
<211> LENGTH: 4
<212> TYPE: PRT
<213> ORGANISM: Artificial
<220> FEATURE:
<223> OTHER INFORMATION: Synthetic Construct

<400> SEQUENCE: 64

Lys Asp Glu Leu
1
```